(12) United States Patent
Boggs et al.

(10) Patent No.: US 8,318,656 B2
(45) Date of Patent: Nov. 27, 2012

(54) PRODUCTION PROCESSES AND SYSTEMS, COMPOSITIONS, SURFACTANTS, MONOMER UNITS, METAL COMPLEXES, PHOSPHATE ESTERS, GLYCOLS, AQUEOUS FILM FORMING FOAMS, AND FOAM STABILIZERS

(75) Inventors: Janet Boggs, Crawfordsville, IN (US); Stephan Brandstadter, Indianapolis, IN (US); John Chien, West Lafayette, IN (US); Vimal Sharma, West Lafayette, IN (US); E. Bradley Edwards, Lafayette, IN (US); Vicki Hedrick, Brookston, IN (US); Andrew Jackson, West Lafayette, IN (US); Gregory Leman, Waco, TX (US); Edward Norman, Chester Springs, PA (US); Robert Kaufman, St. Louis, MO (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/024,836

(22) Filed: Feb. 10, 2011

(65) Prior Publication Data
US 2012/0071689 A1 Mar. 22, 2012

Related U.S. Application Data

(62) Division of application No. 10/587,444, filed on Jul. 3, 2007, now Pat. No. 7,943,567.

(51) Int. Cl.
| | |
|---|---|
| C11D 1/00 | (2006.01) |
| C11D 3/24 | (2006.01) |
| C07C 17/00 | (2006.01) |
| C07C 19/08 | (2006.01) |
| C07C 21/18 | (2006.01) |
| C07C 22/08 | (2006.01) |

(52) U.S. Cl. ........ 510/535; 510/475; 570/123; 570/125; 570/126; 570/127; 570/138; 564/96

(58) Field of Classification Search .................. 510/475, 510/535; 570/123, 125, 126, 127, 138; 564/96
See application file for complete search history.

(56) References Cited

U.S. PATENT DOCUMENTS
2,559,749 A 7/1951 Benning
(Continued)

FOREIGN PATENT DOCUMENTS
DE 2120868 11/1971
(Continued)

OTHER PUBLICATIONS
Sawada, Hideo: "Novel Self-Assembled Molecular Aggregates Formed by Fluoroalkyl End-Capped Oligomers and Their Application" *Journal of Fluorine Chemistry 121* (2003), pp. 111-130.

(Continued)

*Primary Examiner* — Brian P Mruk

(57) ABSTRACT

Production processes and systems are provided that include reacting halogenated compounds, dehalogenating compounds, reacting alcohol's, reacting olefins and a saturated compounds, reacting reactants having at least two —$CF_3$ groups with reactants having cyclic groups, $R_F$-compositions such as $R_F$-intermediates, $R_F$-surfactants, $R_F$-monomers, $R_F$-monomer units, $R_F$-metal complexes, $R_F$-phosphate esters, $R_F$-glycols, $R_F$-urethanes, and or $R_F$-foam stabilizers. The $R_F$ portion can include at least two groups —$CF_3$ groups, at least three —$CF_3$ groups, and/or at least two —$CF_3$ groups and at least two —$CH_2$ groups. Detergents, emulsifiers, paints, adhesives, inks, wetting agents, foamers, and defoamers including the $R_F$-surfactant composition are provided. Acrylics, resins, and polymers are provided that include a $R_F$-monomer unit. Compositions are provided that include a substrate having a $R_F$-composition thereover. Aqueous Film Forming Foam ("AFFF") formulations are provided that can include $R_F$-surfactants and/or $R_F$-foam stabilizers are provided.

5 Claims, 9 Drawing Sheets

U.S. PATENT DOCUMENTS

| | | | |
|---|---|---|---|
| 2,567,011 A | 9/1951 | Diesslin et al. |
| 2,597,702 A | 5/1952 | Benning |
| 2,995,542 A | 8/1961 | Brown |
| 3,083,224 A | 3/1963 | Brace et al. |
| 3,096,207 A | 7/1963 | Cohen |
| 3,112,241 A | 11/1963 | Mackenzie |
| 3,145,222 A | 8/1964 | Brace |
| 3,172,910 A | 3/1965 | Brace |
| 3,194,840 A | 7/1965 | Berry |
| 3,238,235 A | 3/1966 | Hauptschein et al. |
| 3,256,231 A | 6/1966 | Johnson, Jr. et al. |
| 3,282,906 A | 11/1966 | Fasick et al. |
| 3,304,278 A | 2/1967 | Hauptschein et al. |
| 1,092,141 A | 11/1967 | Daikin et al. |
| 3,351,643 A | 11/1967 | Hauptschein et al. |
| 3,351,644 A | 11/1967 | Hauptschein et al. |
| 3,450,755 A | 6/1969 | Ahlbrecht |
| 3,457,247 A | 7/1969 | Katsushima et al. |
| 3,458,571 A | 7/1969 | Tokoli |
| 3,475,333 A | 10/1969 | Meldrum et al. |
| 3,491,169 A | 1/1970 | Raynolds et al. |
| 3,497,575 A | 2/1970 | Kleiner et al. |
| 3,498,958 A | 3/1970 | Ray-Chaudhuri et al. |
| 3,514,420 A | 5/1970 | Katsushima et al. |
| 3,532,659 A | 10/1970 | Hager et al. |
| 3,536,749 A | 10/1970 | Groves |
| 3,544,663 A | 12/1970 | Hauptschein et al. |
| 3,574,518 A | 4/1971 | Detomaso |
| 3,575,940 A | 4/1971 | Katsushima et al. |
| 3,623,963 A | 11/1971 | Voss et al. |
| 3,636,085 A | 1/1972 | Kleiner |
| 3,721,706 A | 3/1973 | Hoffman et al. |
| 3,752,783 A | 8/1973 | Iwantani |
| 3,759,981 A | 9/1973 | Hager et al. |
| 3,816,277 A | 6/1974 | Haszeldine et al. |
| 3,824,126 A | 7/1974 | Katsushima et al. |
| 3,839,425 A | 10/1974 | Bartlett |
| 3,843,735 A | 10/1974 | Knell et al. |
| 3,883,596 A | 5/1975 | Hager et al. |
| 3,899,484 A | 8/1975 | Walter |
| 3,906,049 A | 9/1975 | Hager et al. |
| 3,907,576 A | 9/1975 | Dear et al. |
| 3,919,361 A | 11/1975 | Katsushima et al. |
| 3,933,819 A | 1/1976 | Toukan et al. |
| 3,957,657 A | 5/1976 | Chiesa, Jr. |
| 4,000,188 A | 12/1976 | Dear et al. |
| 4,043,923 A | 8/1977 | Loudas |
| 4,060,132 A | 11/1977 | Chiesa, Jr. |
| 4,060,489 A | 11/1977 | Chiesa, Jr. |
| 4,081,399 A | 3/1978 | Dear et al. |
| 4,089,804 A | 5/1978 | Falk |
| 4,113,748 A | 9/1978 | Hager et al. |
| 4,126,633 A | 11/1978 | Toukan et al. |
| 4,127,711 A | 11/1978 | Lore et al. |
| 4,134,754 A | 1/1979 | Hoffmann |
| 4,145,382 A | 3/1979 | Hayashi et al. |
| 4,147,851 A | 4/1979 | Raynolds |
| 4,170,636 A | 10/1979 | Engel et al. |
| 4,177,351 A | 12/1979 | Toukan et al. |
| 4,188,307 A | 2/1980 | Bathelt |
| 4,192,754 A | 3/1980 | Marshall et al. |
| 4,209,456 A | 6/1980 | Billenstein et al. |
| 4,230,495 A | 10/1980 | Lee et al. |
| 4,254,266 A | 3/1981 | Toukan et al. |
| 4,283,533 A | 8/1981 | Richter |
| 4,303,534 A | 12/1981 | Hisamoto et al. |
| 4,306,979 A | 12/1981 | Tsuji |
| 4,317,859 A | 3/1982 | Smith |
| 4,351,946 A | 9/1982 | Toukan et al. |
| 4,366,299 A | 12/1982 | Dessaint |
| 4,387,032 A | 6/1983 | Chiesa, Jr. |
| 4,388,212 A | 6/1983 | Richter |
| 4,419,298 A | 12/1983 | Falk et al. |
| 4,420,434 A | 12/1983 | Falk |
| 4,424,133 A | 1/1984 | Mulligan |
| 4,460,480 A | 7/1984 | Kleiner et al. |
| 4,464,267 A | 8/1984 | Chiesa, Jr. et al. |
| 4,472,286 A | 9/1984 | Falk |
| 4,478,975 A | 10/1984 | Dessaint et al. |
| 4,486,391 A | 12/1984 | Hashimoto |
| 4,507,859 A | 4/1985 | Shinjo |
| 4,563,287 A | 1/1986 | Hisamoto et al. |
| 4,591,473 A | 5/1986 | Lofquist et al. |
| 4,600,774 A | 7/1986 | Koshar |
| 4,697,011 A | 9/1987 | DesMarteau |
| 4,717,744 A | 1/1988 | Boutevin et al. |
| 4,720,578 A | 1/1988 | Liu |
| 4,760,205 A | 7/1988 | Probst et al. |
| 4,833,274 A | 5/1989 | Caporiccio et al. |
| 4,879,324 A | 11/1989 | Lausberg et al. |
| 4,898,981 A | 2/1990 | Falk et al. |
| 4,983,769 A | 1/1991 | Bertocchio et al. |
| 4,985,526 A | 1/1991 | Kishita et al. |
| 5,026,910 A | 6/1991 | Bollens et al. |
| 5,045,634 A | 9/1991 | Fernandez et al. |
| 5,091,550 A | 2/1992 | Falk et al. |
| 5,107,021 A | 4/1992 | Bollens et al. |
| 5,132,445 A | 7/1992 | Falk et al. |
| 5,218,021 A | 6/1993 | Clark et al. |
| 5,240,990 A | 8/1993 | Kallfass et al. |
| 5,310,870 A | 5/1994 | Peavy |
| 5,368,972 A * | 11/1994 | Yamashita et al. ....... 430/137.11 |
| 5,391,721 A | 2/1995 | Hanen et al. |
| 5,395,997 A | 3/1995 | Van Der Puy et al. |
| 5,439,998 A | 8/1995 | Lina et al. |
| 5,478,486 A | 12/1995 | Incorvia |
| 5,491,261 A | 2/1996 | Haniff et al. |
| 5,504,265 A | 4/1996 | Krespan et al. |
| 5,508,099 A | 4/1996 | Incorvia |
| 5,534,192 A | 7/1996 | Incorvia et al. |
| 5,539,024 A | 7/1996 | Kirchmeyer et al. |
| 5,547,711 A | 8/1996 | Kirchmeyer et al. |
| 5,629,372 A | 5/1997 | Anton et al. |
| 5,639,845 A | 6/1997 | Inomata et al. |
| 5,648,527 A | 7/1997 | Prossel et al. |
| 5,648,528 A | 7/1997 | Prossel et al. |
| 5,674,961 A | 10/1997 | Fitzgerald |
| 5,798,415 A | 8/1998 | Corpart et al. |
| 5,827,919 A | 10/1998 | May |
| 5,847,206 A | 12/1998 | Pavia et al. |
| 5,847,243 A | 12/1998 | Skiya et al. |
| 5,883,185 A | 3/1999 | Matsumura et al. |
| 5,919,527 A | 7/1999 | Fitzgerald et al. |
| 5,965,656 A | 10/1999 | Yamamoto et al. |
| 6,002,002 A | 12/1999 | Ürögdi et al. |
| 6,015,838 A | 1/2000 | Stern et al. |
| 6,031,141 A | 2/2000 | Mallikarjuna et al. |
| 6,120,892 A | 9/2000 | Fitzgerald et al. |
| 6,197,382 B1 | 3/2001 | Ornstein et al. |
| 6,218,464 B1 | 4/2001 | Parker et al. |
| 6,235,951 B1 | 5/2001 | Sakyu et al. |
| 6,284,853 B1 | 9/2001 | Yamana et al. |
| 6,294,107 B1 | 9/2001 | Peters et al. |
| 6,297,308 B1 | 10/2001 | Jariwala et al. |
| 6,379,578 B1 | 4/2002 | Shiga |
| 6,383,569 B2 | 5/2002 | Ornstein et al. |
| 6,451,717 B1 | 9/2002 | Fitzgerald et al. |
| 6,486,245 B1 | 11/2002 | Thünemann et al. |
| 6,509,300 B1 | 1/2003 | Gupta |
| 6,525,127 B1 | 2/2003 | Jariwala et al. |
| 6,536,804 B1 | 3/2003 | Dunsmore et al. |
| 6,566,470 B2 | 5/2003 | Kantamneni et al. |
| 6,613,862 B2 | 9/2003 | Clark et al. |
| 6,646,088 B2 | 11/2003 | Fan et al. |
| 6,800,788 B2 | 10/2004 | Bradley et al. |
| 6,803,109 B2 | 10/2004 | Qiu et al. |
| 6,803,425 B2 | 10/2004 | Hintzer et al. |
| 6,809,216 B2 | 10/2004 | Bradley et al. |
| 6,814,880 B1 | 11/2004 | Graf et al. |
| 6,818,253 B2 | 11/2004 | Kimbrell |
| 6,818,717 B2 | 11/2004 | Kantamneni |
| 6,821,496 B2 | 11/2004 | Igumnov et al. |
| 6,824,754 B2 | 11/2004 | Subramaniam et al. |
| 6,824,882 B2 | 11/2004 | Boardman et al. |
| 6,830,703 B2 | 12/2004 | Klug et al. |
| 6,833,419 B2 | 12/2004 | Morschhäuser et al. |
| 2001/0000343 A1 | 4/2001 | Bowers |

| | | | |
|---|---|---|---|
| 2002/0042034 | A1 | 4/2002 | Yoshioka |
| 2003/0013924 | A1 | 1/2003 | Howell et al. |
| 2003/0092862 | A1 | 5/2003 | Thomas et al. |
| 2003/0109662 | A1 | 6/2003 | Medsker et al. |
| 2003/0153780 | A1 | 8/2003 | Haniff et al. |
| 2003/0195314 | A1 | 10/2003 | Buckanin et al. |
| 2003/0207202 | A1 | 11/2003 | Fujita et al. |

FOREIGN PATENT DOCUMENTS

| | | | |
|---|---|---|---|
| DE | 2239709 | | 2/1973 |
| DE | 2247111 | | 4/1974 |
| DE | 2247182 | | 4/1974 |
| EP | 765676 | | 4/1997 |
| GB | 2 018 759 | | 4/1978 |
| GB | 2 070 595 | | 2/1980 |
| JP | 43020466 | | 9/1968 |
| JP | 44001216 | | 1/1969 |
| JP | 48023684 | | 3/1973 |
| JP | 49040040 | | 10/1974 |
| JP | 53081799 | | 7/1978 |
| JP | 55071779 | | 5/1980 |
| JP | 56122336 | | 9/1981 |
| JP | 56169666 | | 12/1981 |
| JP | 58042682 | | 3/1983 |
| JP | 58201752 | | 11/1983 |
| JP | 59059977 | | 4/1984 |
| JP | 61069813 | | 4/1986 |
| JP | 2-12681 | | 2/1990 |
| JP | 04272986 | | 9/1992 |
| JP | 04272987 | | 9/1992 |
| JP | 7-793 | | 7/1995 |
| JP | 08012536 | | 1/1996 |
| JP | 08081883 | | 3/1996 |
| JP | 11-29508 | * | 2/1999 |
| JP | 2000126327 | | 5/2000 |
| JP | 200015840 | | 6/2000 |
| JP | 2003312156 | | 11/2003 |
| WO | WO 94/18245 | | 8/1994 |
| WO | WO 98/19742 | | 5/1998 |
| WO | WO 01/27235 | A1 | 4/2001 |
| WO | 2005/002617 | | 1/2005 |
| WO | 2005/003137 | | 1/2005 |
| WO | 2005/003138 | | 1/2005 |
| WO | 2005/003429 | | 1/2005 |
| WO | 2005/003433 | | 1/2005 |

OTHER PUBLICATIONS

Sawada, et al.; "Synthesis and Surfactant Properties of Fluoroalkylated Sulfonic Acid Oligomers as a New Class of Human Immunodeficiency Virus Inhibitors", *Journal of Fluorine Chemistry* 79(1996), pp. 149-155.

Krafft, et al.; "Highly fluorinated amphiphiles and colloidal systems . . . "; Biochimie 1998; 1 page; (Database 1998:620482 CAPLUS).

Nivet et al; "Synthesis and bioacceptability of fluorinated . . . "; European Journal of Medicinal Chemistry, 1992; 1 page; (Database 1993:408334 CAPLUS).

Sawada et al.; "Synthesis and properties of . . . "; European Polymer Journal, 1999, 1 page; (Database 1999:411635 CAPLUS).

Nivet et al.; "Evaluation of a series of . . . "; Journal of Dispersion Science and Technology, 1992 ; 1 page; (Database 1993:66807 CAPLUS).

Nivet et al.; "Synthesis of new *perfluoroalkylated* . . . "; New Journal of Chemistry 1994; 1 page; (Database 1995:38527 CAPLUS).

Sawada et al.; "Novel fluorinated . . . "; Nihon Yukagakkaishi, 2000; 1 page; (Database 2000:752279 CAPLUS).

Enjalbert et al.; "Synthesis of new cationic and amphoteric triple-chain . . . "; Research on Chemical Intermediates, 1998; 1 page; (Database 1998:422963 CAPLUS).

Szonyl et al.; "Synthesis of new amphoteric . . . double-chain . . . "; Rivista Italiana delle Sostanze Grasse, 1998; 1 page; (Database 1998:465664 CAPLUS).

Prescher et al.; "Nitrogen-containing fluorosurfactants:"; Tenside, Surfactants, Detergents, 1992; 1 page; (Database 1992:653923 CAPLUS).

Enjalbert et al.; "Synthesis fo new double-chain cationic . . . "; Tenside, Surfactants, Detergents, 1998: 1 page; (Database 1992:550675 CAPLUS).

Rzhevskii et al.; "Testing of *surfactants* . . . "; Tsvetnye Metally (Moscow), 1998; 1 page; (Database 1999:114673 CAPLUS).

Murata et al.; "Selective synthesis of fluorinated ethers . . . "; The Royal Society of Chemistry, 2002; pp. 60-63.

* cited by examiner

US 8,318,656 B2

PRODUCTION PROCESSES AND SYSTEMS, COMPOSITIONS, SURFACTANTS, MONOMER UNITS, METAL COMPLEXES, PHOSPHATE ESTERS, GLYCOLS, AQUEOUS FILM FORMING FOAMS, AND FOAM STABILIZERS

CLAIM FOR PRIORITY

This application claims priority to U.S. Provisional Patent Application Ser. No. 60/540,612, entitled Fluorine Functional Groups, Fluorine Compositions, Processes for Manufacturing Fluorine Compositions, and Material Treatments, filed Jan. 30, 2004, the entirety of which is incorporated by reference herein.

TECHNICAL FIELD

The present invention relates to the field of halogenated compositions, processes for manufacturing halogenated compositions, and, more specifically, fluorinated compositions, processes for manufacturing fluorinated compositions and methods for treating substrates with the fluorinated compositions.

BACKGROUND

Compositions such as surfactants and polymers, for example, have incorporated fluorine to affect the performance of the composition when the composition is used as a treatment for materials and when the composition is used to enhance the performance of materials. For example, surfactants incorporating fluorinated functional groups can be used as fire extinguishants either alone or in formulations such as aqueous film forming foams (AFFF). Traditional fluorosurfactants, such as perfluoro-octyl sulfonate derivatives (PFOS), have linear perfluorinated portions.

Polymers incorporating fluorine have been used to treat materials. Exemplary fluorinated treatments include compositions such as Scotchguard®.

SUMMARY

Production processes and systems are provided that include: a reactor having at least one interior sidewall that includes glass; reacting a halogenated compound with an allyl-comprising compound in the presence of water to form a halogenated intermediate; dehalogenating a portion of a heterohalogenated alcohol to form a homohalogenated alcohol, with the heterohalogenated alcohol including at least two $-CF_3$ groups and at least one halogen other than fluorine; reacting an alcohol to form an acrylate, with the alcohol including at least two $-CF_3$ groups and a cyclic group; reacting an olefin with a saturated compound to form a saturated product, with the olefin including at least two $-CF_3$ groups, the saturated compound including at least two other $-CF_3$ groups, and the saturated product including both the $-CF_3$ groups of the olefin and the $-CF_3$ groups of the saturated compound; and/or reacting a first reactant that includes at least two $-CF_3$ groups with a second reactant that includes a cyclic group to form a compound that includes the two $-CF_3$ groups and the cyclic group.

$R_F$ compositions such as $R_F$-intermediates, $R_F$-surfactants, monomers, $R_F$-monomer units, $R_F$-metal complexes, $R_F$-phosphate esters, $R_F$-glycols, $R_F$-urethanes, and/or $R_F$-foam stabilizers. The $R_F$ portion can include at least two $-CF_3$ groups, at least three $-CF_3$ groups, and/or at least two $-CF_3$ groups and at least two $-CH_2-$ groups.

$R_F$-surfactant compositions such as $R_F$-$Q_s$ are provided, with the $R_F$ portion having a greater affinity for a first part of a system having at least two parts than the $Q_s$ portion, and $Q_s$ having a greater affinity for a second part of the system than the $R_F$ portion. Detergents, emulsifiers, paints, adhesives, inks, wetting agents, foamers, and defoamers including the $R_F$-surfactant composition are provided.

Production processes including providing a first compound, with the first compound including at least two $-CF_3$ groups and two hydrogens, and a portion of the first compound representing the $R_F$ portion of an $R_F$-surfactant and adding a $Q_s$ portion to the $R_F$ portion to form the $R_F$-surfactant are provided. Processes for altering a surface tension of a part of a system having at least two parts are provided that include adding a $R_F$-surfactant.

Acrylics, resins, and polymers are provided that include a $R_F$-monomer unit, with the $R_F$ portion including, for example, a pendant group of the monomer unit. Compositions are provided that include a substrate having a $R_F$-composition thereover.

Production processes are provided that can include providing a $R_F$-monomer and combining the $R_F$-monomer with another monomer to form an oligomer. Exemplary oligomers can include $R_F$-monomer units.

$R_F$-metal complexes are provided that can include a metal and a ligand, with the ligand including $R_F$-$Q_{MC}$. The $Q_{MC}$ portion being coordinated with the metal of the complex, for example.

$R_F$-phosphate esters are provided that can include $R_F$-$Q_{PE}$, with the $Q_{PE}$ portion including the phosphorous portion of the ester.

$R_F$-glycols are provided that can include $R_F$-$Q_h$, with $Q_h$ including a hydroxyl portion of the glycol.

$R_F$-urethanes are also provided such as $R_F$-$Q_U$, with the $Q_U$ portion being the remainder of the urethane.

Aqueous Film Forming Foam ("AFFF") formulations are provided that can include $R_F$-surfactants and/or $R_F$-foam stabilizers.

BRIEF DESCRIPTION OF THE DRAWINGS

Embodiments are described below with reference to the following accompanying drawings.

DETAILED DESCRIPTION

Figure 1:
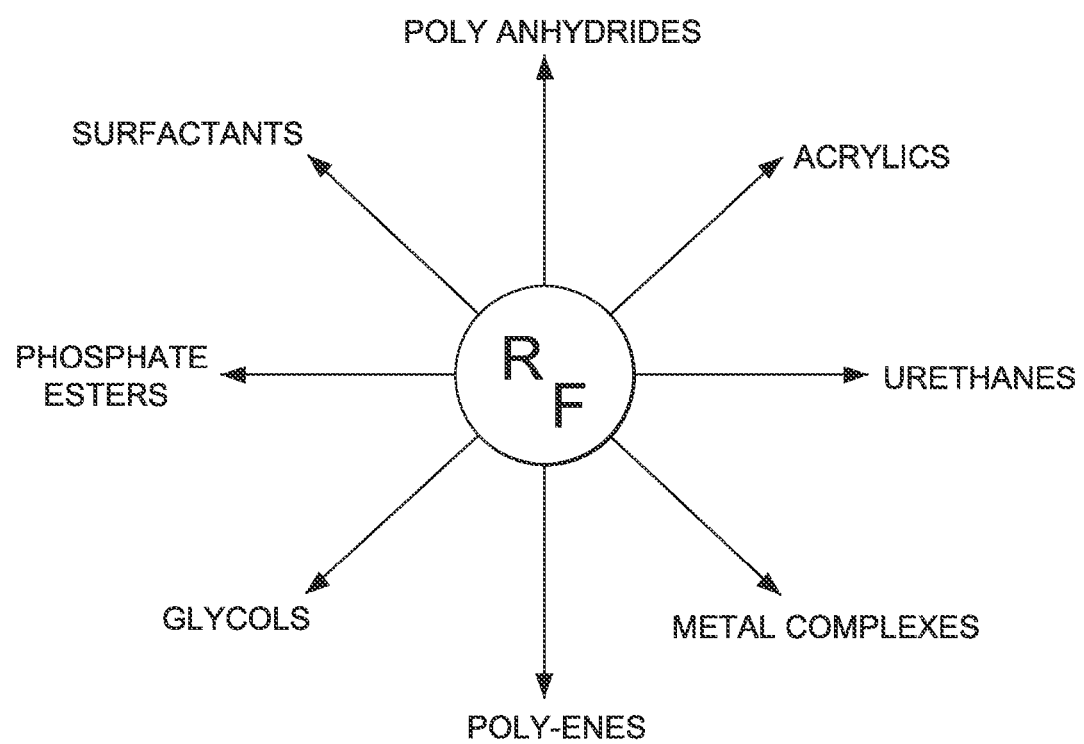
FIG. 1 is a general view of exemplary $R_F$-compositions.

Exemplary $R_F$-compositions and production systems are described with reference to FIGS. 1-8. Referring to FIG. 1, a general view of exemplary $R_F$-compositions is shown. $R_F$-compositions include, but are not limited to, $R_F$-surfactants, $R_F$-monomers, $R_F$-monomer units, $R_F$-metal complexes, $R_F$-phosphate esters, $R_F$-glycols, $R_F$-urethanes, and or $R_F$-foam stabilizers. In exemplary embodiments, poly-anhydrides, acrylics, urethanes, metal complexes, polyenes, and/or phosphate esters can include $R_F$ portions as well.

$R_F$-compositions include compositions that have an $R_F$ portion and/or $R_F$ portions. The $R_F$ portion can be $R_F$-groups, such as pendant groups and/or moieties of compositions. The $R_F$ portion can include at least two —$CF_3$ groups and the —$CF_3$ groups may be terminal. The $R_F$ portion can also include both —$CF_3$ groups and additional groups containing fluorine, such as —$CF_2$— groups. In exemplary embodiments, the $R_F$ portion can include a ratio of —$CF_2$— groups to —$CF_3$ groups that is less than or equal to two, such as $(CF_3)_2CF$— groups. The $R_F$ portion can also include hydrogen. For example, the $R_F$ portion can include two —$CF_3$ groups and hydrogen, such as $(CF_3)_2CH$— groups. The $R_F$ portion can also include two —$CF_3$ groups and a —$CH_2$— group, in other embodiments. The $R_F$ portion can include at least three —$CF_3$ groups, such as two $(CF_3)_3CF$— groups. In exemplary embodiments, the $R_F$ portion can include cyclic groups such as aromatic groups. The $R_F$, portion can include at least two —$CF_3$ groups and at least four carbons with, for example, one of the four carbons including a —$CH_2$— group.

In exemplary implementations. $R_F$-compositions can demonstrate desirable surface energies, affect the surface tension of solutions to which they are exposed, and/or affect the environmental resistance of materials to which they are applied and/or incorporated. Exemplary compositions include, but are not limited to, substrates having $R_F$-compositions thereover and/or liquids having $R_F$-compositions therein. $R_F$ portions can be incorporated into compositions such as polymers, acrylate monomers and polymers, glycols, fluorosurfactants, and/or AFFF formulations. These compositions can be used as dispersing agents or to treat substrates such as textile fabric, textile yarns, leather, paper, plastic, sheeting, wood, ceramic clays, as well as, articles of apparel, wallpaper, paper bags, cardboard boxes, porous earthenware, construction materials such as brick, stone, wood, concrete, ceramics, tile, glass, stucco, gypsum, drywall, particle board, chipboard, carpet, drapery, upholstery, automotive, awning fabrics, and rainwear. $R_F$-compositions can be prepared from $R_F$-intermediates.

$R_F$ portions can be incorporated into $R_F$-compositions and/or can be starting materials for $R_F$-compositions via $R_F$-intermediates. Exemplary $R_F$-intermediates include an $R_F$ portion described above, as well as at least one functional portion that allows for incorporation of the $R_F$ portion into compositions to form $R_F$-compositions. Functional portions can include halogens (e.g., iodine), mercaptan, thiocyanate, sulfonyl chloride, acid, acid halides, hydroxyl, cyano, acetate, allyl, epoxide, acrylic ester, ether, sulfate, thiol, phosphate, and/or amines, for example. Without incorporation and/or reaction, $R_F$-intermediates can include $R_F$-compositions, such as $R_F$-monomers and/or ligands of $R_F$-metal complexes, for example.

$R_F$-intermediates can include $R_F$-$Q_g$ with $R_F$ representing the $R_F$ portion and $Q_g$ representing, for example, the functional portion, and/or, as another example, an element of the periodic table of elements. In exemplary embodiments. $Q_g$ is not a proton, methyl, and/or a methylene group. Exemplary $R_F$-intermediates include, but are not limited to, those in Table 1 below.

TABLE 1

Exemplary $R_F$-intermediates

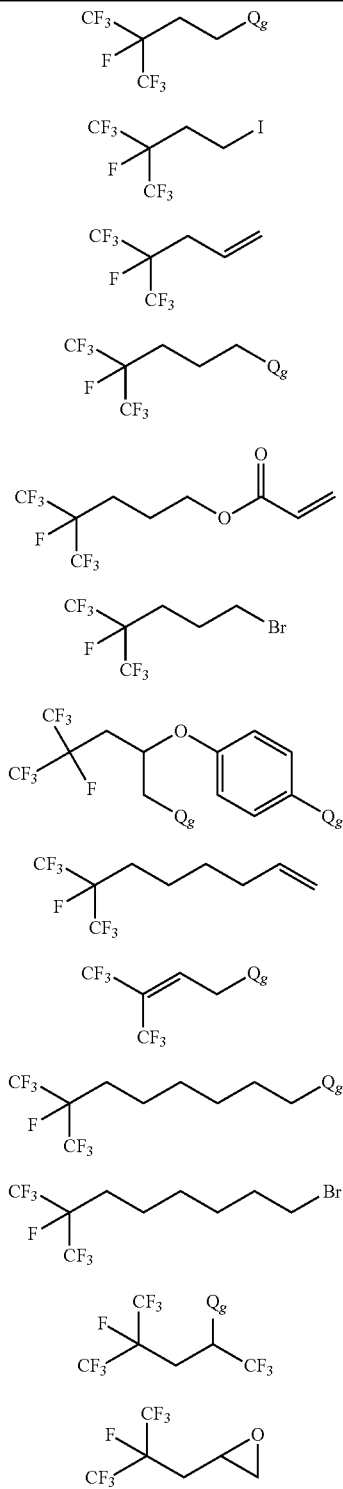

TABLE 1-continued
Exemplary R$_F$-intermediates
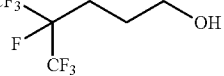
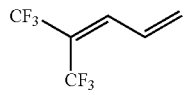
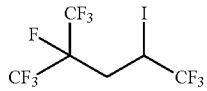
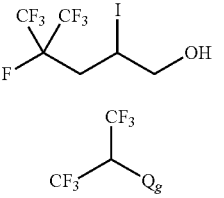
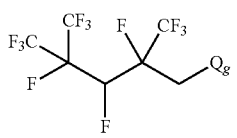
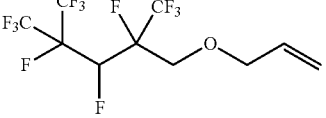
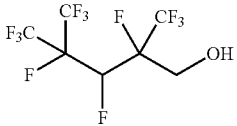
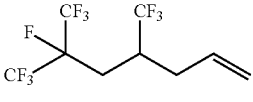
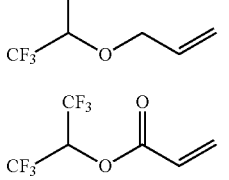
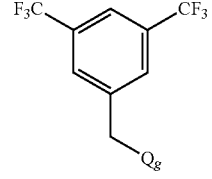
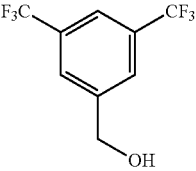
TABLE 1-continued
Exemplary R$_F$-intermediates
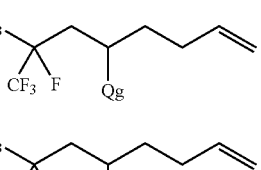
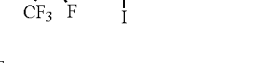
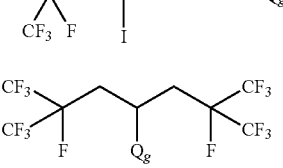
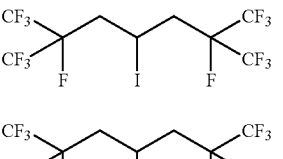
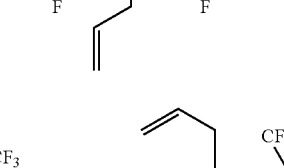
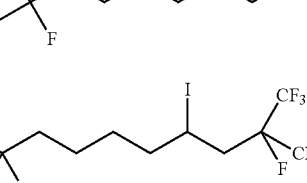
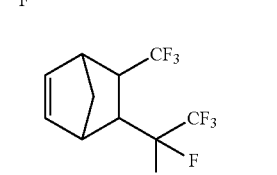
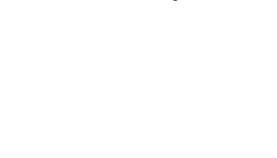

TABLE 1-continued

Exemplary R_F-intermediates

[Chemical structures of exemplary R_F-intermediates shown]

$R_F$-intermediates can also include $$Q_g(R_1-\underset{CF_3}{\underset{|}{CH}})_nR_F, \quad R_F(R_1-\underset{CF_3}{\underset{|}{CH}})Q_g$$

and/or one or both of $$R_F(R_1-\underset{CF_3}{\underset{|}{CH}})_nQ_g \quad \text{and} \quad R_F(CH_2-\underset{CF_3}{\underset{|}{CH}})_nQ_g,$$

with $R_1$ including at least one carbon atom, such as $-CH_2-$, for example. In exemplary embodiments, n can be at least 1 and in other embodiments n can be at least 2 and the $R_F$-intermediate can include one or more of $$R_F(CH_2-\underset{CF_3}{\underset{|}{CH}}-CH_2-\underset{CF_3}{\underset{|}{CH}})Q_g,$$

$$R_F(CH_2-\underset{CF_3}{\underset{|}{CH}}-\overset{CF_3}{\overset{|}{CH}}-CH_2)Q_g,$$

$$R_{Cl}(CH_2-\underset{CF_3}{\underset{|}{CH}}-CH_2-\underset{CF_3}{\underset{|}{CH}})H \quad \text{and/or}$$

$$R_{Cl}(CH_2-\underset{CF_3}{\underset{|}{CH}}-\overset{CF_3}{\overset{|}{CH}}-CH_2)H.$$

The $R_F$-intermediate

[Structure: F3C-C(F)(CF3)-CH2-CH2-I]

(4-iodo-2-(trifluoromethyl)-1,1,1,2-tetrafluorobutane) may be obtained, for example, at Matrix Scientific, P.O. Box 25067, Columbia, S.C. 92994-5067.

The $R_F$-intermediate

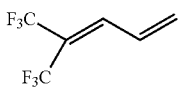

(1,1,1-trifluoro-2-trifluoromethyl-2,4-pentadiene) can be prepared in an exemplary aspect according to J. Org. Chem., Vol. 35, No. 6, 1970, pp. 2096-2099, herein incorporated by reference. 1,1,1-trifluoro-2-trifluoromethyl-2,4-pentadiene can also be prepared according to the following example.

The 1,1,1-trifluoro-2-trifluoromethyl-2,4-pentadiene can be prepared according to scheme (1) below.

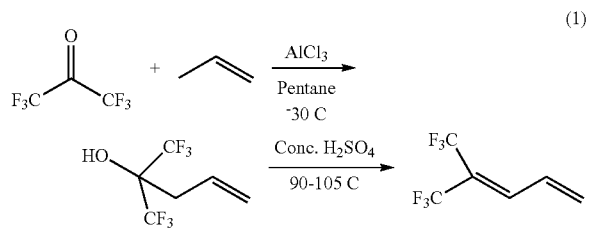

(1)

Referring to scheme (1) above, pentane (300 mL) can be placed in a 500 mL three neck flask and chilled below −30° C. To the pentane can be added hexafluoroacetone (59 grams, 0.36 mole), propylene (16.2 grams, 0.38 mole), and anhydrous aluminum trichloride (0.77 g, 0.006 mole) to form a mixture. This mixture can be stirred and the temperature can be allowed to warm to room temperature over a 3 hour period. A 15% (wt/wt) aqueous HCl solution (20 mL) can be added to the mixture, and the mixture can be washed 3 times with H$_2$O. The aqueous layer, after the wash, can be decanted off, and the organic layer (pentane and propylene) can be dried with MgSO$_4$. Remaining pentane and propylene can be flash vaporized off at 60° C. to give 54.4 grams (70% area percent by gas chromatography) of isomeric 1,1-bis(trifluoromethyl)-3-penten-1-ol.

The crude 1,1-bis(trifluoromethyl)-3-penten-1-ol (54 grams) can be placed in a 250 mL three-neck flask and 125 mL of concentrate H$_2$SO$_4$ added to form a mixture which can be stirred and heated slowly to 95° C. (separating compounds having lower boiling points from the mixture between 34° C. and 55° C.). The 1,1,1-trifluoro-2-trifluoromethyl-2,4-pentadiene (15.6 grams, 45.5% yield) produced can be separate from the mixture as a gas between 70° C. and 74° C.

Figure 2:
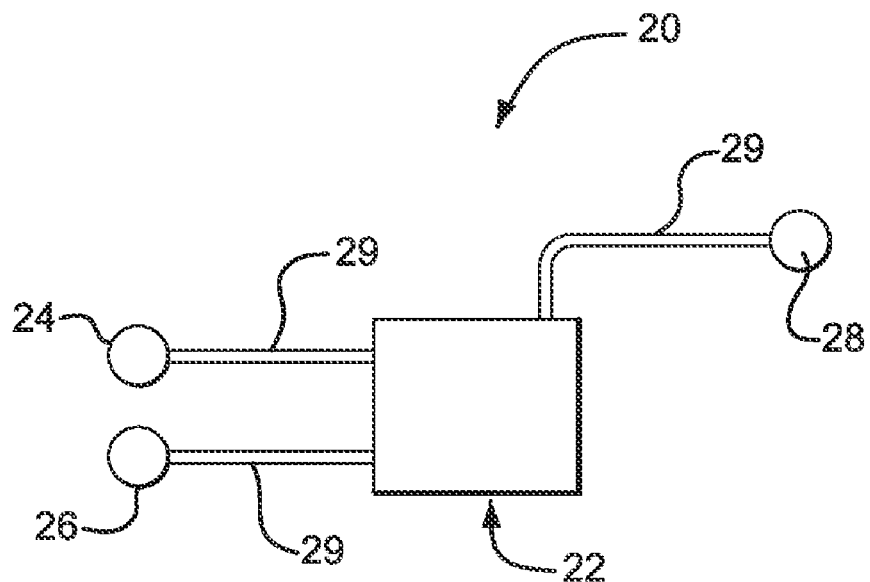
FIG. 2 is an exemplary system for preparing compositions according to an embodiment.

Exemplary $R_F$-intermediates can be prepared from the reactant 2-iodoheptafluoropropane. In an exemplary embodiment, halogenated compounds such as 2-iodoheptafluoropropane can be prepared with reference to FIG. 2. Referring to FIG. 2, a system 20 is depicted that includes a reactor 22 coupled to an alkyl reactant reservoir 24, a halogenating agent reservoir 26, and a halogenated compound reservoir 28. In accordance with exemplary embodiments, system 20 can be used to halogenate an alkyl reactant with a halogenating agent within reactor 22 to form a halogenated compound. Alkyl reactant within alkyl reactant reservoir 24 can include an olefin such as a fluoro-olefin, for example hexafluoropropene. Halogenating agent within halogenating agent reservoir 26 can include a mixture of a salt and a diatomic halogen, such as KF and I$_2$, KF and Br$_2$, and salts such as ammonium salts, for example. In an exemplary embodiment, reactor 22 can be lined with glass and/or Hastelloy®, such as Hastelloy® C.

According to another embodiment, conduits 29 can be configured to provide the contents of reservoirs 24 and 26 to reactor 22 and/or provide the contents of reactor 22 to reservoir 28. Conduits 29 can be lined with glass and/or Hastelloy®, such as Hastelloy® C. Conduits 29 and reactor 22 both can be lined with glass and/or Hastelloy®, such as Hastelloy® C, for example.

In an exemplary embodiment, the halogenating agent may be provided to reactor 22 with a reactant media, such as a polar, aprotic solvent including, for example, acetonitrile and/or dimethyl formamide (DMF). The reactant media may be added through another conduit (not shown) or, simultaneously with the halogenating agent, through reservoir 26. Together, the halogenating agent and the reactant media can form a mixture within reactor 22 to which the alkyl reactant can be added to form another mixture that includes the agent, the media, and the reactant. The alkyl reactant can be reacted within this mixture to form the halogenated compound. In an exemplary embodiment, the reactant media can be in the liquid phase when the alkyl reactant is reacted within the mixture. The mixture may also be agitated when the alkyl reactant is reacted, for example, and the mixture may also be heated. In an exemplary embodiment, hexafluoropropene may be provided to reactor 22 having KF, I$_2$, and acetonitrile therein and a portion of the contents of reactor 22 heated to at least about 90° C., and/or from about 90° C. to about 135° C., to form 2-iodoheptafluoropropane. Hexafluoropropene may also be provided to reactor 22 having KF, I$_2$, and acetonitrile therein with a pressure within reactor 22 being from about 446 kPa to 929 kPa to form 2-iodoheptafluoropropane.

The halogenated compound may also be removed from reactor 22 to reservoir 28 via conduit 29. In an exemplary embodiment, conduit 29, between reservoir 28 and reactor 22, can include a condenser (not shown). A portion of the halogenated compound formed within reactor 22 can be transformed into a gas, the as can be transferred to the condenser, the condenser can return the gas to a liquid, and the liquid can be removed from the condenser and transferred to reservoir 28. In exemplary embodiments, conduit 29, between reactor 22 and 28, being configured to include the condenser, can be referred to as a distillation apparatus. Halogenated compounds such as the 2-iodoheptafluoropropane described above, can be removed from reactor 22 by heating at least a portion of the 2-iodoheptafluoropropane to at least about 40° C.

Exemplary halogenated compounds described above may be used to prepare $R_F$-intermediates such as

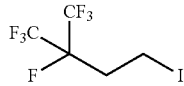

(1,1,1,2-tetrafluoro-2-(trifluoromethyl)-4-iodobutane). For example, and by way of example only, 105.14 grams of 2-iodoheptafluoropropane and 10 grams of ethylene can be added to a 800 mL Parr reactor. The reactor can be heated to about 180° C. for about 6 hours. The reactor can then be cooled and a portion of the contents removed to give about 105.99 grams of the $R_F$-intermediate 1,1,1,2-tetrafluoro-2-(trifluoromethyl)-4-iodobutane being about 86% pure (as determined by gas chromatography). The 1,1,1,2-tetrafluoro-2-(trifluoromethyl)-4-iodobutane can also be distilled at 56° C./96 Torr. 1,1,1,2-tetrafluoro-2-(trifluoromethyl)-4-iodobutane can also be purchased from Matrix Scientific (Catalog number 1104).

Halogenated compounds may also be used to prepare $R_F$-intermediates such as the heterohalogenated intermediate 7,8,8,8-tetrafluoro-7(trifluoromethyl)-5-iodooct-1-ene. The $R_F$-intermediate can be prepared and then dehalogenated to form another $R_F$-intermediate according to scheme (2) below.

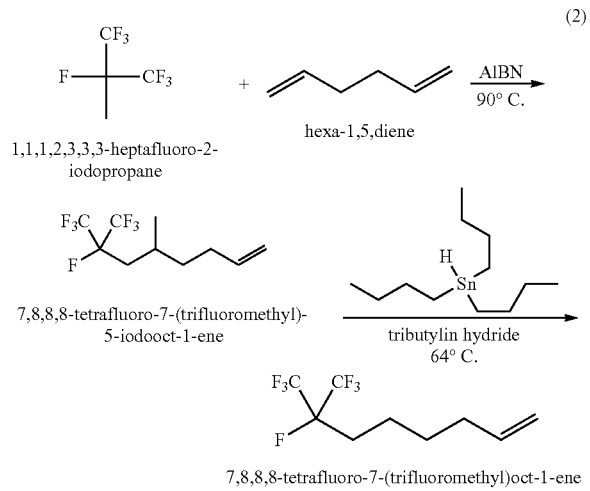

Referring to scheme (2) above, 2-iodoheptafluoropropane (231.3 grams, 0.782 mole), 1,5-hexadiene (126.6 g, 0.767 mole), and 2,2'-azobisisobutyronitrile (AIBN) (13.6 g, 0.083 mole) can be charged together into a clean and dry 750 mL stainless steel autoclave apparatus equipped with a rupture disc, thermocouple, heater bands, electronic temperature controller, dip-tube with needle valve, gas vent with needle valve, pressure gauge, and agitator. The apparatus can then be sealed and heated slowly to about 60° C. where an exotherm can be observed and slowly the temperature can be raised to about 80° C. The apparatus contents can be held at 80° C. for about 72 hours giving about 337 g of crude material. The contents can be vacuum distilled (53° C./5.0 Torr) to give about 125 g 99.6% area percent purity (by gas chromatography) of the $R_F$-intermediate 7,8,8,8-tetrafluoro-7(trifluoromethyl)-5-iodooct-1-ene (m/z 377.7 (M$^+$), 251 (M$^+$–I)), IR spectra: olefinic C—H stretch at (w) 3082 cm$^{-1}$, C=C stretch at (w) 1643 cm$^{-1}$, and fingerprint bands at 729, 1149, 1224, and 1293 cm$^{-1}$, $^1$H NMR, $^{19}$F NMR, $^{13}$C NMR, High Resolution MS can be utilized to determine the 7,8,8,8-tetrafluoro-7(trifluoromethyl)-5-iodooct-1-ene as well.

Referring again to scheme (2) above, the 7,8,8,8-tetrafluoro-7-(trifluoromethyl)-5-iodooct-1-ene (36.1 grams, 0.095 mole) can be added to a 100 mL three-neck round bottom flask equipped with a reflux condenser, heating mantle, thermocouple, electronic heat controller, and agitator and heated to 75° C. Tributyltin hydride (34.6 grams, 0.119 mole) can be added drop-wise through an addition funnel over a 3 hour period to form a mixture. An exotherm can be observed during the addition. The mixture can be vacuum distilled (25° C./5.0 Torr) to give 15.6 grams of the $R_F$-intermediate 7,8,8,8-tetrafluoro-7(trifluoromethyl)oct-1-ene as a clear liquid having about 99.8% area percent purity (by gas chromatography), and 5.5 g of lower purity 7,8,8,8-tetrafluoro-7(trifluoromethyl)oct-1-ene (m/z 252 (M$^+$). 183 (M$^+$–CF$_3$), 69 (M$^+$–C$_8$H$_{11}$F$_4$), 55 (M$^+$–C$_5$H$_4$F$_7$)); IR: olefinic C—H stretch at (w) 3087 cm$^{-1}$, C=C stretch at (w) 1644 cm$^{-1}$, and fingerprint bands at 720, 1135, 1223, and 1315 cm$^{-1}$; $^1$H NMR (CDCl$_3$, 300 MHz) δ 1.40-1.50 (m, 2H), 1.54-1.65 (m, 2H), 1.95-2.14 (m, 2H), 4.95-5.06 (m, 2H), 5.72-5.85 (ddt, J=17.1, 10.2, 6.7, 1H); $^{19}$F NMR (CDCl$_3$, CFCl$_3$, 282 MHz) δ –76.57 (d, J=7.9, 7F), –183.2 (m, $^1$F)).

Figure 3:
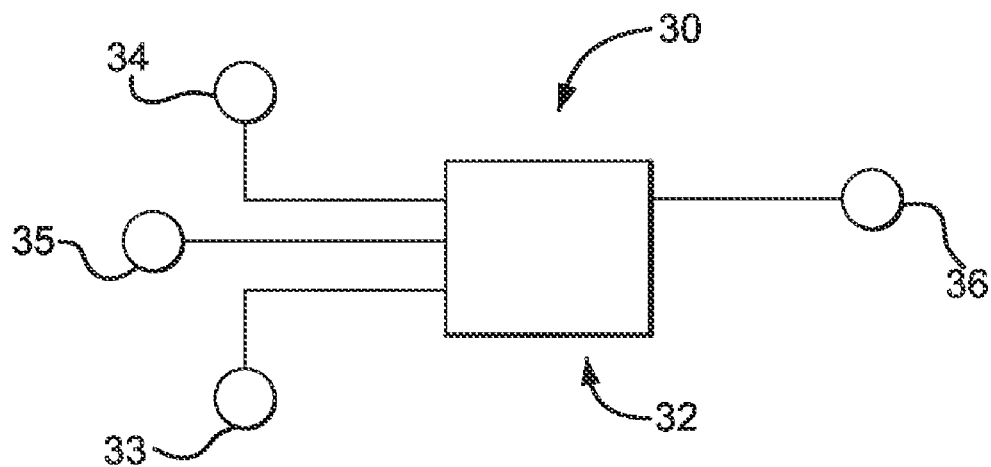
FIG. 3 is an exemplary system for preparing compositions according to an embodiment.

Referring to FIG. 3, system 30 is depicted that includes a reactor 32 configured to receive a halogenated compound, such as the 2-iodoheptafluoropropane described above, from a halogenated compound reservoir 33. The halogenated compound can also include at least two CF$_3$— groups; at least one (CF$_3$)$_2$CF— group; and/or at least two CF$_3$— groups and a halogen other than fluorine, for example. Reactor 32 can also be configured to receive an allyl-comprising compound from an allyl-comprising compound reservoir 34, and water from water reservoir 35. The allyl-comprising compound can include an ester such as allyl acetate, for example. The allyl comprising compound can also include alcohol such as allyl alcohol, as another example.

Reactor 32 can be configured to react the halogenated compound with the allyl-comprising compound in the presence of the water to form an $R_F$-intermediate and provide the $R_F$-intermediate to intermediate reservoir 36. The halogenated compound, allyl-comprising compound and the water can be combined in reactor 32 to a form a mixture. A salt, such as Na$_2$S$_2$O$_5$, may be added to the water to form an aqueous solution prior to forming the mixture, for example. The salt can be as much as 30% (wt/wt) of the solution.

In an exemplary embodiment, where the halogenated compound includes 2-iodoheptafluoropropane; the allyl-comprising compound includes allyl acetate; and the aqueous solution includes Na$_2$S$_2$O$_5$, the $R_F$-intermediate can include 4,5,5,5-tetrafluoro-4-(trifluoromethyl)-2-iodopentyl acetate. Reacting the 2-iodoheptafluoropropane with the allyl acetate in the presence of the solution can include heating at least a portion of the mixture within reactor 32 to at least about 80° C., from about 65° C. to about 100° C., and/or from about 80° C. to about 90° C.

In another exemplary embodiment, where the halogenated compound includes 2-iodoheptafluoropropane; the allyl-comprising compound includes allyl alcohol; and the solution includes Na$_2$S$_2$O$_5$, the $R_F$-intermediate can include 4,5,5,5-tetrafluoro-4-(trifluoromethyl)-2-iodopentan-1-ol. Reacting the 2-iodoheptafluoropropane with the allyl alcohol in the presence of the solution can include heating at least a portion of the mixture within reactor 32 to at least about 80° C., from about 65° C. to about 100° C., and/or from about 80° C. to about 90° C.

An initiator may also be provided to reactor 32 to facilitate the reacting of the halogenated compound with the allyl-comprising compound. An exemplary initiator can include AIBN. Reactor 32 can contain from about 0.01% (wt/wt) to about 10% (wt/wt and/or from about 0.1%(wt/wt) to 5% (wt/wt), of the initiator.

According to an exemplary embodiment, the $R_F$-intermediate can be provided to intermediate reservoir 36 upon formation within reactor 32. Providing the $R_F$-intermediate can include processes for separating the $R_F$-intermediate from the remaining contents of the reactor, those contents including reactants and or by-products. Exemplary methods for providing the $R_F$-intermediate to reservoir 36 can include liquid/liquid separation and/or distillation.

The $R_F$-intermediate formed above may also be reacted to form additional intermediates including additional $R_F$-intermediates. For example, a portion of the intermediate can be unsaturated to form a $R_F$-intermediate that includes a halogenated olefin. In an exemplary embodiment, unsaturating the intermediate can include exposing the intermediate to a reducing agent. The reducing agent can include Zn and/or a mixture of Zn and diethylene glycol for example. The $R_F$-intermediate 4,5,5,5-tetrafluoro-4-(trifluoromethyl)-2-iodopentyl acetate may be unsaturated to form the $R_F$-intermediate 4,5,5,5-tetrafluoro-4-(trifluoromethyl)pent-1-ene, according to one embodiment. The $R_F$-intermediate 4,5,5,5-tetrafluoro-4-(trifluoromethyl)-2-iodopentyl acetate can be combined with a mixture of Zn and diethylene glycol, for example, to form another mixture and the other mixture can be heated to at least about 120° C. to form the $R_F$-intermediate 4,5,5,5-tetrafluoro-4-(trifluoromethyl)pent-1-ene. As another example, the $R_F$-intermediate 4,5,5,5-tetrafluoro-4-(trifluoromethyl)-2-iodopentan-1-ol can be reacted to form the $R_F$-intermediate 4,5,5,5-tetrafluoro-4-(trifluoromethyl)pent-1-ene in the presence of a reducing reagent such as a mixture of Zn and diethylene glycol.

According to another embodiment, the reducing agent can include $POCl_3$, pyridine and/or a mixture of $POCl_3$ and pyridine. For example, the $R_F$-intermediate 4,5,5,5-tetrafluoro-4-(trifluoromethyl)-2-iodopentan-1-ol can be reacted to form the $R_F$-intermediate 4,5,5,5-tetrafluoro-4-(trifluoromethyl)pent-1-ene in the presence of a mixture of $POCl_3$ and pyridine. This reaction can be performed while maintaining the temperature of the mixture between from about 0° C. to about 5° C., for example.

The $R_F$-intermediate

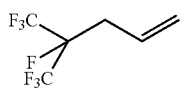

(4,5,5,5-tetrafluoro-4-(trifluoromethyl)pent-1-ene) can also be prepared in an exemplary aspect according to *Synthesis and Characterization of a New Class of Perfluorinated Alkanes: Tetrabis(perfluoroalkyl)alkane*. C. Gambaretto et al., Journal of Fluorine Chemistry, 5892 (2003) pgs 1-7 and U.S. Pat. No. 3,843,735 to Knell et. al., both of which are herein incorporated by reference. The 4,5,5,5-tetrafluoro-4-(trifluoromethyl)pent-1-ene can also be prepared according to scheme (3) below, for example.

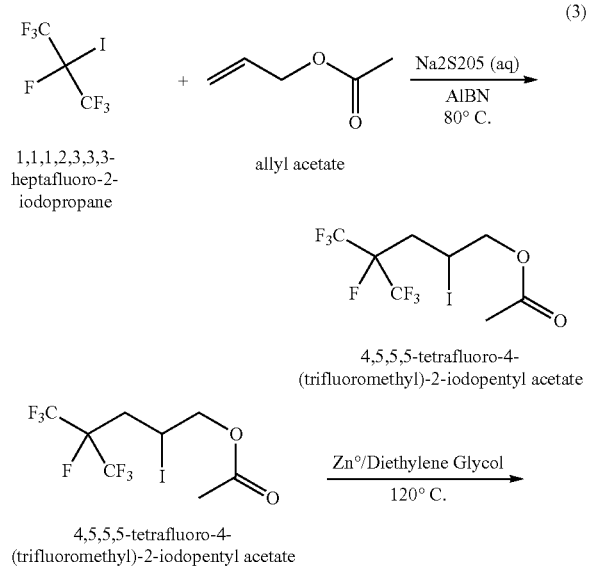

-continued

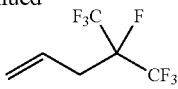

4,5,5,5-tetrafluoro-4-(trifluoromethyl)pent-1-ene

Referring to scheme (3) above, AIBN (9.2 g, 0.06 mole), 1,1,1,2,3,3,3-heptafluoro-2-iodopropane (1651 g, 5.6 mole), and 293 g of 30% (wt/wt) aqueous $Na_2S_2O_5$ can be placed into a 2 L pressure reactor to form a mixture. The reactor can be sealed and heated to 80° C. under autogeneous pressure. Allyl acetate (587 g, 5.9 mole) can be slowly added to this mixture and the mixture can be stirred for an additional 4 hours. After stirring, an organic layer can be observed, removed, washed twice with $H_2O$, and dried with $MgSO_4$ to give 2212 g of 94% (area percent by gas chromatography) the $R_F$-intermediate 4,5,5,5-tetrafluoro-4-(trifluoromethyl)-2-iodopentyl acetate.

Diethylene glycol (2944 g) and zinc powder (1330 g) can be placed into a 5 L 5-neck flask equipped with a simple distillation apparatus to form a mixture. This mixture can be stirred and heated to 120° C. and the 4,5,5,5-tetrafluoro-4-(trifluoromethyl)-2-iodopentyl acetate (4149 g) can be slowly added. As the 4,5,5,5-tetrafluoro-4-(trifluoromethyl)-2-iodopentyl acetate is added, the $R_F$-intermediate 4,5,5,5-tetrafluoro-4-(trifluoromethyl)pent-1-ene (2075 grains) can be flashed-off and collected in a 1 L ice trap. The contents of the ice trap can be distilled to give 4,5,5,5-tetrafluoro-4-(trifluoromethyl)pent-1-ene>99.5% (area percent by gas chromatography) (b.p. 54° C.).

The $R_F$-intermediate 4,5,5,5-tetrafluoro-4-(trifluoromethyl)pent-1-ene may also be prepared according to scheme (4) below.

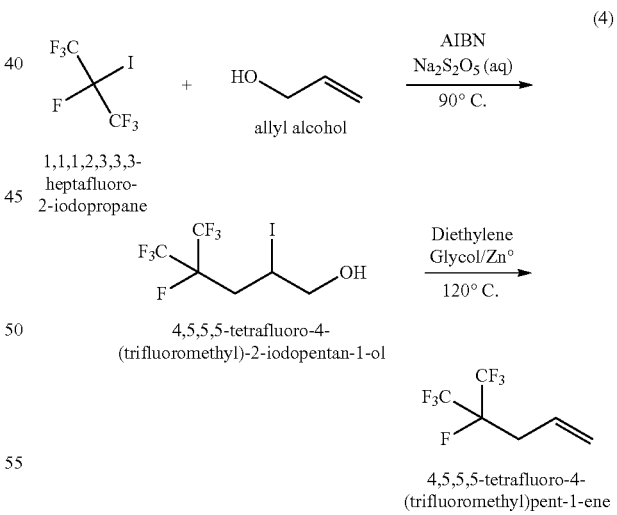

Referring to scheme (4) above, about 10.3 grains of 2-iodoheptafluoropropane can be added to a glass pressure tube. The tube can be sealed with a septa, heated to about 75° C. and 1.9 mL of 30% (wt/wt) aqueous $Na_2S_2O_5$ can be added to the tube via syringe through a septa to form a mixture within the tube. The mixture can be heated to about 80° C., and 0.07 grams of AIBN can be dissolved in allyl alcohol to form a solution. This solution can be slowly added to the tube through the septa to form another mixture. This other mixture can be agitated and maintained at a temperature of about 80° C. for 3 hours. The mixture can then be cooled and 11.2 grams of 4,5,5,5-tetrafluoro-4-(trifluoromethyl)-2-iodopentan-1-ol can be removed as an organic layer upon separation. The $R_F$-intermediate 4,5,5,5-tetrafluoro-4-(trifluoromethyl)-2-iodopentan-1-ol can have as much as a 93% (area percent by gas chromatography).

About 11 g of the $R_F$-intermediate 4,5,5,5-tetra fluoro-4-(trifluoromethyl)-2-iodopentan-1-ol can be added to a glass pressure tube and about 13 grams of 30% (wt/wt) aqueous acetic acid can be added to the other tube to form a mixture. The mixture can be heated to about 80° C., and 4 grams of powdered zinc can be added slowly through a solid addition system. The mixture can be allowed to stir for an additional 2 hours before being cooled and adding 2 mL of 1.5 N HCl to phase separate the mixture. The organic layer can be decanted to give 3 grains of the $R_F$-intermediate 4,5,5,5-tetrafluoro-4-(trifluoromethyl)pentan-1-ene which can be 75.14% (area percent by gas chromatography).

As another example, about 254 grams of diethylene glycol and 127.5 grams of Zn powder can be added into a 1000 mL three-neck round bottom flask equipped with a dean-stark apparatus, thermometer, and dip tube to form a mixture. The mixture can be heated to 120° C. while stirring and about 213.81 grams of the $R_F$-intermediate 4,5,5,5-tetrafluoro-4-(trifluoromethyl)-2-iodopentan-1-ol can be slowly pumped subsurface into the mixture. About 111.4 grams of the $R_F$-intermediate 4,5,5,5-tetrafluoro-4-(trifluoromethyl)pentan-1-ene collected which can be 88% (area percent by gas chromatography).

The $R_F$-intermediate 4,5,5,5-tetrafluoro-4-(trifluoromethyl)pent-1-ene can be prepared according to scheme (5) below.

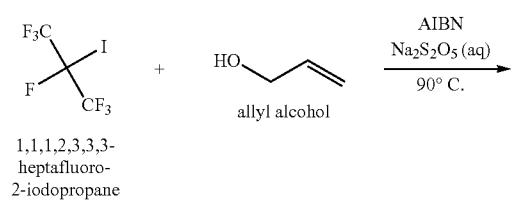

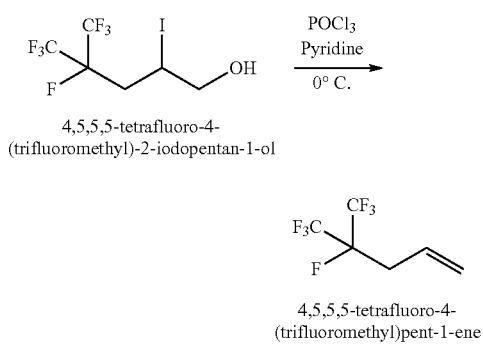

Referring to scheme (5) above, the $R_F$-intermediate 4,5,5,5-tetrafluoro-4-(trifluoromethyl)-2-iodopentan-1-ol may be prepared as described above and converted according to scheme (6) below.

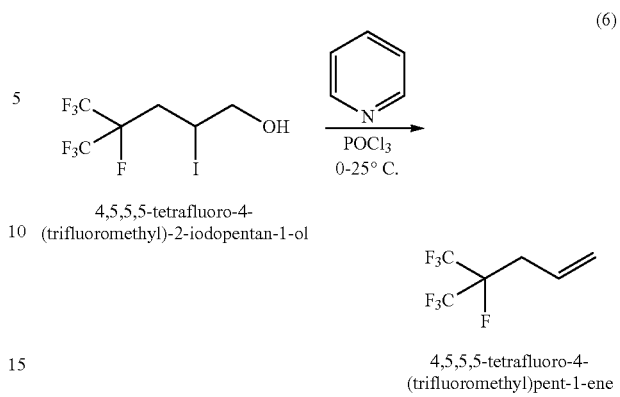

Referring to scheme (6) above, 4,5,5,5-tetrafluoro-4-(trifluoromethyl)-2-iodopentan-1-ol (11.42 g, 0.032 mole) and pyridine (84.17 g, 1.06 mole) can be added to a 250 mL two-neck round bottom flask equipped with a thermocouple, magnetic stir bar, heating mantle, and a 50 mL pressure equalizing addition funnel containing phosphorus oxychloride (2.23 g, 0.015 mole) to form a mixture. The mixture can be chilled to between 0° C.-5° C., and POCl$_3$ can be added drop-wise over a 25 minute period. A color change of the reaction mixture from yellow to dark red and an exotherm can be observed. The mixture can be allowed to warm to room temperature and then held overnight. Portions of the mixture can be drawn, washed in H$_2$O, and dried over MgSO$_4$, then analyzed by gas chromatography and/or gas chromatography/mass spectrometry.

Gas chromatography, gas chromatography/mass spectrometry and $^1$H NMR can be utilized to determine the 4,5,5,5-tetrafluoro-4-(trifluoromethyl)pent-1-ene.

The $R_F$-intermediate 4,5,5,5-tetrafluoro-4-(trifluoromethyl)pent-1-ene can be used to prepare other $R_n$-intermediates as well. For example, and by way of example only, 4,5,5,5-tetrafluoro-4-trifluoromethyl)pent-1-ene can be halogenated to form $R_F$-intermediates that include at least two CF$_3$— groups and a halogen other than fluorine, such as the $R_F$-intermediate 5-bromo-1,1,1,2-tetrafluoro-2-(trifluoromethyl)pentane according to scheme (7) below.

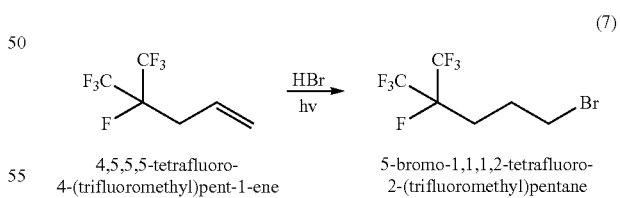

Referring to scheme (7) above, about 45 g (0.214 mole) of 4,5,5,5-tetrafluoro-4-(trifluoromethyl)pent-1-ene can be loaded into a 50 mL auto syringe and vaporized in a heated coil prior to being fed into a quartz tube via a Claisen adaptor, which terminates into a 250 mL two-neck round bottom flask equipped with an HBr scrubber containing a 10% (wt/wt) KOH solution. The quartz tube can be equipped with an internal thermocouple and a dry ice and acetone reflux condenser, and surrounded by an ultra violet light (254 nm) carousel. Simultaneous to the 4,5,5,5-tetrafluoro-4-(trifluoromethyl)pent-1-ene addition, anhydrous HBr can be fed into the quartz tube from a regulated tank through the same Claisen adaptor. Feed rates for HBr and 4,5,5,5-tetrafluoro-4-(trifluoromethyl)pent-1-ene can be set at 39.3 g/hour and 13.4 g/hour, respectively. About 53.94 g (0.19 mole) of product can be collected and washed with NaHCO$_3$ then washed with H$_2$O and dried over molecular sieves. Samples of the product can be drawn for gas chromatography/mass spectrometry analysis (m/z 290.8 (M$^+$), 209.0 (M$^+$–HBr), 189.1 (M$^+$–101.9)).

As another example, the R$_F$-intermediate 7,8,8,8-tetrafluoro-7-(trifluoromethyl)oct-1-ene, prepared as described above, for example, can be used to prepare another R$_F$-intermediate including the R$_F$-intermediate such as 8-bromo-1,1,1,2-tetrafluoro-2-(trifluoromethyl)octane according to scheme (8) below.

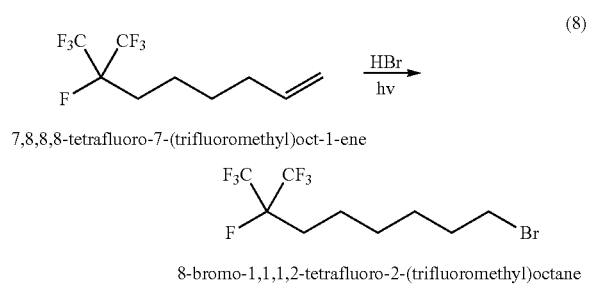

Referring to scheme (8) above, into a 250 mL pressure tube, equipped with a 9 inch Pen-Ray® Hg lamp, pressure gauge, agitator, and dip tube, can be added 67.06 grams (0.266 mole) of the R$_F$-intermediate 7,8,8,8-tetrafluoro-7-(trifluoromethyl)oct-1-ene. The tube can be sealed, the gaseous anhydrous HBr can be bubbled into the system, and the pressure maintained at about 184 kPa. The tube can be irradiated for 3 hours, and the mixture within the tube can be washed with NaHCO$_3$, then twice with water and dried over molecular sieves to yield about 68.89 grams (0.21 mole) of the R$_F$-intermediate 8-bromo-1,1,1,2-tetrafluoro-2-(trifluoromethyl)octane.

R$_F$-intermediates having alcohol functionality can be used as starting material to produce additional R$_F$-intermediates. For example, and by way of example only, a portion of the R$_F$-intermediate 4,5,5,5-tetrafluoro-4-(trifluoromethyl)-2-iodopentan-1-ol, described above, may be dehalohydrogenated. For example, R$_F$-intermediates such as the heterohalogenated compound 4,5,5,5-tetrafluoro-4-(trifluoromethyl)-2-iodopentan-1-ol that include at least two CF$_3$— groups and a halogen other than fluorine, may be dehalohydrogenated to form a homohalogenated alcohol. The dehalohydrogenating can include exposing the intermediate to tributyltin hydride, for example. According to an exemplary embodiment, the R$_F$-intermediate can include 4,5,5,5-tetrafluoro-4-(trifluoromethyl)-2-iodopentan-1-ol and the alcohol can include

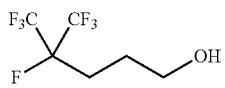

for example, according to scheme (9) below.

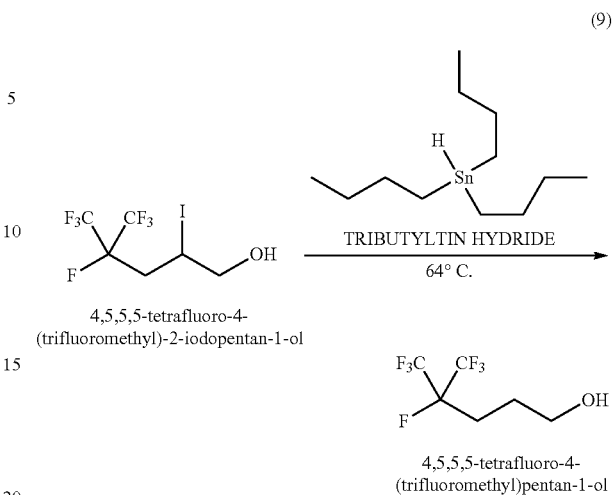

In accordance with scheme (9) above, a 500 mL two neck round bottom flask can be equipped with a thermocouple, agitator, and heating mantle. About 212.1 g (0.599 mole) 4,5,5,5-tetrafluoro-4(trifluoromethyl)-2-iodopentan-1-ol (212.1 g, 0.599 mole) can be added to the flask and heated to about 60° C. to 70° C. From a 100 mL pressure equalized addition funnel, about 196.4 g (0.675 mole) tributyltin hydride can be added drop-wise over a 4 hour period followed by 2 hours of continued heating and stirring. The R$_F$-intermediate 4,5,5,5-tetrafluoro-4(trifluoromethyl)pentan-1-ol can be obtained through vacuum distillation and verified by gas chromatography/mass spectrometry (m/z 228 (M$^+$), 211 (M$^+$–OH), 159 (M$^+$–CF3)).

Still another R$_F$-intermediate, e.g., 2,3,4,5,5,5-hexafluoro-2,4-bis(trifluoromethyl) Pentanol, may be prepared in accordance with the procedures described in scheme (10) below and detailed in U.S. Pat. No. 3,467,247, herein incorporated by reference.

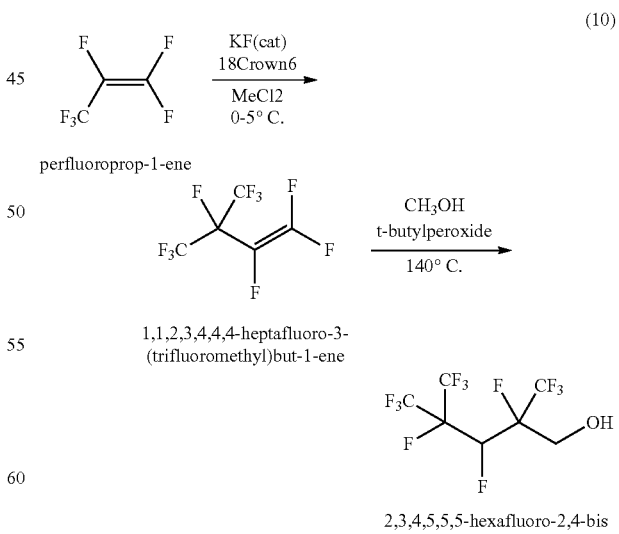

In accordance with an exemplary embodiment of the disclosure, a R$_F$-intermediate having alcohol functionality such as the 4,5,5,5-tetrafluoro-4-(trifluoromethyl)pentan-1-ol and/ or 2,3,4,5,5,5-hexafluoro-2,4-bis(trifluoromethyl)pentan-1-ol described above may be reacted with a halogenated olefin to form another $R_F$-intermediate such as an allyl-ether compound. As described above, the $R_F$-intermediate can include at least two $CF_3$— groups; at least one $(CF_3)_2CF$— group; and/or at least three $CF_3$— groups. Exemplary halogenated olefins include olefins that include a halogen other than fluorine such as bromine, for example. 3-bromoprop-1-ene may be used as a halogenated olefin. The halogenated olefin may be exposed to the alcohol in the presence of a basic solution, such as an aqueous KOH solution. In an exemplary embodiment, a mixture of the alcohol, the halogenated olefin, and a reactant media including a phase transfer catalyst, such as tetrabutylammonium hydrogen sulfate, may be prepared, and the basic solution can be added to this mixture while maintaining the mixture below at least 10° C. $R_F$-intermediates including the allyl ether compound

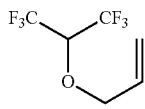

may be prepared by reacting the RF-intermediate 1,1,1,3,3,3-hexafluoropropan-2-ol with 3-bromoprop-1-ene in accordance with the above and scheme (11) below.

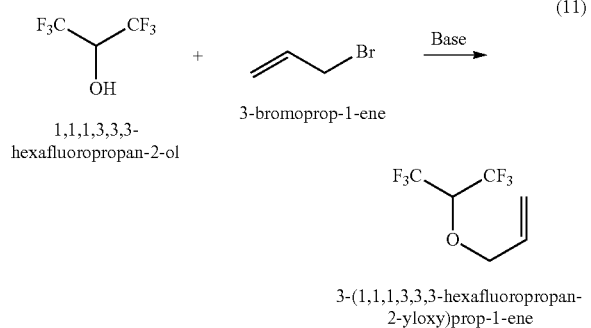

(11)

Referring to scheme (11) above, a 500 mL three-neck flask can be equipped with a thermometer, agitator, and a condenser. About 40.86 g of NaOH can be dissolved in 120 g of deionized H2O to form a mixture. To the mixture can be added about 170.1 grams of hexafluoroisopropan-2-ol. After about 15 minutes, 100.5 grams of 3-bromoprop-1-ene can be added to the mixture at room temperature. The mixture can be agitated for about 2 days. The mixture can then be phase separated to yield about 178.6 g of crude product

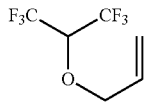

being about 92.4% area percent pure (by gas chromatography) with 3.2% area percent allyl bromide. The crude product can be distilled to yield a 99.94% (area percent by gas chromatography) 3-(1,1,1,3,3,3-hexafluoropropan-2-yloxy) prop-1-ene having a boiling point of 83.5° C.

By way of another example, halogenated intermediates including the allyl-ether compound

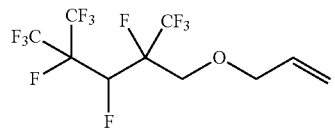

may be prepared by reacting the RF-intermediate 1,2,3,4,4,4-heptafluoro-2,4-bis-(trifluoromethyl)pentane-1-ol with 3-bromoprop-1-ene in accordance with scheme (9) and scheme (12) below.

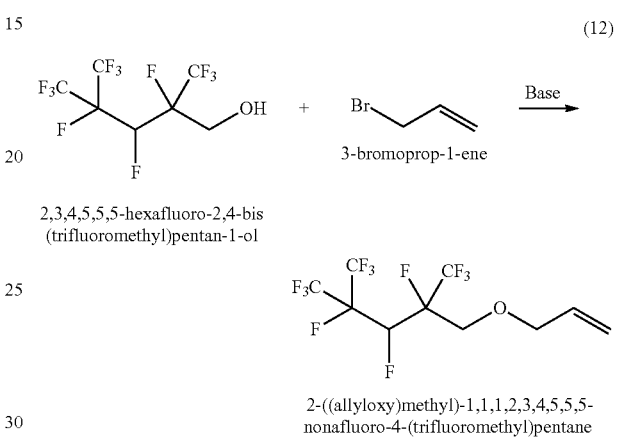

(12)

Referring to scheme (12) above, into a 1 L three-neck flask can be added 2,3,4,5,5,5-hexafluoro-2,4-bis(trifluoromethyl)pentan-1-ol (551 g, 1.66 mole), allyl bromide (221.2 g, 1.83 mole) and tetrabutylammonium hydrogen sulfate (5 mole %) to form a mixture. The mixture can be chilled to about 10° C. and 50% (wt/wt) KOH (400 grams) can be added over a 2 hour period. The mixture can then be allowed to stir at 10° C. for about 72 hours. After the 72 hours, an additional 100 mL of 33% (wt/wt) KOH can be added, and the mixture can be agitated for an additional 12 hours. The reaction can be monitored by removing portions and analyzing, using gas chromatography, and after nondetection of 2,3,4,5,5,5-hexafluoro-2,4-bis(trifluoromethyl)pentan-1-ol, the mixture can be washed one time with $H_2O$, twice with 10% (wt/wt) HCl, and one more time with $H_2O$. The combined organic layers can be dried with $MgSO_4$ to give about 516 grams of material containing 20.04 grams of 2,3,4,5,5,5-hexafluoro-2,4-bis(trifluoromethyl)pentyl allyl ether having a 28.21% (area percent by gas chromatography).

According to another embodiment of the disclosure, $R_F$-intermediate including the homohalogenated alcohol, such as 4,5,5,5-tetrafluoro-4-(trifluoromethyl)pentan-1-ol described above, may be reacted to form an acrylate. The homohalogenated alcohol can be exposed to an acryloyl compound, for example, to form the acrylate. In an exemplary embodiment, the homohalogenated alcohol can include 1,1,1,3,3,3-hexafluoropropan-2-ol and the acryloyl compound can include acryloyl chloride. The 1,1,1,3,3,3-hexafluoropropan-2-ol can be reacted with the acryloyl chloride in the presence of a basic solution while maintaining the temperature of the solution at about 0° C. to form the $R_F$-intermediate 1,1,1,3,3,3-hexafluoropropan-2-yl acrylate, for example, according to scheme (13) below.

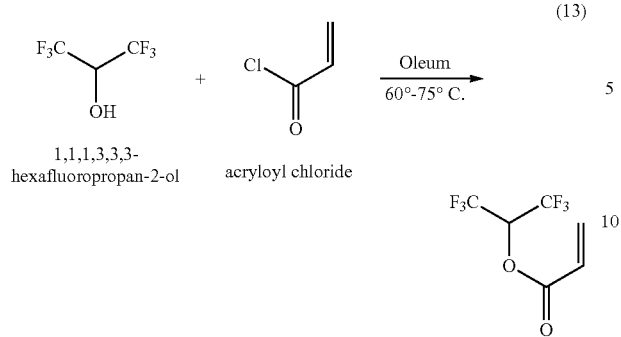

With reference to scheme (13) above, a 1000 mL three-neck flask can be equipped with a thermometer, agitator, and dropping funnel with a dip tube. Into the flask can be added about 130.6 grams of acryloyl chloride, 168.8 grams 1,1,1,3,3,3-hexafluoropropan-2-ol, and 1 grain of 2,6-di-tert-butyl-4-methylphenol to form a mixture. About 30% (wt/wt) oleum can then be added to the mixture through the dip tube while maintaining the mixture at 60° C.-75° C. After addition, the mixture can be maintained at 60° C.-70° C. for about 4 hours. Single stage vacuum distillation of the mixture can yield about 183 grains of crude product 1,1,1,3,3,3-hexafluoropropan-2-yl acrylate being about 95.7% (area percent by as chromatography). The crude 1,1,1,3,3,3-hexafluoropropan-2-yl can be distilled further to increase purity to 99.7% (area percent by gas chromatography).

By way of another example, the halogenated intermediate including the homohalogenated alcohol, such as 4,5,5,5-tetrafluoro-4-(trifluoromethyl)pentan-1-ol described above, may be reacted to form an acrylate. The 4,5,5,5-tetrafluoro-4-(trifluoromethyl)pentan-1-ol can be exposed to acryloyl chloride according to scheme (14) below to form

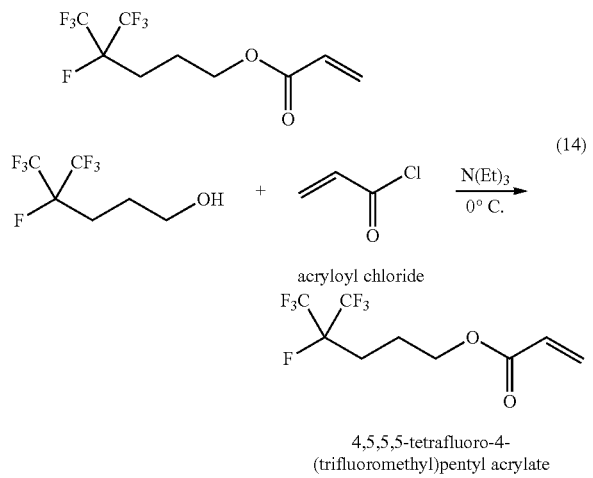

With reference to scheme (14) above, 4,5,5,5-tetrafluoro-4-(trifluoromethyl)pentan-1-ol (2.59 g, 0.011 mole) and triethylamine (1.3 g, 0.013 mole) can be added to a 15 mL three-neck round bottom flask equipped with a water cooled reflux condenser, thermocouple, agitator, and addition funnel, to form a mixture. The mixture can be maintained at about 0° C. using an ice water bath. Acryloyl chloride (1.38 grams, 0.015 mole) can be added to the mixture through an addition funnel drop-wise over about 15 minutes. After about a 1 hour hold period, 10 mL $H_2O$ can be added to the flask, two phases can be observed, and the organic phase separated. The organic phase can be analyzed and a peak observed and confirmed to have a m/z of 283 by gas chromatography/mass spectrometry.

By way of another example, a $R_F$-intermediate can be prepared by reacting an alcohol having at least two $CF_3$— groups and a cyclic group such as 3,5-bis(trifluoromethyl)benzyl alcohol to form an acrylate. The alcohol can be reacted with an acryloyl compound such as acryloyl chloride to form the acrylate. In an exemplary embodiment, the acrylate can include

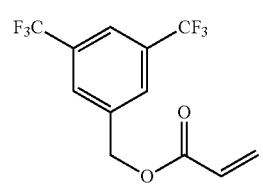

For example, and by way of example only, 200 mL of $CH_2Cl_2$ and 25 grams of 3,5-bis(trifluoromethyl)benzyl alcohol can be placed in a 500 mL flask to form a mixture. While stirring the mixture, about 13.8 grains of triethylamine can be added to the mixture. The mixture can then be cooled down in an ice bath and 10.5 mL acryloyl chloride can slowly be added to the mixture. The mixture can then be stirred for about an hour and then quenched with an aqueous HCl solution. The mixture can be allowed to phase separate and the organic layer can be washed with saturated KCl solution and dried over MgSO4. The organic solvent can be removed by evaporation and the remaining 25.16 grams of solid

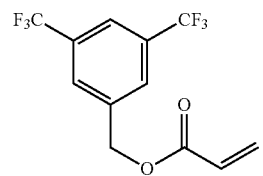

can be >98% (area percent by gas chromatography).

$R_F$-intermediates having a cyclic group can also be prepared. According to an exemplary embodiment, one reactant including at least two $CF_3$— groups such as a heterohalogenated intermediate can be reacted with another reactant including a cyclic group, such as phenol, to form a $R_F$-intermediate that includes at least two $CF_3$— groups and a cyclic group. The one reactant can include an alcohol such as the 4,5,5,5-tetrafluoro-4-(trifluoromethyl)-2-iodopentan-1-ol prepared above. For example, and by way of example only, the $R_F$-intermediate can be prepared according to scheme (15) below.

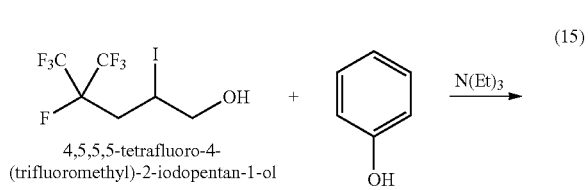

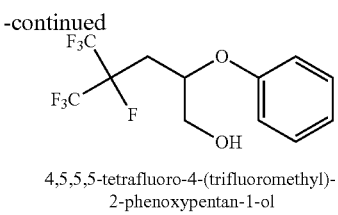

4,5,5,5-tetrafluoro-4-(trifluoromethyl)-
2-phenoxypentan-1-ol

Referring to scheme (15) above, about 3.9 grams (0.04 mole) of phenol and 5.5 grams (0.05 mole) of triethylamine can be placed into a clean and dry 25 mL two-neck round bottom flask equipped with an agitator, thermocouple, heating mantle, and a 50 mL pressure equalizing addition funnel containing 4.7 grams (0.042 mole) 4,5,5,5-tetrafluoro-4-(trifluoromethyl)-2-iodopentan-1-ol to form a mixture. The mixture can be gradually warmed to 68° C. and then 4,5,5,5-tetrafluoro-4-(trifluoromethyl)-2-iodopentan-1-ol can be added drop-wise over 30 minutes. Yield of

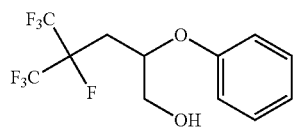

can be 42%. (m/z 320.1 (M+), 94 (M+−226)).

By way of another example, a $R_F$-intermediate can be prepared that is heterohalogenated and contains a cyclic group according to scheme (16) below.

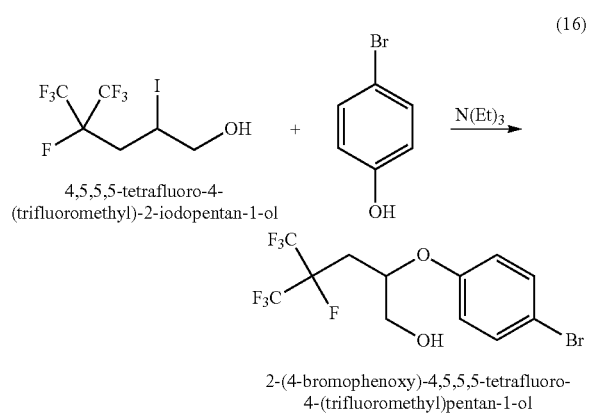

2-(4-bromophenoxy)-4,5,5,5-tetrafluoro-
4-(trifluoromethyl)pentan-1-ol

Referring to scheme (16) above, about 13.7 grams (0.079 mole) of 4-bromophenol and 9.0 grams (0.089 mole) of triethylamine can be added to a 50 mL 2-neck round bottom flask equipped with a thermocouple, agitator, heating mantle, and a 50 mL pressure equalizing addition funnel. Contents of the round bottom flask can be gradually heated to 93° C. followed by drop-wise addition of 4,5,5,5-tetrafluoro-4-(trifluoromethyl)-2-iodopentan-1-ol (23.1 g, 0.065 mole) using the addition funnel over 15 minutes. Contents can then be refluxed for 1 hour then sampled and analyzed by gas chromatography. Yield by gas chromatography determination can be 43% for the 2-(4-bromophenoxy)-4,5,5,5-tetrafluoro-4-(trifluoromethyl)pentan-1-ol.

According to another embodiment of the disclosure, bicyclic halogenated intermediates can be prepared according to schemes (17A and B) below.

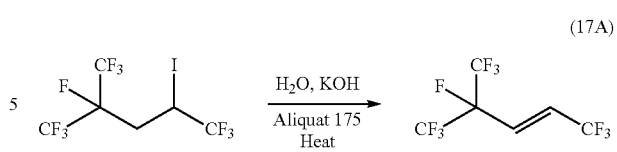

Referring to scheme (17A) above, to a three-neck 500 mL flask equipped with an agitator, an inlet for a starting material addition, and a packed column topped with a reflux distillation head, thermocouple, and collection flask can be charged 60.40 g of KOH (0.917 mole), 5.86 g of Methyltributylammonium chloride (Aliquat 175, ~5% by wt) in 150 mL of deionized water to form a solution. The resulting solution can be heated 97° C. and 110 g (0.281 mole) 1,1,1,2,5,5,5-heptafluoro-2-(trifluoromethyl)-4-iodopentane can be added drop-wise and sub-surface via syringe pump over the course of 2 hr period. During this addition the resulting product can be collected in the overhead collection flask and the reaction can be continued to be heated until the overhead temperature reached 94° C. The collected material can be dried over magnesium sulfate to give 74.18 g of crude reaction product which by GC analysis consisted on primary product and starting material. The crude reaction material was distilled to afford 42.6 g of (E)-1,1,1,4,5,5,5-heptafluoro-4-(trifluoromethyl)pent-2-ene (57.5% isolated yield). (1H-NMR (CDCl3): ☐ 6.45 (d, J=12 Hz, 1H), 6.45 (dhep, 1H).

13C-NMR (CDCl3): 90.5 (dhep. J=27, 202 Hz, CFCH), 120 (qd, 27, 287 Hz, CF3CF), 121.6 (q, J=220 Hz, CHCF3), 124.4 (m, CHCF), 128.2 (qd, J=21, 36 Hz, CHCF3). 19F-NMR (CDCl3w/CCl3F): ☐ −66.4 (d, JH-F=3 HzCF3CH), −76.9 (d, JF-F=8 Hz, CF3CF), −186.9 (m, CF3CF).

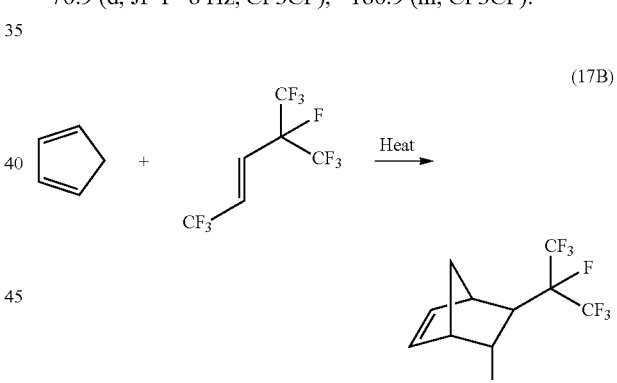

Referring to scheme (17B) above, 5.26 grams (0.08 mole) cyclopentadiene and 14.67 grams (0.06 mole) (E,Z)-1,1,1,4,5,5,5-heptafluoro-4-(trifluoromethyl)pent-2-ene can be added to form a mixture in a stainless steel autoclave that can be equipped with a 6.9×10³ kPa rupture disc, agitator, external thermocouple, valve, and pressure gauge. The mixture can be maintained at about 140° C. to 230° C. under autogeneous pressure for about 4 to 72 hours. 5-(trifluoromethyl)-6-(perfluoropropan-2-yl)bicycle[2.2.1]hept-2-ene yields can be greater than 12 (area percent by as chromatography). Reaction sample can also be analyzed by gas chromatography/mass spectroscopy. (m/z 330 (M⁺), 261 (M⁺−CF₃), 161 (M⁺−(CF₃)₂CF)).

Figure 4:
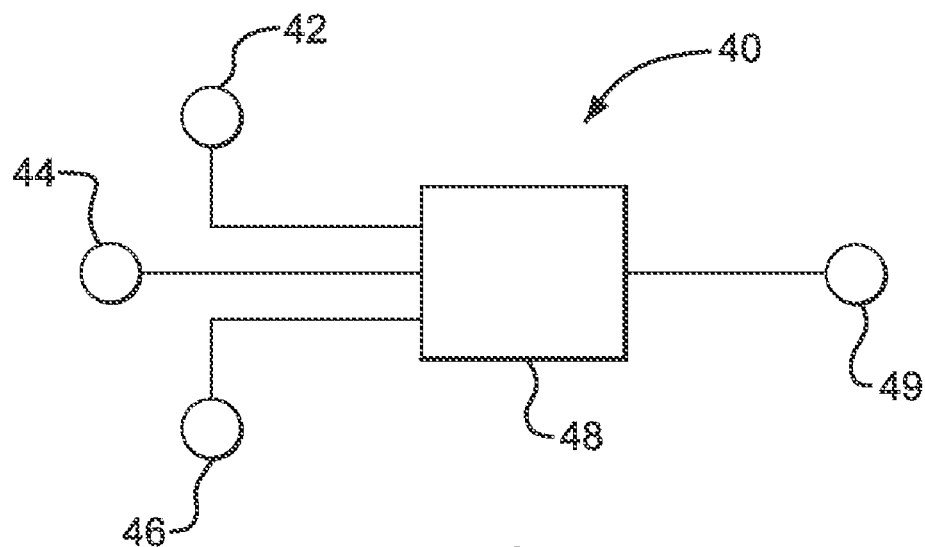
FIG. 4 is an exemplary system for preparing compositions according to an embodiment.

Referring to FIG. 4, a system 40 is shown for preparing $R_F$-intermediates that includes reagents such as a taxogen 42, a telogen 44, and an initiator 46 being provided to a reactor 48 to form a product such as a telomer 49. In exemplary embodiments, system 40 can perform a telomerization process. According to an embodiment, taxogen 42 can be exposed to telogen 44 to form telomer 49. In accordance with another embodiment, taxogen 42 can be exposed to telogen 44 in the presence of initiator 46. Reactor 48 can also be configured to provide heat to the reagents during the exposing.

Taxogen 42 can include at least one $CF_3$-comprising compound. The $CF_3$-comprising compound can have a C-2 group having at least one pendant $CF_3$— group. In exemplary embodiments, taxogen 42 can include an olefin, such as trifluoropropene. Taxogen 42 can also include 4,5,5,5-tetrafluoro-4-(trifluoromethyl)pen-1-tene and/or 6,7,7,7-tetrafluoro-6-(trifluoromethyl)hept-1-ene, for example.

Telogen 44 can include halogens such as fluorine and/or chlorine. Telogen 44 can include at least four fluorine atoms and can be represented as $R_F$-Q and/or $R_{Cl}$-Q. The $R_F$ can be as described above and can include at least four fluorine atoms, and the Q group can include one or more atoms of the periodic table of elements. The Q group can be H or I with the $R_F$ group being $(CF_3)_2CF$— and/or —$C_6F_{13}$, for example. $R_F$-Q can be 2-iodofluoropropane, for example. The $R_{Cl}$ group can include at least one —$CCl_3$ group. Exemplary telogens can include the halogenated compounds described above, such as $(CF_3)_2CFI$, $C_6F_{13}I$, and/or trichloromethane. In exemplary embodiments, taxogen 42 can include trifluoropropene and telogen 44 can include $(CF_3)_2CFI$, with a mole ratio of taxogen 42 to telogen 44 being from about 0.2:1 to about 10:1, from about 1:1 to about 5:1, and/or from about 2:1 to about 4:1. Taxogen 42 can include 4,5,5,5-tetrafluoro-4-(trifluoromethyl)pen-1-tene and/or 6,7,7,7-tetrafluoro-6-(trifluoromethyl)hept-1-ene, and telogen 44 can include $(CF_3)_2CFI$, for example.

Reactor 48 can be any lab-scale or industrial-scale reactor and, in certain embodiments, reactor 48 can be configured to control the temperature of the reagents therein. According to exemplary embodiments reactor 48 can be used to provide a temperature during the exposing of the reagents of from about 90° C. to about 180° C., 60° C. to about 220° C. and/or 130° C. to about 150° C. and, according to other embodiments, reactor 48 can be configured to maintain the temperature of the reagents at about 90° C.

Telomer 49, produced upon exposing taxogen 42 to telogen 44, can include $R_F(R_T)_nQ$ and/or $R_{Cl}(R_T)_nH$. The $R_T$ group can include at least one C-2 group having a pendant group that includes at least one $CF_3$ group, such as

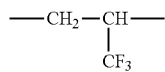

Exemplary telomers 49 can include

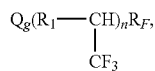
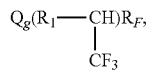
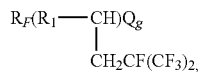

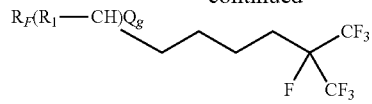

and/or one or both of

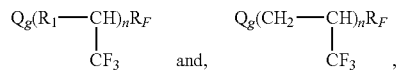

with $R_F$ including at least one carbon atom, such as —CH2-, for example. In exemplary embodiments, n can be at least 1 and in other embodiments n can be at least 2 and the product can include one or more of

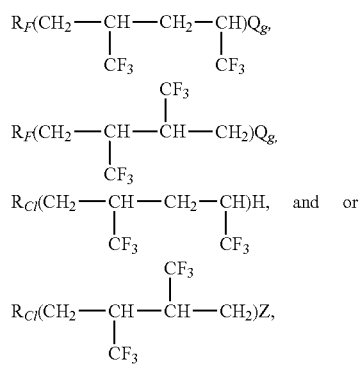

Z being H, Br, and or Cl, for example.

In an exemplary embodiment, the taxogen trifluoropropene can be exposed to the telogen $(CF_3)_2CFI$ to form the telomer

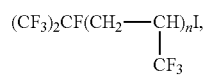

and, by way of another example, trifluoropropene can be exposed to the telogen $C_6F_{13}I$ to form the telomer

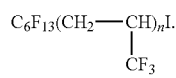

In accordance with another embodiment, the taxogen trifluoropropene can also be exposed to the telogen $CCl_3H$ to form the telomer

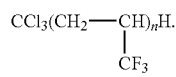

Products having n being at least 2 can be formed when utilizing an excess of the taxogen as compared to the telogen. For example, at least a 2:1 mole ratio of the taxogen to the telogen can be utilized to obtain products having a being at least 2. For example, and by way of example only, at least two moles of the taxogen trifluoropropene can be exposed to at least one mole of the telogen (CF$_3$)$_2$CFI to form one or both of the

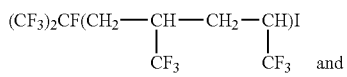

and

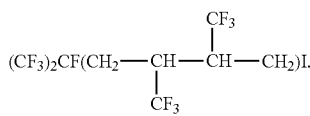

In additional embodiments, initiator 46 may be provided to reactor 48 during the exposing of the reagents. Initiator 46 can include thermal, photochemical (UV), radical, and/or metal complexes, for example, including a peroxide, such as di-tert-butyl peroxide, initiator 66 can also include catalysts, such as Cu. Initiator 46 and taxogen 42 can be provided to reactor 48 at a mole ratio of initiator 46 to taxogen 42 of from between about 0.001 to about 0.05 and/or from between about 0.01 to about 0.03, for example. Initiator 46 and taxogen 42 can be provided to reactor 48 at a mole ratio of initiator 46 to taxogen 42 of from between about 0.001 to about 0.05 and/or from between about 0.01 to about 0.03, for example According to exemplary embodiments, various initiators 46 and telogens 44 can be used to telomerize taxogen 42 as referenced in Table 2 below. Telomerizations utilizing photochemical and/or metal-complex initiators 46 can be carried out in batch conditions using Carius tube reactors 48. Telomerizations utilizing thermal, peroxide and/or metal complex initiators 46 can be carried out in 160 mL and/or 500 mL Hastelloy® reactors 48. Telogen 44 (neat and/or as a peroxide solution) can be provided as a gas at a temperature from about 60° C., to about 180° C. and a telogen 44 [T]$_0$/taxogen 42 [Tx]$_0$ initial molar ratio R$_0$ can be varied from 0.25 to 3.0 and the reaction time from 2 to 22 hrs. The product mixture can be analyzed by gas chromatography and/or the product can be distilled into different fractions and analyzed by $^1$H and $^{19}$F NMR and/or $^{13}$C NMR. Mono-adduct (n=1) and di-adduct (n=2) products can be recognized as shown in Table 2 below.

For example, and by way of example only, the taxogen trifluoropropene can be combined with the telogen 2-iodofluoropropane to form the telomer 1,1,1,2,5,5,5-heptafluoro-2-(trifluoromethyl)-4-iodopentane according to scheme (18) below.

(18)

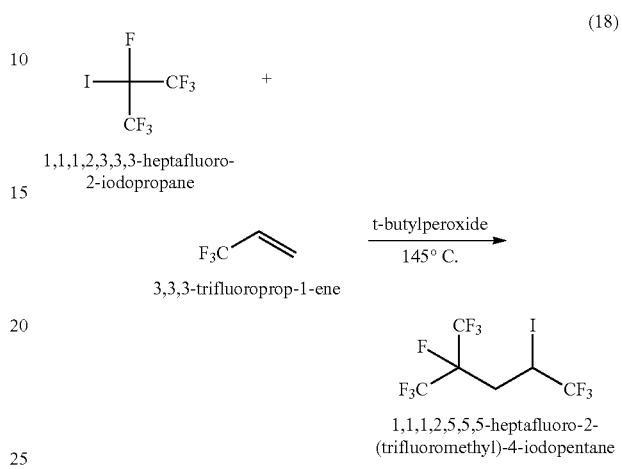

As another example, the telogen 1,1,1,2,2,3,3,4,4,5,5,6,6-tridecafluoro-6-iodohexane can be combined with the taxogen trifluoropropene to form the telomer 1,1,1,2,2,3,3,4,4,5,5,6,6,9,9,9-hexadecafluoro-8-iodononane according to scheme (19) below.

(19)

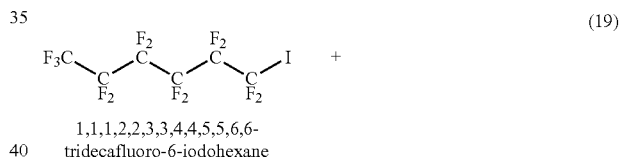

1,1,1,2,2,3,3,4,4,5,5,6,6-tridecafluoro-6-iodohexane

TABLE 2

Telomerization of Trifluoropropene Taxogen

| | | | | | | P (bars) | | % Conv. of | Yield (%) by GC$^c$ | | |
| | | | | | | | | | | MonoAdduct | DiAdduct |
| Run$^a$ | Init.$^d$ | R$_0$$^b$ | C$_0$$^b$ | T (° C.) | t$_r$ (hrs) | max | min | Taxogen | Telogen | (n = 1) | (n = 2) |
|---|---|---|---|---|---|---|---|---|---|---|---|
| 1 | Therm | 0.50 | — | 160 | 20 | 22 | 17 | 79.2 | 27.6 | 51.9 | 20.5 |
| 2 | Therm | 0.25 | — | 160 | 20 | 39 | 34 | 36.8 | 52.8 | 26.2 | 21 |
| 3 | Therm | 0.50 | — | 180 | 22 | 30 | 11 | 73.4 | 2.4 | 65.9 | 31.2 |
| 4 | Perk | 0.50 | 0.03 | 62 | 20 | 7 | 5 | 79.2 | 23.8 | 35.4 | 40.8 |
| 5 | AIBN | 0.50 | 0.03 | 82 | 18 | 10 | 7 | 79.2 | 17.4 | 38.8 | 42 |
| 6 | TRIG | 0.50 | 0.03 | 134 | 6 | 16 | 0.6 | 89.6 | 3.7 | 19 | 63.8 |
| 7 | DTBP | 0.50 | 0.03 | 140 | 6 | 17 | 0.2 | 97.9 | 3.7 | 19 | 63.8 |
| 8 | DTBP | 0.50 | 0.03 | 143 | 4 | 19 | 0.8 | 94.3 | 9.6 | 21 | 66.6 |
| 9 | DTBP | 1.4 | 0.03 | 150 | 4 | 13 | 1.1 | 95.2 | 22.5 | 54.4 | 15.7 |
| 10 | DTBP | 0.75 | 0.03 | 145 | 4 | 20 | 3.0 | 93.8 | 6.8 | 34.1 | 49.0 |
| 11 | DTBP | 1.2 | 0.03 | 150 | 4 | 20 | 5.0 | 90.0 | 14.9 | 46.3 | 33.4 |
| 12 | DTBP | 1.4 | 0.03 | 150 | 4 | 21 | 3.5 | 95.0 | 12.6 | 54.1 | 28.6 |
| 13 | DTBP | 1.5 | 0.03 | 150 | 4 | 19 | 5.0 | 95.0 | 24.6 | 43.9 | 28.3 |

$^a$Telogen can be C$_6$F$_{13}$I in Runs Nos 1-9 and (CF$_3$)$_2$CFI in Runs No 10-13
$^b$R$_0$ = [T]$_0$/[Tx]$_0$; C$_0$ = [In]$_0$/[Tx]$_0$
$^c$Heavy TFP telomers (n > 2) can make up remainder of product
$^d$Initiators can be Perk. 16s(t-butyl cyclohexyl dicarbonate); AIBN; Trig.101 (2,5-bis-(t-butyl peroxy)-2,5-dimethylhexane); and DTB

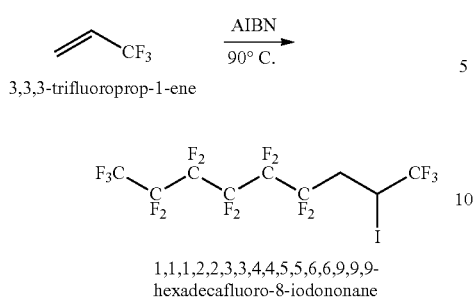

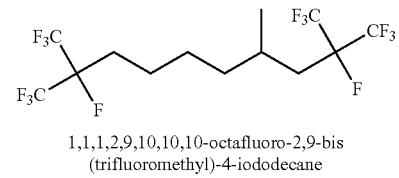

As another example, a taxogen including at least two CF$_3$— groups such as the RF-intermediates 4,5,5,5-tetrafluoro-4-(trifluoromethyl)pen-1-tene and/or 6,7,7,7-tetrafluoro-6-(trifluoromethyl)hept-1-ene can be combined with a telogen including a saturated compound having at least two CF$_3$— groups to form a telomer including a saturated compound according to scheme (20) below.

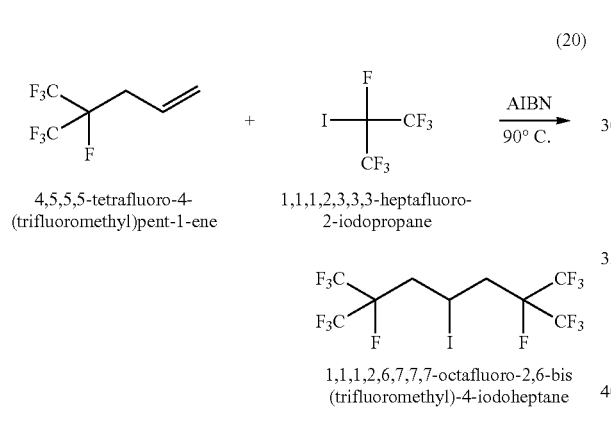

Referring to scheme (20) above, 3-perfluoroisopropyl-1-propene (20 grams, 0.095 mole) and 2-iodoheptafluoropropene (28.18 grams, 0.095 mole) can be provided to a glass pressure tube to form a mixture. To this mixture AIBN (0.51 grams) can be added, and the mixture can be heated to and maintained at 85° C. for 24 hours. During heating, additional AIBN can be added (0.11 grams after 3 hours and another 0.1 grams after 21 hours). The mixture can then be washed twice with H2O and analysis via gas chromatography can yield a 56% area percent purity.

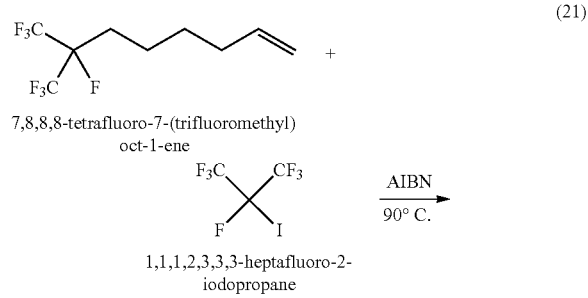

Referring to scheme (21) above, to a sealed and evacuated 250 mL stainless steel autoclave equipped with dip tube and valve, pressure gauge, rupture disk, vent valve, agitator, and a thermocouple, 30.4 grains (0.121 mole) 6,7,7,7-tetrafluoro-6-(trifluoromethyl)hept-1-ene, 41.32 grams (0.140 mole) heptafluoro-2-iodopropane, and 0.209 grams (0.0013 mole) 2,2'-azobisisobutrylonitrile can be added to form a mixture. The mixture can then be slowly heated to 90° C. and held for 24 hours. After the hold period, samples can be drawn and analyzed by gas chromatography and gas chromatography/mass spectrometry. (GC-HP-5 column (RT: 15.9 min), GC/MS (m/z 421 (M$^+$–I), 211 (M$^+$–C$_6$H$_5$F$_7$I), 127 (I$^+$)).

According to additional embodiments, R$_F$-intermediates, including the telomers, can be further modified to form additional R$_F$-intermediates. For example, and by way of example only, the R$_F$-intermediate 1,1,1,2,5,5,5-heptafluoro-2-(trifluoromethyl)-4-iodopentane can be modified according to scheme (22) below to produce additional intermediates as shown below.

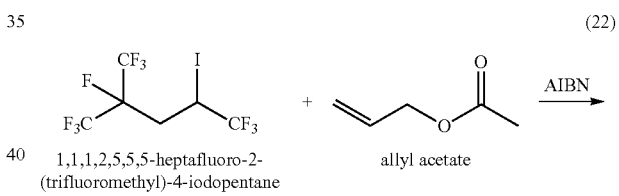

With reference to scheme (22) above, a 500 mL three-neck flask can be equipped with an agitator, thermocouple, reflux condenser, and septa. About 483 grams (1.23 mole) 1,1,1,2,5,5,5-heptafluoro-2-(trifluoromethyl)-4-iodopentane can be added to the flask. About 12.4 grams (0.08 mole) AIBN can be added to a syringe pump containing about 123 grams (1.23 mole) allyl acetate to form a mixture. The syringe pump can be connected to the flask via a Teflon tube fed through the septa. The 1,1,1,2,5,5,5-heptafluoro-2-(trifluoromethyl)-4-iodopentane can be maintained at about 80° C. to 90° C. The allyl acetate and AIBN mixture in the syringe pump can be charged (fed) into the flask at a rate of 15 mL per hour. The mixture can be sampled and analyzed by gas chromatography to find 6,7,7,7-tetrafluoro-4,6-bis(trifluoromethyl)-2-iodoheptyl acetate having about 78.3% area percent purity.

(23)

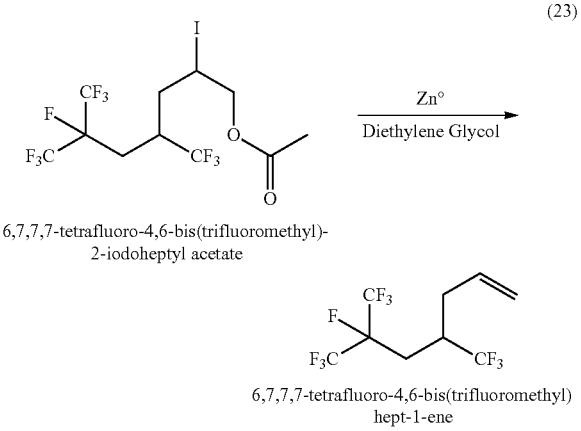

6,7,7,7-tetrafluoro-4,6-bis(trifluoromethyl)-
2-iodoheptyl acetate 6,7,7,7-tetrafluoro-4,6-bis(trifluoromethyl)
hept-1-ene With reference to scheme (23) above, a three-neck 250 mL flask can be equipped with a thermocouple, agitator, 50 mL pressure equalizing addition funnel, and a short path distillation apparatus. About 150 grams of diethylene glycol and 26.01 grams (0.4 mole) zinc can be added to the flask to form a mixture. The mixture can be maintained at about 50° C. to 65° C. and a vacuum can be maintained at about 5.3 kPa to 8.7 kPa. About 33 grams (0.067 mole) 6,7,7,7-tetrafluoro-4,6-bis (trifluoromethyl)-2-iodoheptyl acetate can be placed into the 50 mL addition funnel and added drop-wise over about 1 hour. Approximately, in concert to the 6,7,7,7-tetrafluoro-4, 6-bis(trifluoromethyl)-2-iodoheptyl acetate addition, 6,7,7,7-tetrafluoro-4,6-bis(trifluoromethyl)hept-1-ene can be reactively distilled and collected in a 50 mL receiver flask. A total of about 39.7 grams of the crude $R_F$-intermediate 6,7,7,7-tetrafluoro-4,6-bis(trifluoromethyl)hept-1-ene can be collected having 53% area percent purity by gas chromatography.

Figure 5:
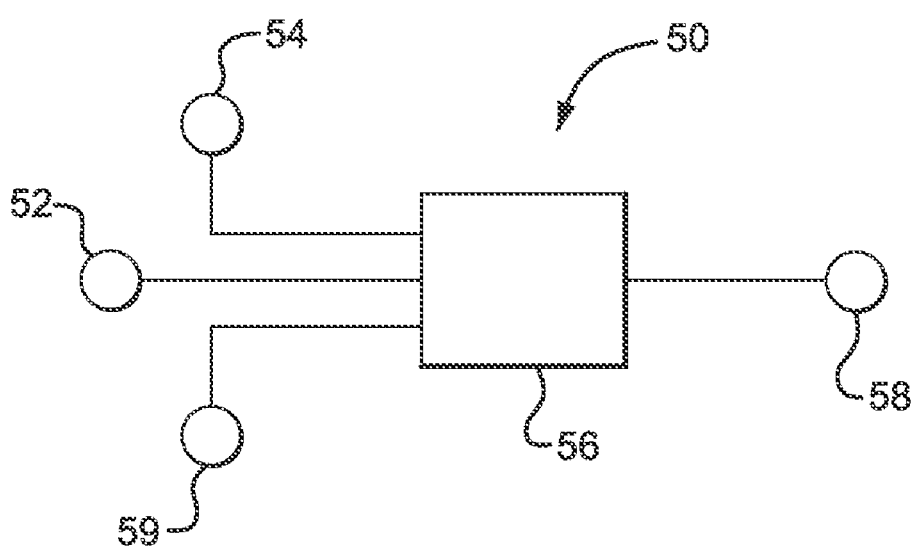
FIG. 5 is an exemplary system for preparing compositions according to an embodiment.

Referring to FIG. 5, a system 50 is shown that can be utilized for the production of telomers that include ester functionality. System 50 can include a reactor 56 that is configured to receive reagents such as an ester 54 and a telomer 52, as well as, in other embodiments, an initiator 59. Telomer 52 can be fluorinated and can be represented by the general formula $Q_1(R_T)_nQ_2$. The $Q_1$ and $Q_2$ groups can include one or more atoms of the periodic, table of elements including Q and/or $Q_g$ and according to exemplary embodiments. The $Q_1$ and $Q_2$ groups need not be different nor need they be identical. The $Q_1$ group, in exemplary embodiments, can include at least one —$CF_3$ group, and in other embodiments at least two —$CF_3$ groups. The $Q_1$ group can also include a —$CF(CF_3)_2$ group in one embodiment and a —$C_6F_{13}$ group in other embodiments. The $Q_2$ group can include halogens in certain embodiments and in other embodiments can include hydrogen. Telomer 52 can include $R_F$-intermediates including telomer 49 described above, such as

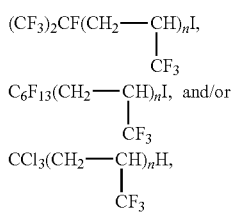

for example. Ester 54 can include an allyl-comprising compound such as allyl acetate.

According to an additional embodiment, initiator 59 can be utilized within reactor 46 during the exposing of ester 54 to telomer 52. Initiator 29 can include compounds such as azobisisobutyronitrile (AIBN), peroxides such as: dibenzoyl peroxide, tert-amyl peroxypivalate, tert-butyl peroxypivalate, DTBP (di-tert-butyl peroxide), and/or a metal complex such as copper chloride, ferric chloride, palladium and/or ruthenium complexes can also be used.

Ester 54 can be exposed to telomer 52 to form an ester-comprising telomer 58. Ester-comprising telomer 58 can include the composition $Q_1(R_T)_nR_E$, with the $R_E$ group including at least one ester group and/or $Q_g$, such as an acetate group. In exemplary embodiments, telomer 52 can include the formula. $R_F(R_T)_nQ_2$, with the $R_F$ group including at least one fluorine atom such as a —$CF_3$ group and/or as described above. $R_F(R_T)_nQ_2$ can be exposed to ester 54 to form an ester-comprising telomer 58 such as $R_F(R_T)R_E$, for example. In accordance with an embodiment, the telomere

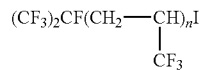

can be exposed to the ester allyl acetate to form the ester-comprising telomer

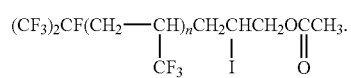

In exemplary embodiments, reagents within reactor 56 can be heated to at least 82° C. for approximately 10 hours during the exposing of the reagents. The reagents can also be exposed in the presence of AIBN at the same temperature for the same amount of time, for example.

In some embodiments, the process of system 50 can be exothermic and the initiator may prevent achieving a temperature that may decompose and/or rearrange products. For example, when the temperature of the contents of the reactor is higher than 90° C. and a dibenzoyl peroxide initiator is utilized, the reaction temperature of ester and telomer can rise to about 160° C.-180° C., and at such high temperature the ester obtained can undergo a thermal rearrangement to $R_F CH_2 CH(OAc) CH_2 I$, thr example. AIBN can be used as the initiator and added stepwise to avoid such a rearrangement and provide a product yield up to 80-82% (by gas chromatography) or 75% (by distillation).

Figure 6:
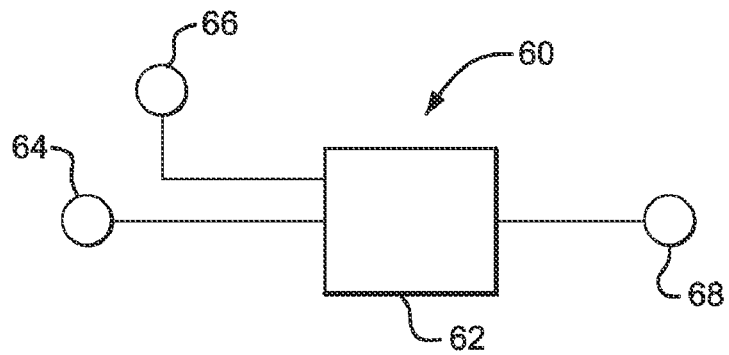
FIG. 6 is an exemplary system for preparing compositions according to an embodiment.

Referring to FIG. 6, system 60 includes a reactor 62 configured to receive reagents such as a telomer 64 and a reducing agent 66 and form an allyl-comprising telomer 68. Telomer 64 can include $R_F$-intermediates such as ester-comprising telomer 58 described above. For example, telomer 64 can include a $Q_1(R_T)_nR_E$, such as

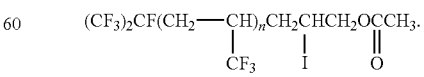

Reducing agent 66 can include one or more reagents, such as a mixture of activated zinc and methanol. Other reducing agents may be utilized. Reactor 62 can be configured to expose agent 66 to telomer 64 at approximately 65° C. and reflux these materials for approximately 3 hours, plus or minus 2 hours. For example, and by way of example only, telomer 64, such as

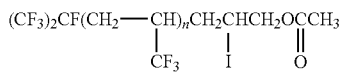

can be added to reactor 62 containing a 2-fold excess of activated Zn dust in MeOH solution. Reactor 62 may be configured to stir and/or even vigorously stir the solution during and/or after addition of telomer 64. According to some embodiments, upon addition of telomer 64, the reaction of the telomer 64 with agent 66 can be exothermic and telomer 64 can be added drop-wise under reflux MeOH to control exotherms, if desired. The conversion of telomer 64 can be quantitative with the overall yield of allyl-comprising telomer 68 being approximately 75% after distillation, for example.

In exemplary embodiments, allyl-comprising telomer 68 can include $Q_1(R_T)_nR_A$, with the $R_A$ group including $Q_g$ as described above and/or at least one allyl group. Allyl-comprising telomer 68 can include $R_F(R_T)_nR_A$, and as such, include at least one fluorine atom. For example and by way of example only, the agent zinc and methanol can be exposed to the telomere

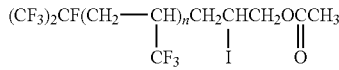

to form the allyl-comprising telomer

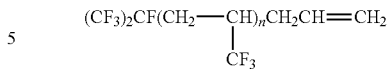

Allyl-comprising telomer 68 can be used as a monomer in the formation of polymers, for example.

In exemplary embodiments, systems 40, 50, and 60 can be aligned sequentially to produce an allyl-comprising telomer 68 from taxogen 42 and telogen 44, when referring to FIGS. 4, 5, and 6 in sequence. In this alignment, telomer 49 produced in system 40 can be utilized as telomer 52 in system 50, and telomer 58 produced in system 50 can be utilized as telomer 64 in system 60. As such, allyl-comprising telomer 68 can include a fluoromonomer that includes a telomer of trifluoropropene. Telomers 49, 52, 64, and 68 can include

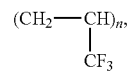

with n being at least 1.

For example, and by way of example only, referring to Table 3 below, telomers, esters, and monomers having the recited characteristics can be produced.

TABLE 3

Telomer, Ester, and Monomer Characteristics

| Run No | Product | Yield by GC* (%) | G.C. RT (min) | Boiling Point °C. | Pressure |
|---|---|---|---|---|---|
| 1 | $C_6F_{13}(CH_2-CH)I$ <br> $\mid$ <br> $CF_3$ | 54.1 | 3.6 | 25 <br> 71-73 | 0. 4 mmHg <br> 20-25 mmHg |
| 2 | $C_6F_{13}(CH_2-CH)_2I$ <br> $\mid$ <br> $CF_3$ | 66.0 | 5.5 | 30 <br> 100-105 | 0.2 mmHg <br> 20-25 mmHg |
| 3 | $C_6F_{13}(CH_2-CH)CH_2CHCH_2OCCH_3$ <br> $\mid \quad \mid \quad \parallel$ <br> $CF_3 \quad I \quad O$ | 55.8 | 11.5 | 70-72 | 0.1 mmHg |
| 4 | $C_6F_{13}(CH_2-CH)CHCH_2OCCH_3$ <br> $\mid \quad \backslash \quad \backslash\backslash$ <br> $CF_3 \quad I \quad O$ | 48.3 | 13.4 | 110-115 | 0.05 mmHg |
| 5 | $C_6F_{13}(CH_2-CH)CH_2CH=CH_2$ <br> $\mid$ <br> $CF_3$ | 80.7 | 3.2 | 68-70 <br> 105-108 | 20-25 mmHg <br> Atm. press. |
| 6 | $C_6F_{13}(CH_2-CH)_2CH_2CH=CH_2$ <br> $\mid$ <br> $CF_3$ | 47.3 | 5.3 | 100-103 | 20-25 mmHg |
| 7 | $(CF_3)_2CF(CH_2-CH)I$ <br> $\mid$ <br> $CF_3$ | 54.1 | 1.5 | 100-110 | Atm. press. |

TABLE 3-continued

Telomer, Ester, and Monomer Characteristics

| Run No | Product | Yield by GC* (%) | G.C. RT (min) | Boiling Point °C. | Pressure |
|---|---|---|---|---|---|
| 8 | (CF$_3$)$_2$CF(CH$_2$—CH(CF$_3$))$_2$I | 45.8 | 3.2 | 65-70 | 20-25 mmHg |
| 9 | (CF$_3$)$_2$CF(CH$_2$—CH(CF$_3$))CH$_2$CH(I)CH$_2$OC(O)CH$_3$ | 80.5 | 8.2-8.9 | 115-120<br>65-70 | 20-25 mmHg<br>1 mmHg |
| 10 | (CF$_3$)$_2$CF(CH$_2$—CH(CF$_3$))$_2$CH$_2$CH(I)CH$_2$OC(O)CH$_3$ | 63.8 | 10.8-11.1 | 78-84 | 0.1 mmHg |
| 11 | (CF$_3$)$_2$CF(CH$_2$—CH(CF$_3$))CH$_2$CH═CH$_2$ | 69.3 | 1.3-1.5 | 105-110 | Atm. press. |
| 12 | (CF$_3$)$_2$CF(CH$_2$—CH(CF$_3$))$_2$CH$_2$CH═CH$_2$ | 86.9 | 2.9-3.1 | 63-64 | 20-25 mmHg |

*GC analysis: column OV I (3% silicone grease on the chromosorb G) ; 2 m length, 1/8" diameter, 50-200° C. ramp.

According to another embodiment of the disclosure, the R$_F$-intermediate including the telomers described above can be modified according to scheme (24) below.

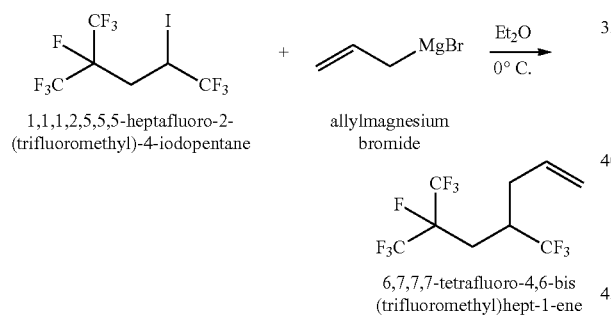

(24)

1,1,1,2,5,5,5-heptafluoro-2-(trifluoromethyl)-4-iodopentane + allylmagnesium bromide → 6,7,7,7-tetrafluoro-4,6-bis(trifluoromethyl)hept-1-ene In accordance with scheme (24) above, a 150 mL three-neck round bottom flask can be equipped with a reflux condenser, agitator, thermocouple, heating mantle, and a 150 mL pressure equalized addition funnel that can contain 70 mL of allylmagnesium bromide in a 1.0M solution of diethyl ether. About 27.64 grams (0.07 mole) of 1,1,1,2,5,5,5-heptafluoro-2-(trifluoromethyl)-4-iodopentane can be added to the flask. The allylmagnesium bromide solution can be added slowly to the flask wherein an exotherm can be observed along with a change in color from orange to colorless. The allylmagnesium bromide can be added over a period of 2.5 hours then the reaction mixture can be held at room temperature overnight. After the hold period, the reaction mixture can be washed in water to quench any unreacted allylmagnesium bromide, an organic layer can be observed, decanted off, and dried over MgSO$_4$. Samples of dried organic layer can be analyzed by gas chromatography/mass spectroscopy. (m/z 306 (M$^+$), 237 (M$^+$–CF$_3$)).

In accordance with another embodiment of the disclosure, R$_F$-intermediates including the telomers described above can be modified to form additional R$_F$-intermediates. For example, and by way of example only, the R$_F$-intermediate 1,1,1,2,6,7,7,7-octafluoro-2,6-bis(trifluoromethyl)-4-iodoheptane can be modified to form the R$_F$-intermediate 6,7,7,7-tetrafluoro-4-(2,3,3,3-tetrafluoro-2-(trifluoromethyl)propyl)-6-(trifluoromethyl) hept-1-ene according to scheme (25) below.

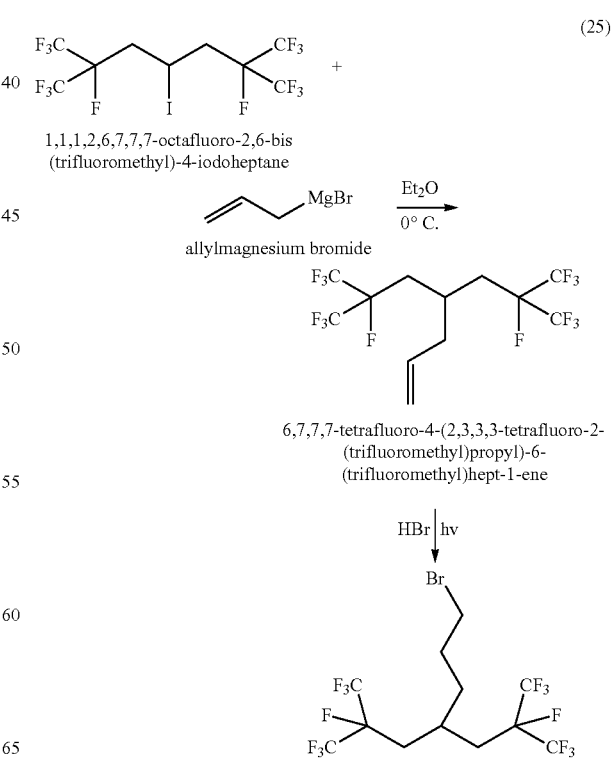

(25)

Referring to scheme 25 above, a dried flask can be charged with

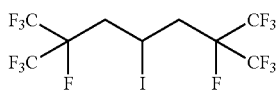

(488 grams) and anhydrous ether (306 mLl) to form a mixture. The mixture can be cooled to 0° C. with an ice/water bath and 1M allylmagnesium bromide in ether (976 mL) can be added slowly to the mixture over 3 hours and the mixture allowed to warm to room temperature overnight. Saturated ammonium chloride (500 mL) can then be added drop-wise to the mixture at a rate to keep the temperature of the mixture at <5° C., and deionized water (250 mL) can be added to aid in the dissolution of the salts and form a biphasic mixture from which the organic layer can be separated and dried over magnesium sulfate, filtered and distilled at 5 Torr and 41° C.-43° C. to afford a clear liquid (361 g, 84.2%). Residual ether can be boiled off to afford 359.6 grams

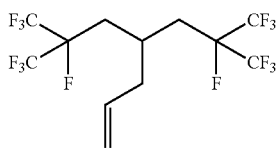

as can be identified by NMR.

As another example, into a dry 500 mL round bottom flask, equipped with an addition funnel, can be added 120 grains (0.24 moles) of (1,1,1,2,6,7,7,7-octafluoro-2,6-bis(trifluoromethyl)-4-iodoheptane) to 150 mL of anhydrous THF to form a mixture. Under a $N_2$ atmosphere, the mixture can be cooled to 0° C. while stirring vigorously. To the mixture can be added 120 mL of a 2M solution of allylmagnesium bromide in THF at a rate to maintain a temperature of the mixture of less than about 5° C. After addition of the allylmagnesium bromide solution, the flask can be allowed to slowly warm to room temperature.

A white powdery suspension can form during the reaction and can be removed by suction filtration to form a filter cake. The filter cake can be washed with 100 mL of THF, and the filtrate collected and added to 3 to 5 mL of water to destroy any remaining allylmagnesium bromide. The THF can be distilled off and the remaining solution can be washed with water. The organic layer (90.7 grams) can be dried with $MgSO_4$ and distilled at 40° C.-41° C./5 Torr to isolate about 63 grams of 63.5% (area percent by gas chromatography) $R_F$-intermediate 6,7,7,7-tetrafluoro-4-(2,3,3,3-tetrafluoro-2-(trifluoromethyl)propyl)-6-(trifluoromethyl)hept-1-ene.

As further disclosed in scheme (25) above, the 6,7,7,7-tetrafluoro-4-(2,3,3,3-tetrafluoro-2-(trifluoromethyl)propyl)-6-(trifluoromethyl)hept-1-ene can be modified to produce another $R_F$-intermediate. Referring to the scheme above, into a 100 mL pressure tube equipped with a 9 inch Pen-Ray® Hg lamp, pressure gauge, agitator, and dip tube can be added 60 grams (0.14 moles, of 6,7,7,7-tetrafluoro-4-(2,3,3,3-tetrafluoro-2-(trifluoromethyl)propyl)-6-(trifluoromethyl)hept-1-ene. The tube can be sealed and gaseous anhydrous HBr can be bubbled into the system to maintain a pressure of 101.37 kPa to 308.27 kPa. The tube can be irradiated with the Pen-Ray lamp until the pressure ceases to decrease. The mixture can then be washed once with water and once with 10% aqueous sodium bicarbonate. The organic layer can assay as high as 92.7% (area percent by gas chromatography) and can be dried with $MgSO_4$ and distilled at 73° C.-74° C./3.1 Torr.

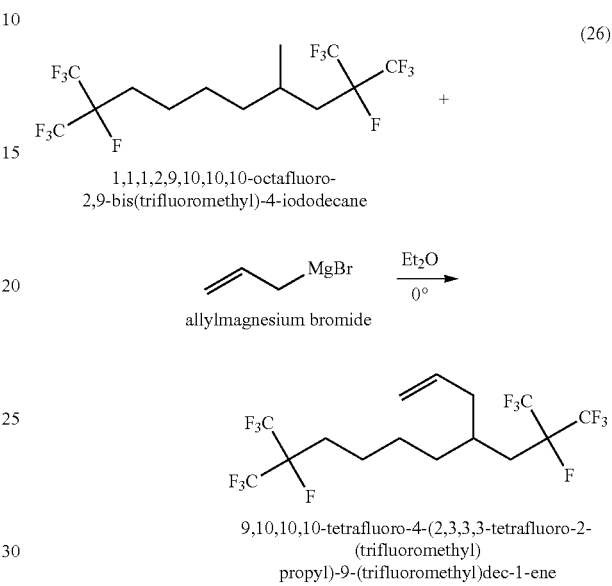

Referring to scheme (26) above, to a 250 mL three-neck round bottom flask equipped with thermocouple, agitator, and reflux condenser 71.05 grams (0.3 mole) of the RF-intermediate 1,1,1,2,8,9,9,9-octafluoro-2,8-bis(trifluoromethyl)-4-iodooctane can be added, then chilled to 0° C. in an ice bath. About 121.37 grams (0.14 mole) of 1.0M allylmagnesium bromide in diethylether can be added drop-wise with a 150 mL pressure equalized addition funnel over a period of 3 hours. Following the addition, the solution can be gradually warmed to room temperature and held for 48 hours. The mixture can then be quenched with deionized water and the organic layer decanted off and dried over $MgSO_4$. The crude RF-intermediate 8,9,9,9-tetrafluoro-4-(2,3,3,3-tetrafluoro-2-(trifluoromethyl)propyl)-8-(trifluoromethyl)non-1-ene can be assayed by mass spectrometry (m/z 462 (M+), 420.1 (M+−42), 279.1 (M+−183)).

According to an additional embodiment, $R_F$-intermediates, including the telomers described above, such as 1,1,1,2,2,3,3,4,4,5,5,6,6,9,9,9-hexadecafluoro-8-iodononane, can be modified according to scheme (27) below.

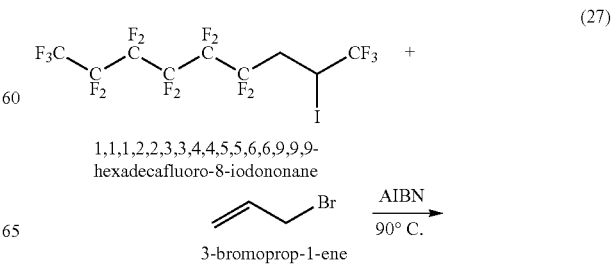

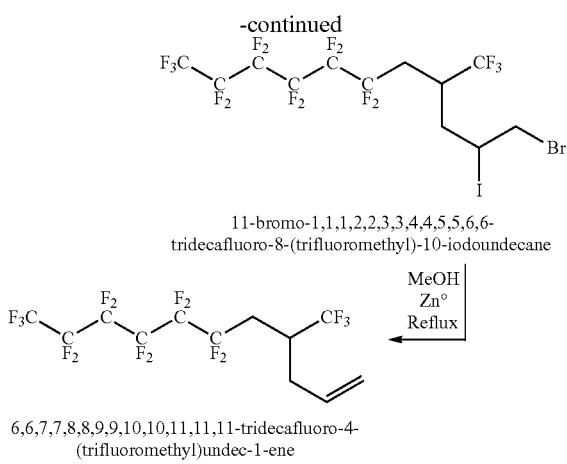

11-bromo-1,1,1,2,2,3,3,4,4,5,5,6,6-
tridecafluoro-8-(trifluoromethyl)-10-iodoundecane 6,6,7,7,8,8,9,9,10,10,11,11-tridecafluoro-4-
(trifluoromethyl)undec-1-ene An embodiment of the disclosure provides $R_F$-surfactant compositions that include the $R_F$ portions described above. Exemplary $R_F$-surfactant compositions can be referred to as $R_F$-$Q_5$. In a system having at least two parts, $R_F$ can have a greater affinity for a first part of the system than $Q_5$, and $Q_5$ can have a greater affinity for a second part of the system than $R_F$. The system can include liquid/liquid systems, liquid/gas systems, liquid/solid systems, and/or gas/solid systems. Liquid/liquid systems, for example, can include systems having at least one part that includes water and another liquid part that is hydrophobic relative to the part that includes water. Liquid/liquid systems can also include systems of which water is not a part of the system, such as hydrocarbon liquid systems. In exemplary embodiments, $R_F$ can be hydrophobic relative to $Q_5$ and/or $Q_5$ can be hydrophilic relative to $R_F$. $R_F$ can be hydrophobic and $Q_5$ can be hydrophilic, for example. The hydrophobic portion can be referred to as the tail of the $R_F$-surfactant, and the hydrophilic portion can be referred to as the head of the $R_F$-surfactant. The $R_F$-surfactants can include those surfactants having a tail or hydrophobic portion containing fluorine. The $R_F$-surfactant tail or hydrophobic portion can be referred to as an $R_F$ portion, and the $R_F$-surfactant head or hydrophilic portion can be referred to as a $Q_5$ portion. Exemplary $R_F$-surfactants include those in Table 4 below.

TABLE 4

$R_F$-surfactants

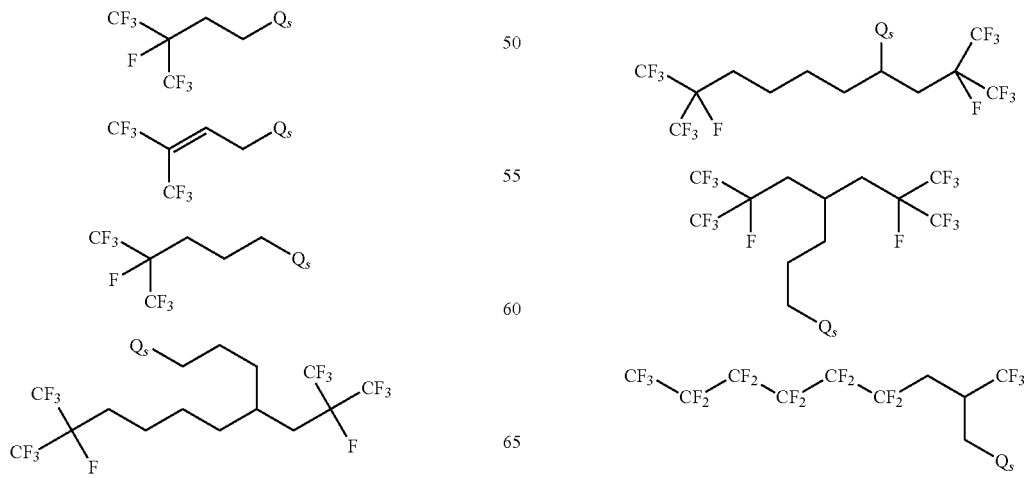

TABLE 4-continued

R_F-surfactants

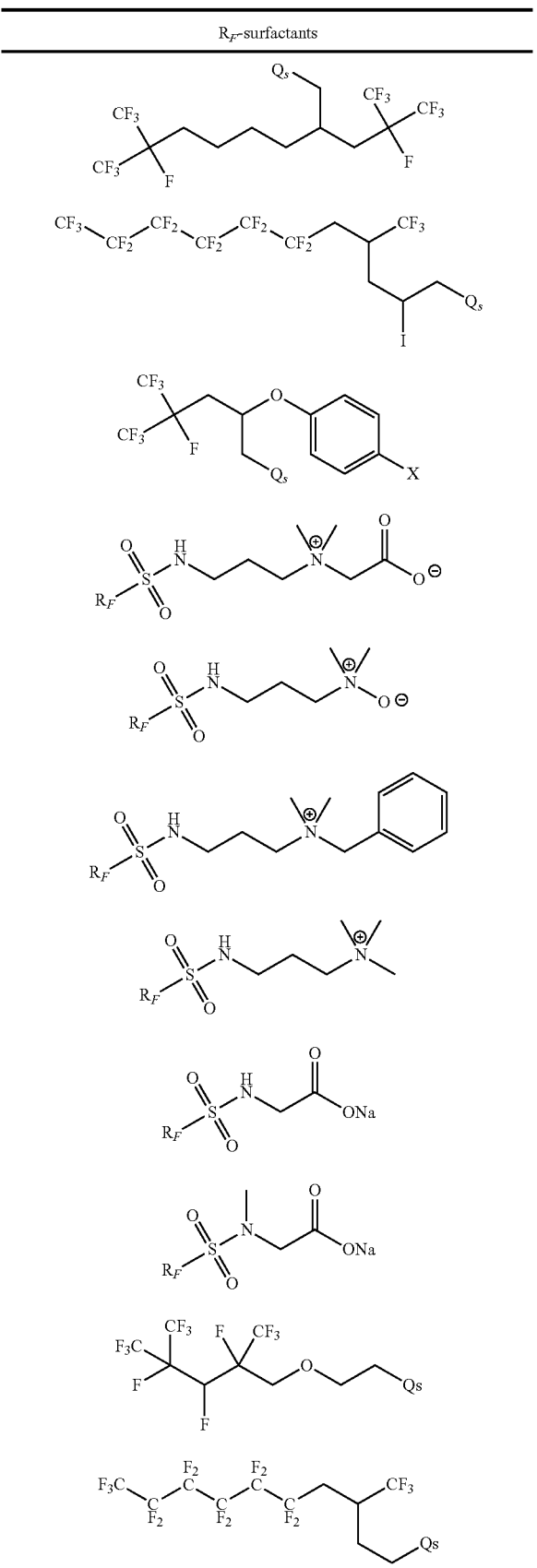
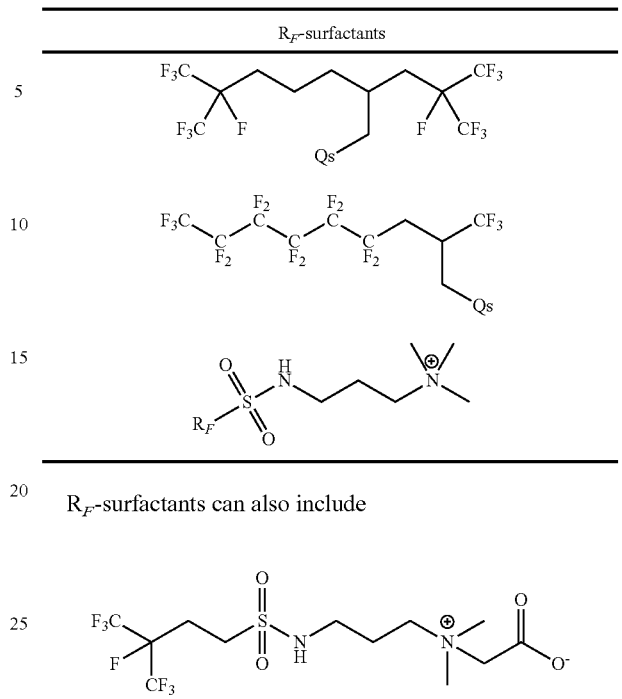

R_F-surfactants can also include

NMR: 1H (D6-DMSO, 300 MHz) δ 1.8 (m, 2H), 2.6 (m, 2H), 3.0 (m, 2H), 3.1 (bs, 6H), 3.6 (m, 2H), 3.9 (m, 4H), 7.9 (bs, 1H); 13C (D6-DMSO, 75 MHz) δ 22.6, 22.9, 23.1, 43.1, 50.0, 60.8, 64.4, 88-93 (ds), 114.5-126.5 (qd); and 19F (CFCl3, D6-DMSO, 282 MHz) δ −76.4 (d, 6.95 Hz, 6F), −183.4 (m, 1F)

According to an embodiment of the disclosure, $R_F$-surfactant production processes are provided. Exemplary $R_F$-surfactant production processes include providing an $R_F$-intermediate such as the $R_F$-intermediates described above having at least two —$CF_3$ groups. Exemplary $R_F$-intermediates can include $R_F$-Qg with Qg being designated for later attachment to the Qs portion of $R_F$-surfactants, for example. Exemplary methods for preparing surfactants can be found in German Offen. 1,924,264 and U.S. Pat. No. 3,721,706 both of which are hereby incorporated by reference. Exemplary methods for preparing $R_F$-surfactants are described below.

Figure 7:
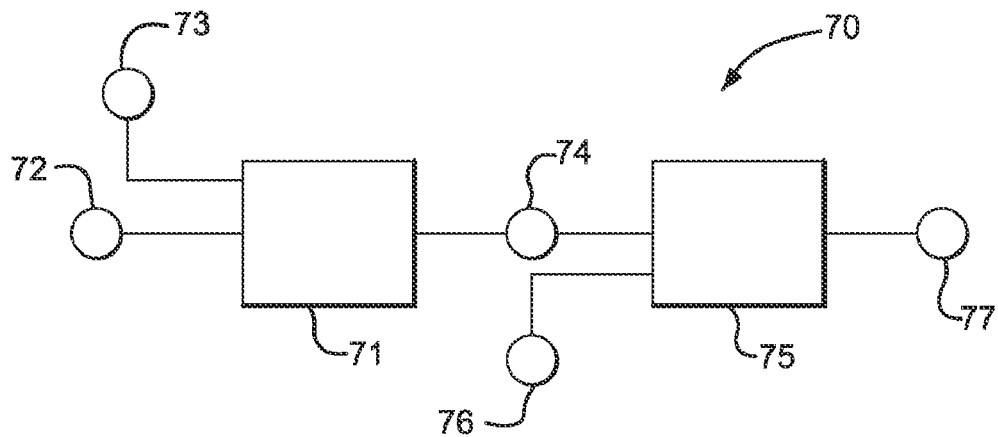
FIG. 7 is an exemplary system for preparing compositions according to an embodiment.

Referring to FIG. 7, a system 70 is shown that can be configured to perform a process that includes reacting an $R_F$-intermediate to form a $R_F$-surfactant, with the $R_F$-intermediate including at least one fluorine atom, for example. System 70 can include reactors 71 and 75. Reactor 71 can be configured to expose an $R_F$-intermediate 72 to a radical reagent 73. In exemplary embodiments, $R_F$-intermediate 72 can include an $R_F$ portion, such as those described above.

Reagent 73 can include $HSCH_2CO_2H$, for example. $R_F$-intermediate 72 can be exposed to reagent 73 in the presence of a radical initiator, such as AIBN to produce a $R_F$-intermediate 74 such as $R_F$—$C_3H_6$—S—$CH_2CO_2H$, for example.

In exemplary embodiments, reactor 75 can be configured to combine $R_F$-intermediate 74 and reagent 76 to produce a $R_F$-surfactant 77. Reagent 76 can include $HO(CH_2CH_2O)n$-$CH_3$ and $R_F$-surfactant 77 can include $R_F$—$C_3H_6$—S—$CH_2C(O)(CH_2CH_2)nCH_3$, with n being at least 1, for example.

As another example, reagent 73 can include radical initiators and/or ethylene ($CH_2$=$CH_2$). Upon exposing $R_F$-intermediate 72 to reagent 73 within reactor 71, $R_F$-intermediate

74, such as $R_F CH_2CH_2I+N(CH_3)_3$, can be produced, for example. Reactor 72 can be configured to expose $R_F$-intermediate 74 to reagent 76 to form $R_F$-surfactant 67. Reagent 76 can include pyridine, for example. $R_F$-surfactant 77 can include $R_F$-surfactants such as $R_F$-$Q_s$, with $Q_s$ including a quaternary ammonium ion such as $-CH_2CH_2N^+(CH_3)_3I^-$, for example.

In accordance with another embodiment, $R_F$-intermediates can be converted to thiocyanate $R_F$-intermediates such as $R_F$—SCN, by reacting heterohalogenated $R_F$-intermediates such as iodine $R_F$-intermediates, for example, with potassium thiocyanate. The reaction can be carried out in absolute ethanol using acetic acid as a catalyst. A 30% molar excess of KSCN as compared to the $R_F$-intermediate can be used. The ethanol, acetic acid, $R_F$-intermediate, and KSCN can be charged to a reaction vessel, heated to reflux, and held there until the reaction is complete. The reaction progress can be monitored by analyzing the reaction mixture for $R_F$-intermediate by gas chromatography. Upon reaction completion, the KI formed can be filtered off the reaction mixture, the ethanol can be evaporated away, and the thiocyanate $R_F$-intermediate can be washed twice with hot (70° C.) water. Reagent 73 can include a mixture of the KSCN, ethanol and acetic acid described above. The $R_F$-intermediate can be exposed to the mixture at a temperature of about 83° C. and/or reflux temperature to produce an intermediate 74 such as $R_F$—SCN.

$R_F$-intermediate 74 can then be exposed to reagent 76 to form intermediate 77. $R_F$-intermediate 74, such as $R_F$—SCN can be wet chlorinated to give the sulfonylchloride of the $R_F$-intermediate as shown below in exemplary reaction sequence (28).

$$2R_F\text{—SCN} + 8H_2O + 9Cl_2 \rightarrow 2R_F\text{—SO}_2Cl + 2CO_2 + N_2 + 16HCl \quad (28)$$

The $R_F$—SCN, water, and acetic acid as a solvent can be charged to reactor 75. Chlorine can be added to the reaction vessel in 30 minute increments while the temperature of the mixture within reactor 75 is maintained at 20° C. to 30° C. At the end of each 30 minutes of chlorine addition, 0.314 grams of water can be added to reactor 75. For each gram of chlorine that is added, 4.5 moles per mole of $R_F$—SCN can be added. When this amount has been added, the mixture within reactor 75 can be sampled and analyzed for $R_F$—SCN by gas chromatography. When the reaction is complete, the mixture within reactor 75 can be diluted to 65% (wt/wt) $R_F$—SO$_2$Cl with chloroform, heated to about 40° C. and washed with twice its volume of 40° C. water. After the wash, the washed mixture can be dried by azeotropic distillation of the water using a Dean Stark trap. Karl Fischer titration can be used to determine water amount. Water content can be less than 0.1%. As described above, reagent 76 can include a mixture of Cl$_2$, H$_2$O, and acetic acid. $R_F$-intermediate 74 can be exposed to the mixture at a temperature of about 30° C. to 40° C. to produce $R_F$-intermediate 67, such as $R_F$—SO$_2$Cl.

Figure 8:
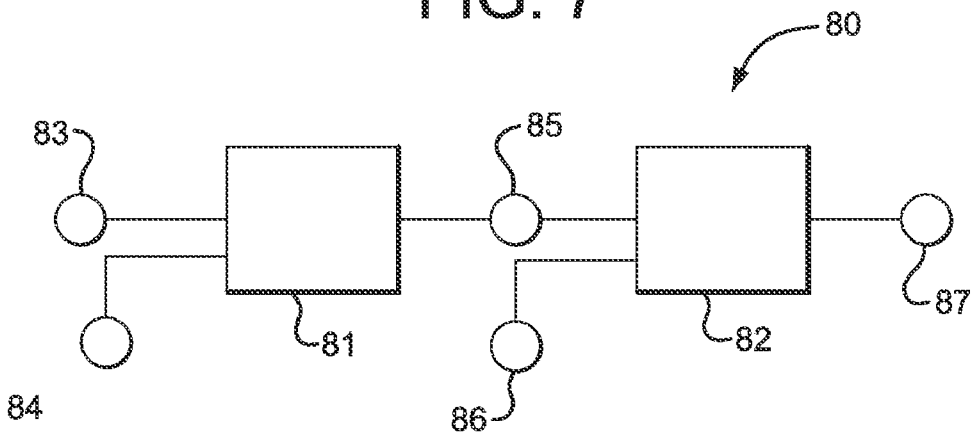
FIG. 8 is an exemplary system for preparing compositions according to an embodiment.

Referring to FIG. 8, in an additional embodiment, a system 80 configured to produce $R_F$-surfactants from $R_F$-intermediates, for example, those produced in system 70, such as $R_F$-intermediate 77, is shown. System 80 can include reactors 81 and 82. Reactor 81 can be configured to expose an $R_F$-intermediate 83, such as $R_F$-intermediate 77 described above, to reagent 84. $R_F$-intermediate 83 can have the general formula $R_F$—SO$_2$Cl described above, for example. In an exemplary embodiment, exposing $R_F$-intermediate 83 to reagent 84 esterifies intermediate 83 to form $R_F$-intermediate 85, which can include a sulfonamidoamine. Dimethylaminopropylamine(H$_2$N(CH$_2$)$_3$N(CH$_3$)$_2$, DMAPA) can be used to esterify intermediate 83 as shown as exemplary reaction scheme (29) and described below.

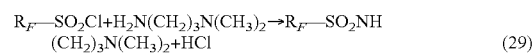

The esterification can be performed in a chloroform solution at reflux. The solvent and reactants can be as dry as having at least less than 0.1% by weight water. The DMAPA can be dissolved in 1.5 times its volume in chloroform in reactor 81 which can be immersed in a cooling bath. A DMAPA molar equivalent of 65% (wt/wt) $R_F$—SO$_2$Cl in chloroform solution can be added to reactor 81 while maintaining the temperature of the contents of reactor 81 at less than 50° C. When the addition is complete, the temperature of the contents can be raised to reflux and held at reflux for 5 hours. Reactor 81 contents can then be cooled to 60° C. and washed 3 times with equal volumes of 60° C. water. Chloroform remaining can be stripped under vacuum, and the neat product can be washed twice with 90° C. water. The washed neat product can be sampled and analyzed for free DMAPA using a wet chemistry method that is specific for primary amines.

According to an exemplary embodiment, reagent 84 can include a mixture of DMAPA and CHCl$_3$. Intermediate 83 can be exposed to the mixture at a temperature from between about 30° C.-65° C. to produce $R_F$-intermediate 85, such as

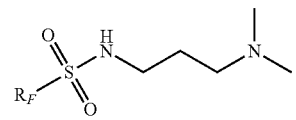

for example. As another example, reagent 84 can include a mixture of 2-aminoacetic acid and CHCl$_3$ and intermediate 83 can be exposed to the mixture at a temperature from between about 30° C.-65° C. to produce $R_F$-intermediate 85, such as

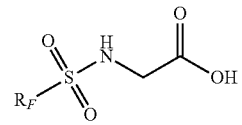

Reagent 84 can also include a mixture of 2-(methylamino) acetic acid and CHCl$_3$ and intermediate 83 can be exposed to the mixture at a temperature from between about 30° C.-65° C. to produce intermediate 85, such as

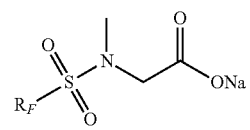

Intermediate 85 can then be betainized, for example, with an acetate reagent such as sodium monochloroacetate within reactor 82 to yield $R_F$-surfactant 87, such as the amphoteric $R_F$-surfactant $R_F$—SO$_2$NH(CH$_2$)$_3$N$^+$(CH$_3$)$_2$(CH$_2$CO$_2$Na) as shown as exemplary reaction sequence (30) and described below.

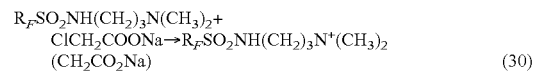

The sulfonamide can be dissolved in enough absolute ethanol to give a 40% (wt/wt) solution. An equimolar amount of sodium monochloroacetate can be added to reactor 82 containing the 40% (wt/wt) solution to form a mixture. The mixture can then be refluxed for 8 hours and then sampled and titrated for free OH⁻. If OH⁻ is greater than $1.5\times10^{-3}$ eq., the mixture is refluxed for an additional hour and reanalyzed. This sequence can be repeated until free OH⁻ is less than $1.5\times10^{-3}$ eq. If there is no decline in OH⁻ in two succeeding samplings, additional sodium monochloroacetate can be added, the amount being calculated as the amount needed to lower the OH⁻ to a value below $1.5\times10^{-3}$ eq. The by-product NaCl can be filtered off and sufficient water is added to give a pourable solution at ambient temperature.

Reactor 82 can be configured to expose Intermediate 85, such as

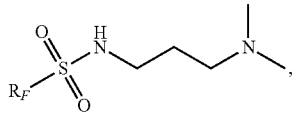

to reagent 86 to form $R_F$-surfactant 87. According to an exemplary embodiment, reagent 86 can include a mixture of

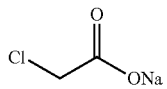

and ethanol. Intermediate 83 can be exposed to the mixture while the mixture is refluxing to produce $R_F$-surfactant 87, such as

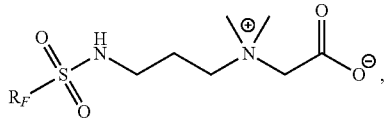

for example. As another example, reagent 86 can include a mixture of 50% (wt/wt) $H_2O_2/H_2O$ and intermediate 83, such as

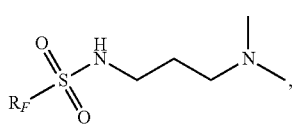

for example, can be exposed to the mixture at a temperature of about 35° C. to produce $R_F$-surfactant 87, such as Reagent 86 can also include 1-(chloromethyl)benzene, and intermediate 85, such as

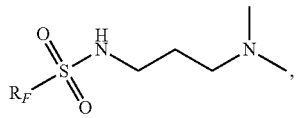

can be exposed to the 1-(chloromethyl)benzene to produce $R_F$-surfactant 87, such as

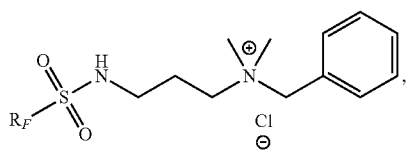

In accordance with another example, reagent 86 can include 1-(bromomethyl)benzene, and intermediate 85, such as

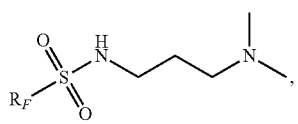

can be exposed to the 1-(bromomethyl)benzene to produce $R_F$-surfactant 87, such as

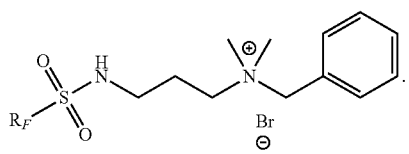

As another example, reagent 86 can include bromomethane and intermediate 85, such as

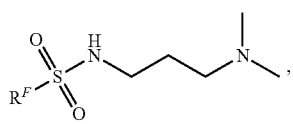

can be exposed to the bromomethane to produce $R_F$-surfactant 87, such as

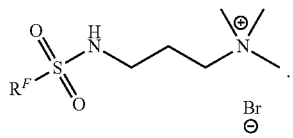

Reagent 86 can also include chloromethane and intermediate 85, such as

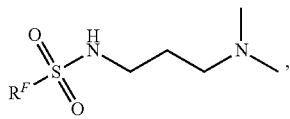

can be exposed to the chloromethane to produce $R_F$-surfactant 87, such as

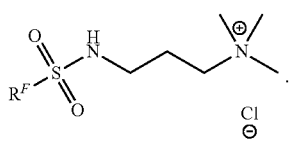

In accordance with another embodiment, reagent 86 can also include a basic solution such as NaOH and intermediate 85, such as

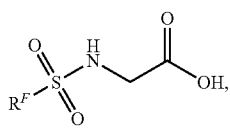

can be exposed to the solution to produce $R_F$-surfactant 87, such as

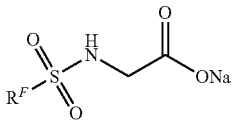

Systems 70 and 80 may be combined in sequence and $R_F$-surfactants produced according to schemes (31)-(45) below. Where LC/MS can be used to identify compounds, Table 5 of LC/MS parameters, below, can be used.

TABLE 5

| LC-MS Parameters | |
|---|---|
| Column Type: | Phenomonex Luna C18 column, 5 micrometer |
| Column Size: | 2 × 50 mm |
| Column Temp: | 25° C. |
| Gradient Pump | Agilent 1100 Quat Pump G1311A |
| Detector: | Agilent Diode Array Detector G13115B |
| Detector Wavelength: | 250 nm (referenced against 380 nm) |
| Mass Detector: | Agilent 1100 MSD G1946C |
| Source: | Electrospray Positive ion |
| Fragmentor: | 80 |
| Software | ChemStation Rev A.08.03 |
| Conc: | Ca 100 ppm |
| Injector: | 10 microliter Rheodyne |
| Elution Type: | Gradient |
| Flow Rate: | 0.3 mL/min |
| Mobile Phase: | A: Water (J T Baker HPLC grade) w/0.05% $HCO_2H$<br>B: Acetonitrile w/0.05% $HCO_2H$ |
| Gradient Conditions: | 90:10 A:B increase to 100% B in 6 min and then hold for 4 min at 100% B |

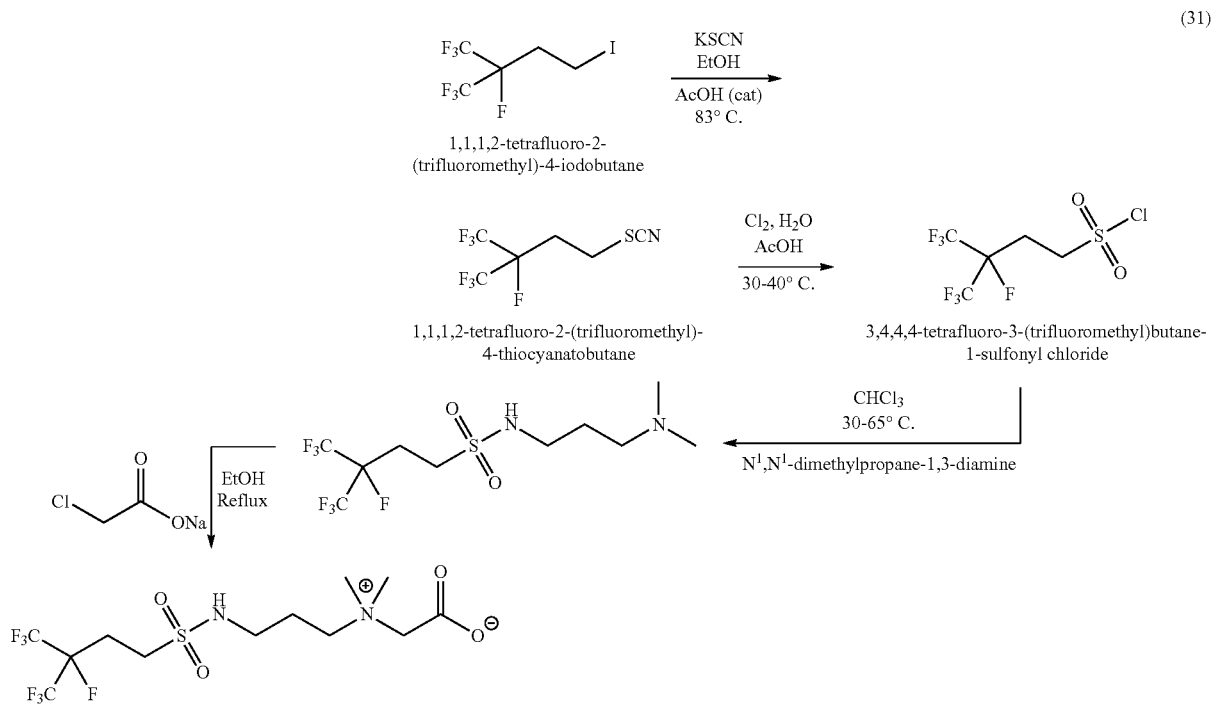

(31)

In accordance with scheme (31) above, a mixture of 1,1,1,2-tetrafluoro-4-iodo-2-trifluoromethyl-butane (100 grams) and potassium thiocyanate (39 grams) can be dissolved in 55 mL of ethanol and 1 mL of acetic acid and heated to reflux, where it can be allowed to reflux for a couple of days. The mixture can be cooled to room temperature and concentrated to dryness under vacuum. Deionized water 100 mL) can be added to the dry solids and the resulting oil can be decanted and identified to be 1,1,1,2-tetrafluoro-4-thiocyanate-2-trifluoromethyl-butane (69.9 grams, 88.4%) by NMR analysis.

A mixture of the 1,1,1,2-tetrafluoro-4-thiocyanate-2-trifluoromethyl-butane (25.5 grams) in 25 mL of acetic acid containing 2 mL of water can be sparged with chlorine gas at 40° C. for a couple of days with intermittent heating of the mixture to form a heterogeneous mixture. The mixture can be cooled to room temperature and diluted with chloroform (50 mL). The organic portion can be washed twice with water, dried over sodium sulfate, filtered, and concentrated under vacuum. The resulting yellow oil can contain large amounts of residual acetic acid by NMR analysis. The yellow oil can be dissolved in chloroform and washed twice with water (25 mL/each), dried over sodium sulfate, filtered, and concentrated under vacuum and identified to be 4,4,4,3-tetrafluoro-4-trifluoromethyl-butanesulfonyl chloride (23.8 grams, 80%) by NMR analysis.

The 4,4,4,3-tetrafluoro-4-trifluoromethyl-butanesulfonyl chloride (23.8 grams) can be dissolved in 50 mL of ether and added drop-wise to a solution of dimethylaminopropylamine (8.2 g) and 11.2 mL of triethylamine (TEA) at ambient over 20 minutes to form a mixture. The mixture can be partitioned between ethyl acetate (100 mL) and water (150 mL). The organic layer can be separated and washed with saturated bicarbonate solution (50 mL) and brine (50 mL), dried over sodium sulfate, filtered, and concentrated under vacuum to a yellow semi solid. NMR and LC/MS analysis can indicate the yellow semi solid can be a mixture of the mono and bis sulfonated material. The semi solid can be triturated in hexanes, and the filtered solid identified as 3,4,4,4-tetrafluoro-3-trifluoromethyl-butane-1-sulfonic acid (3-dimethylamino-propyl)-amide (9.9 grams) by NMR analysis.

The 3,4,4,4-tetrafluoro-3-trifluoromethyl-butane-1-sulfonic acid (3-dimethylamino-propyl)-amide (10 grams can be dissolved in 50 mL of ethanol containing 3.2 grams of sodium chloroacetate to form a mixture and can be refluxed overnight. The mixture can be filtered, concentrated under vacuum, and distilled twice using chloroform to afford

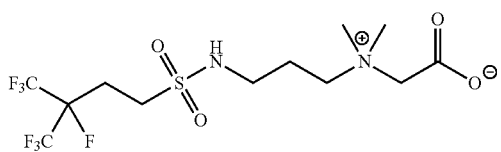

by NMR analysis. The product can be placed on the Kugelrohr at 60° C. and 0.1 Torr to afford a pale yellow foam like solid (10 grams, 84%).

(32)

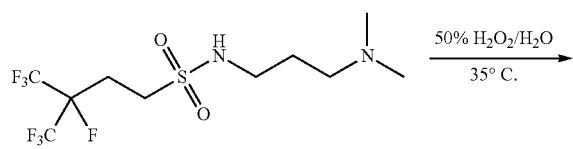

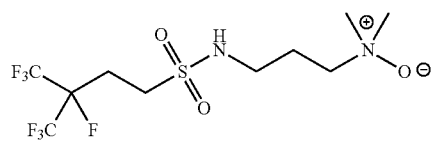

In accordance with scheme (32) above, 3,4,4,4-tetrafluoro-3-trifluoromethyl-butane-1-sulfonic acid (3-dimethylamino-propyl)-amide (9 grams) can be dissolved in 20 mL of ethanol and 3.5 mL of water and treated with 5.9 mL, of 50% (wt/wt) hydrogen peroxide. The resulting mixture can be heated to 35° C. overnight and the reaction determined to be complete by LC/MS analysis.

Norit, a decolorizing carbon (4 grams) can be added to the mixture, stirred for 30 minutes, and filtered through celite. Additional carbon (4 grams) can be added, the mixture heated to 50° C., the heated mixture filtered through celite again, the resulting filter cake washed with ethanol, and the combined filtrates concentrated under vacuum to leave white solids. The white solid can be identified to be

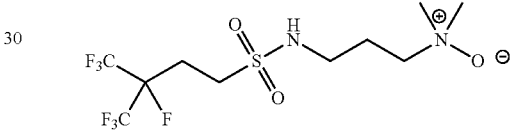

by NMR and LC/MS analysis. The white solid can be dried on the Kugelrohr at 45° C. and 0.1 Torr to afford 8.7 grams (92%) product by NMR analysis.

(33)

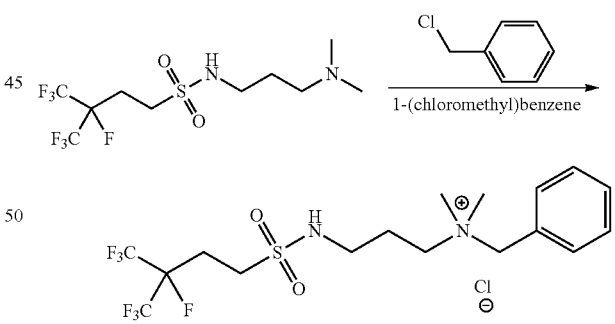

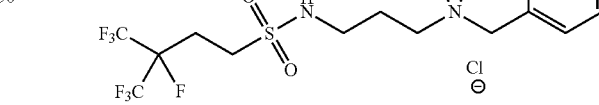

In accordance with scheme (33) above, 5.0 grams of 3,4,4,4-tetrafluoro-3-trifluoromethyl butane-1-sulfonic acid-(3-dimethylamino-propyl)amide can be dissolved in 15 mL of t-butyl methyl ether in a three-necked, 100 mL round bottom flask equipped with a stir bar, reflux condenser and a thermocouple. 1.75 grains of benzyl chloride can be added to the flask to form a mixture and the mixture heated to reflux (56° C.) and agitated. A white precipitate can form when the temperature reaches 56° C. The mixture can be cooled to room temperature after 3 hours. The solids can be collected by filtration, washed with chloroform and air-dried to afford 2.83 grams of

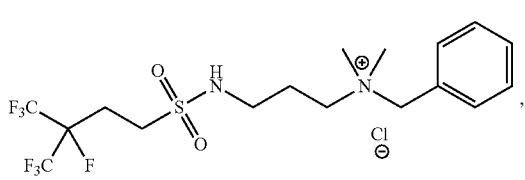

as identified by NMR.

(34)

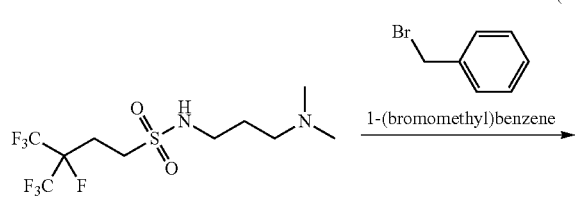

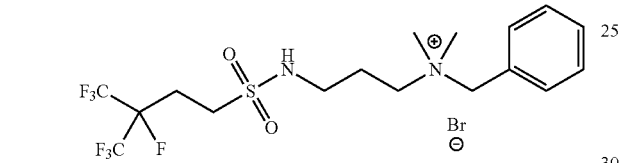

In accordance with scheme (34) above, 5.0 grams of 3,4,4,4-tetrafluoro-3-trifluoromethyl butane-1-sulfonic acid-(3-dimethylamino-propyl)amide can be dissolved in 15.0 mL of t-butyl methyl ether in a three-necked, 100 mL round bottom flask equipped with a stir bar, reflux condenser and a thermocouple. Benzyl bromide (2.36 grams) can be added to the flask to form a mixture and the mixture heated to reflux (56° C.) and agitated for 2 hours. A white precipitate can form when the temperature of the mixture reached 56° C. The mixture can become too thick to stir after 2 hours. The mixture can be cooled to room temperature and the solids collected by filtration and dried in a vacuum oven at 45° C. overnight to afford 6.24 grams (99.6%)

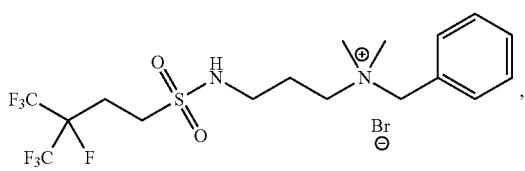

as can be identified by NMR.

(35)

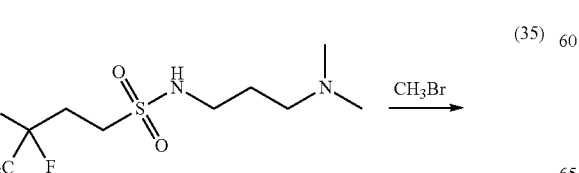

-continued

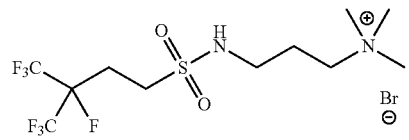

In accordance with scheme (35) above, 10.0 grams of 3,4,4,4-tetrafluoro-3-trifluoromethyl butane-1-sulfonic acid-(3-dimethylamino-propyl)amide can be dissolved in 13.8 mL of a 2.0M solution of bromomethane in diethyl ether in a 25×250 mm culture tube with a teflon lined cap to form a mixture. The mixture can be heated to 45° C. for 4 hours to form a thick precipitate. The mixture can be cooled to room temperature and the solids collected by filtration and dried under vacuum to afford a white solid that can be identified as 7.46 grams (59.9%)

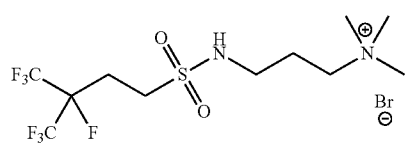

by LC/MS.

(36)

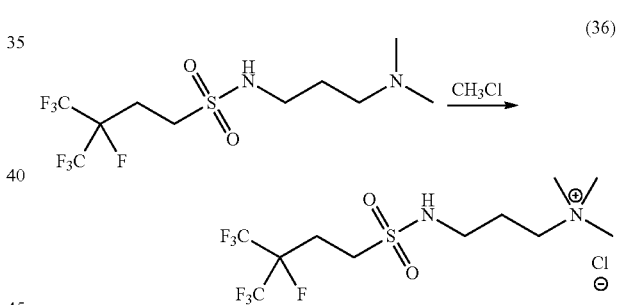

In accordance with scheme (36) above, 5.0 grams of 3,4,4,4-tetrafluoro-3-trifluoromethyl butane-1-sulfonic acid-(3-dimethylamino-propyl)amide can be dissolved in 13.8 mL of a 1.0M solution of chloromethane t-butyl methyl ether in a three-necked, 100 mL round bottom flask equipped with a stir bar, reflux condenser and a thermocouple to form a mixture. The mixture can be heated to reflux (56° C.) and stirred for 4 hours to form a heavier precipitate that can be filtered to yield 0.56 grams of

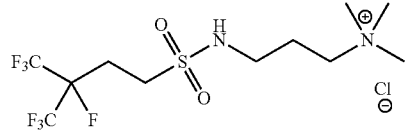

that can be identified by NMR. $R_F$-surfactants can also be prepared in accordance with scheme 37 below.

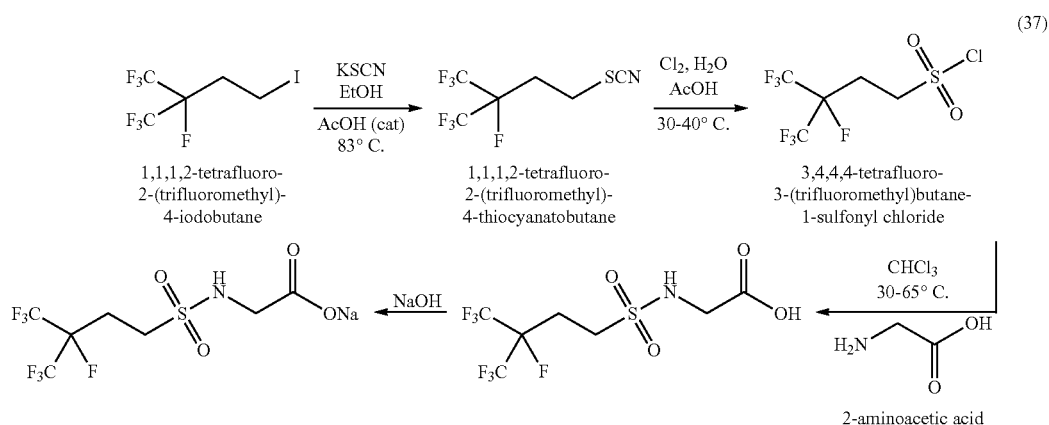

(37)

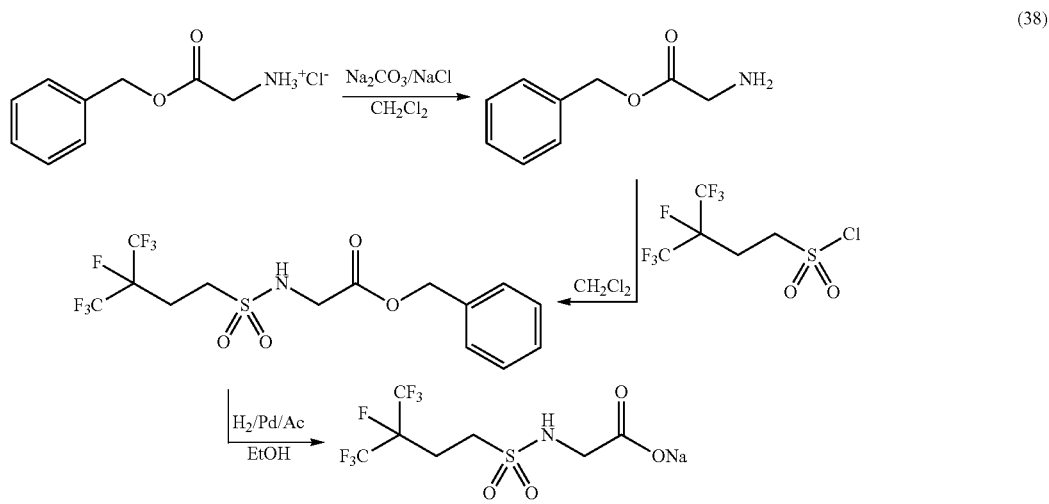

(38)

In accordance with scheme (38) above, 9.68 grams of glycine benzyl ester hydrochloride can be partitioned between 100 mL of methylene chloride and 200 mL of a 1:1 solution of 15% (wt/wt) aqueous sodium carbonate and brine. The layers can be separated and the bottom organic layer washed with 200 mL of a 1:1 solution of 15% (wt/wt) aqueous sodium carbonate and brine. The layers can be separated again, and the organic layer dried over sodium sulfate, filtered and concentrated under vacuum to afford 5.42 grams (68.3%) of a light yellow oil identified as benzyl glycinate by NMR.

A solution of 5.421 grams of the benzyl glycinate demonstrated above, in 15.0 mL of methylene chloride in a three-necked, 100 mL round bottom flask equipped with a stir bar, addition funnel with a nitrogen inlet and a thermocouple, can be chilled to 0° C.-5° C. in an ice bath. Another solution of 4.75 grams of 3,4,4,4-tetrafluoro-3-trifluoromethyl butane-1-sulfonyl chloride, demonstrated above, in 15.0 mL of methylene chloride can be added, drop-wise under nitrogen, at such a rate as to keep the reaction temperature <5° C., (15 min., $T_{max}$=3.5° C.) to form a mixture. The mixture can be stirred for 1 hour at <5° C. The mixture can be filtered and the solids washed three times with 25 mL of methylene chloride. The solids can be identified by NMR to be 3,4,4,4-tetrafluoro-3-trifluoromethyl-1-butane-sulfonylamino)-acetic acid benzyl ester.

The 3,4,4,4-tetrafluoro-3-trifluoromethyl-1-butane sulfonylamino)-acetic acid benzyl ester (1.0 grams) can be dissolved in 10 mL of ethanol in a 250 mL Parr bottle. Palladium on carbon (10% (wt/wt), 50% (wt/wt) water Degussa type E101, 0.2 grams), can be added to the bottle to form a mixture. The bottle can be placed on a Parr shaker at 418 kPa and shaken overnight. The mixture can be sparged with nitrogen and filtered through a thin pad of Celite. The Celite can be rinsed three times with 20 mL of ethanol, and 1.18 mL of an aqueous 2N sodium hydroxide solution added to the combined filtrate and stirred. The filtrate can be concentrated under vacuum and dried to afford 0.803 grams (95.7%) of a white solid desired product that can be identified as

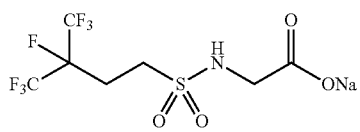

by NMR.

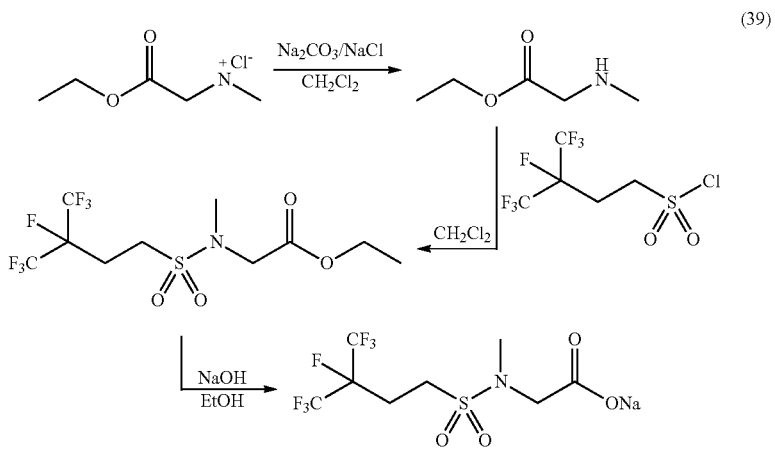

(39)

According to scheme (39) above, Sarcosine ethyl ester hydrochloride (7.68 grams) can be partitioned between 100 mL of methylene chloride and 200 mL of a 1:1 solution of 15% (wt/wt) aqueous sodium carbonate and brine. The layers can be separated and the bottom organic layer washed with 200 mL of a 1:1 solution of 15% (wt/wt) aqueous sodium carbonate and brine. The organic layer can be dried over sodium sulfate, filtered and concentrated under vacuum to afford 5.45 grams (93.0%) of a colorless oil that can be identified as sarcosine ethyl ester by NMR.

A solution of 5.45 grams of the sarcosine ethyl ester in 20.0 mL of methylene chloride in a three-necked, 100 mL round bottom flask equipped with a stir bar, addition funnel with a nitrogen inlet, and a thermocouple, can be chilled to 0° C.-5° C. in an ice bath. A solution of 6.91 grams of the 3,4,4,4-tetrafluoro-3-trifluoromethyl butane-1-sulfonyl chloride, described above, in 20.0 mL of methylene chloride can be added, drop-wise under nitrogen, at such a rate as to keep the reaction temperature <5° C., (45 min., $T_{max}$=2.1° C.) to form a mixture. The mixture can be stirred for 3 hours. <5° C., ($T_{max}$=3.7° C.) and washed two times with 20 mL of 5% (wt/wt) aqueous HCl solution and once with brine. The organic layer can be recovered, dried over sodium sulfate, filtered, and concentrated under vacuum to afford 7.78 grams of a light yellow oil that can be placed on a Kugelrohr and heated to 50° C., 0.01 Torr to remove the low boiling impurities and identified as [Methyl-(3,4,4,4-tetrafluoro-3-trifluoromethyl-butane-1-sulfonyl)-amino]-acetic ethyl ester (>96%) by NMR.

A solution of 6.8 grams of the [Methyl-(3,4,4,4-tetrafluoro-3-trifluoromethyl-butane-1-sulfonyl)-amino]-acetic ethyl ester in 25.0 mL of ethanol in a single necked, 100 mL round bottom flask can be treated with one equivalent of 2N sodium hydroxide (9.0 mL) to form a mixture. The mixture can be stirred at room temperature overnight, concentrated under vacuum, and placed on a Kugelrohr at 50° C., 0.01 Torr for 30 min. to afford 6.21 grams (93.0%)

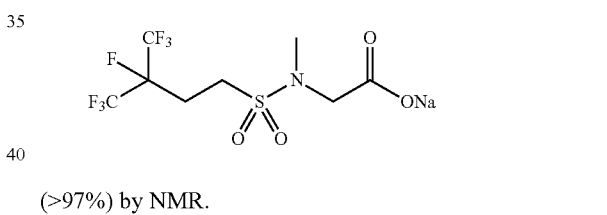

(>97%) by NMR.

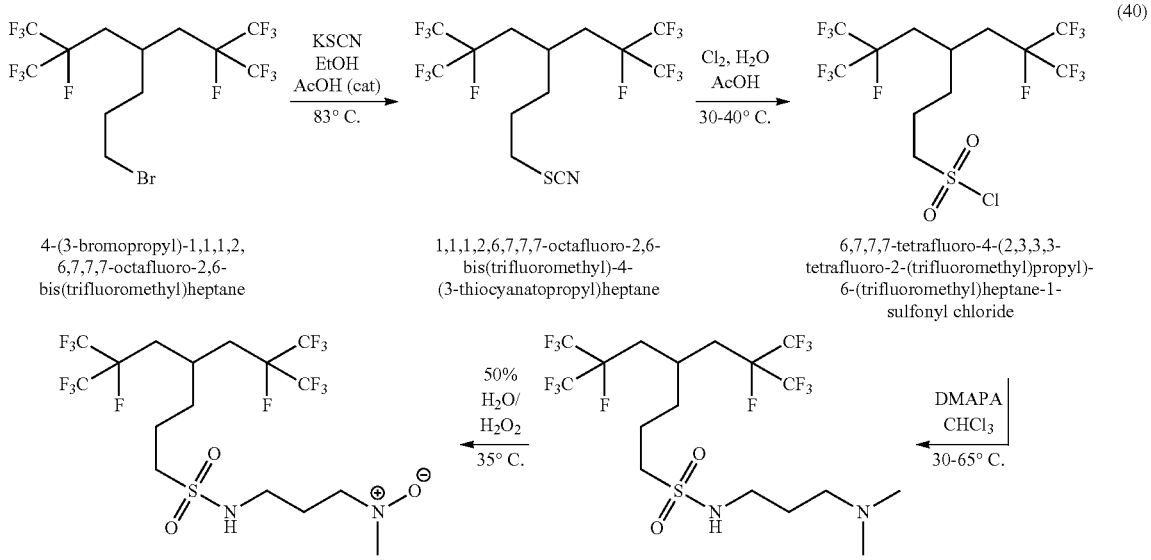

(40)

4-(3-bromopropyl)-1,1,1,2,6,7,7,7-octafluoro-2,6-bis(trifluoromethyl)heptane 1,1,1,2,6,7,7,7-octafluoro-2,6-bis(trifluoromethyl)-4-(3-thiocyanatopropyl)heptane 6,7,7,7-tetrafluoro-4-(2,3,3,3-tetrafluoro-2-(trifluoromethyl)propyl)-6-(trifluoromethyl)heptane-1-sulfonyl chloride In accordance with scheme (40) above, a solution of

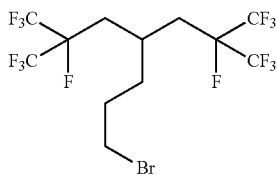

(876 grams), prepared according to scheme (24) above, and potassium thiocyanate (255 grams) can be dissolved in ethanol (880 mL) and acetic acid (35 mL) and heated to reflux and then refluxed for about 2.5 hours to form a heterogeneous mixture that can be cooled to room temperature and concentrated under vacuum to a yellow semi-solid. The semi-solid can be partitioned between methylene chloride (1 L) and deionzied water (1 L). The aqueous phase can be extracted with methylene chloride (500 mL) and the organic layers combined, dried over magnesium sulfate, filtered, and concentrated under vacuum to a yellow oil. The yellow oil can be placed briefly on the Kugelrohr at room temperature and 0.1 Torr to afford 828.3 grains (99.3%) of 97%

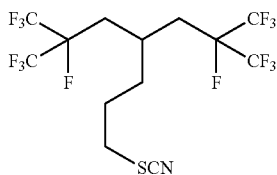

by NMR.

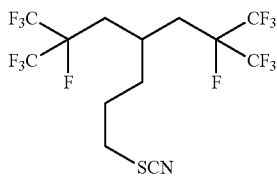

The (828.3 grams) can be dissolved in acetic acid (828 mL) to form a mixture. The mixture can be treated with 33 mL deionized water and sparged with chlorine and heated to 40° C. overnight with additional treatments of water. The temperature of the mixture can be increased to 50° C. and can be continued to be heated with a chlorine sparge for additional days to achieve approximately 80% completion. The mixture can be cooled to room temperature and quenched using methylene chloride (2 L) and deionized water (2 L). The organic layer can be washed three times with deionized water (1 L each). The organic layer can be then dried over magnesium sulfate overnight. The dried organic layer can be filtered and concentrated under vacuum to a colorless oil (862.4 grams), and the oil can be dissolved in acetic acid (850 mL) to form a mixture. This mixture can be heated to 50° C. with a chlorine sparge, and deionized water (33 mL) can be added once the reaction reaches 50° C. The mixture can be allowed to cool to room temperature and quenched using methylene chloride (2 L) and deionized water (1 L). The organic layer can be washed three times with deionized water (1 L each) and then dried over magnesium sulfate overnight. The dried organic layer can be filtered and concentrated under vacuum to a colorless oil (859.6 grams, 95.4%) NMR and gas chromatography analysis can indicate (97%, area percent)

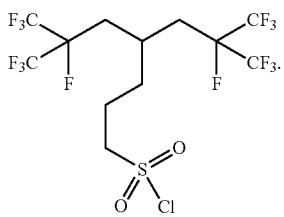

Dimethylaminopropylamine (568 mL) and chloroform (4 L) can be combined to form a mixture and cooled to 0° C. using an ice/acetone bath and

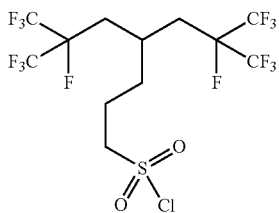

(839 grains) can be dissolved in chloroform (4 L) and added drop-wise to the mixture over four hours to keep the mixture at temperature <0° C. The reaction can be completed an hour after the drop-wise addition to form a yellow solution. The homogeneous yellow reaction solution can be washed with saturated bicarbonate (8 L) deionized water (8 L), and brine (8 L) and the organic layer dried over magnesium sulfate, filtered, and concentrated in vacuum to a white solid. The white solid can be dried for one hour under vacuum at 35° C. to afford 899.7 (95.2%, area percent) of

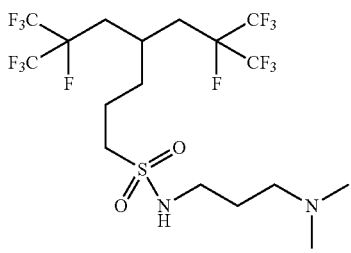

by NMR.
The

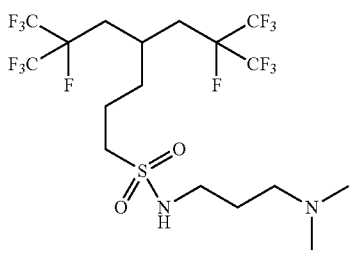

(600 grams) can be dissolved in ethanol (820 mL) and water (130 mL) with 50% (wt/wt) hydrogenperoxide (241 mL) to form a mixture and heated to 35° C. exotherm with a $t_{max}$=49.3° C. can be observed. The reaction can be complete an hour after heating the mixture as determined by NMR analysis, however, by LC/MS analysis a trace amount of starting material can be observed. The mixture can be heated again at 35° C. for two hours to complete the reaction. Decolorizing carbon (135 grams) and ethanol (820 mL) can be added to the mixture portion-wise and the mixture heated to 50° C. An exotherm can be observed. The mixture can be allowed, to stir at ambient temperature overnight. The reaction can be tested for peroxide using KI starch test strips, and if positive, the mixture can be heated to 50° C. for 1.5 hours or until negative. The mixture can then be filtered through celite and the celite pad washed using 1 L ethanol. The filtrate can be concentrated to a white solid and the white solid placed on the Kugelrohr for 30 minutes at 0.1 Torr and 50° C. The white solid can then be dried under vacuum at 50° C. for four hours to afford 593.8 grams (96.6%) of 6,7,7,7-tetrafluoro-4-(2,3,3,3-tetrafluoro-2-trifluoromethyl-propyl)-6-trifluoromethyl-heptane-1-sulfonyl amine by NMR and/or LC/MS.

The 6,7,7,7-Tetrafluoro-4-(2,3,3,3-tetrafluoro-2-trifluoromethyl-propyl)-6-trifluoromethyl-heptane-1-sulfonyl amine (319 grams), ethanol (1290 mL), and sodium chloroacetate (63.5 grams) can be combined to form a mixture and the mixture brought to reflux for 48 hours. After 48 hours, NMR analysis can indicate that no starting material is present, however, LC/MS analysis may indicate product ions. The mixture can be filtered and the filter cake washed with ethanol (1 L). The filtrate can be concentrated under vacuum to an orange foam and the orange foam placed on the Kugelrohr at 0.1 Torr and 50° C. for one hour. The orange foam like solid can be dried overnight under vacuum at 50° C. to afford 344.4 grams (98.2%) of

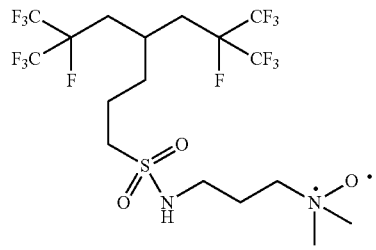

as demonstrated by NMR.

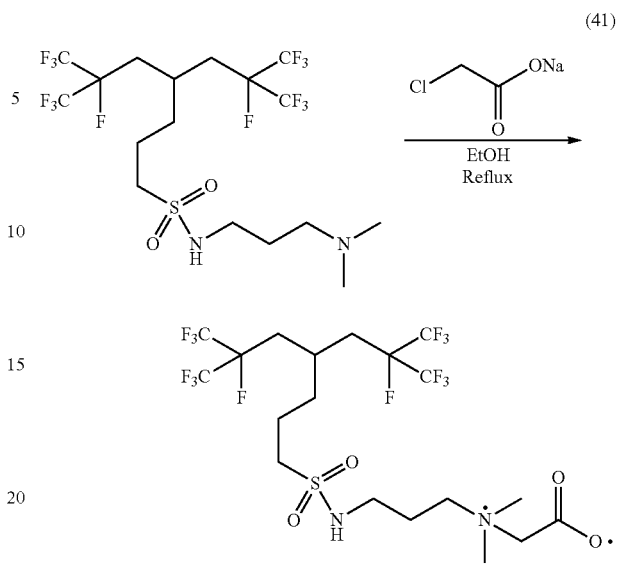

(41)

In accordance with scheme (41) above, 6,7,7,7-Tetrafluoro-4-(2,3,3,3-tetrafluoro-2-trifluoromethyl-propyl)-6-trifluoromethyl-heptane-1-sulfonic acid (3-dimethylaminopropyl)-amide (6.2 grams) can be dissolved in 25 mL of ethanol containing 1.23 grams of sodium chloroacetate to form a solution. The solution can be heated to reflux and allowed to reflux overnight. After refluxing for approximately 2 days, the solution can be quenched, filtered, and the filtrate stripped of solvent overnight in a vacuum (50° C., 1 Torr). The remaining solids can be identified as

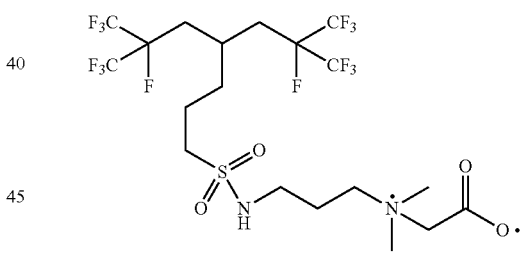

by NMR.

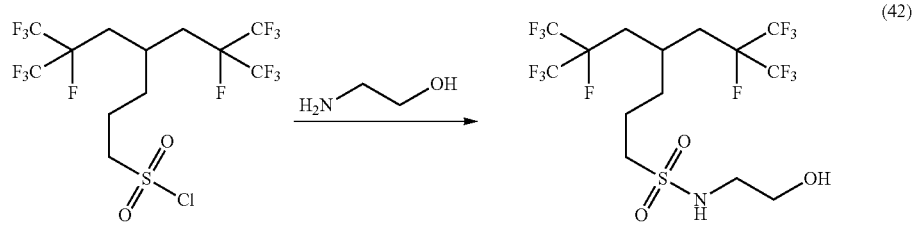

(42)

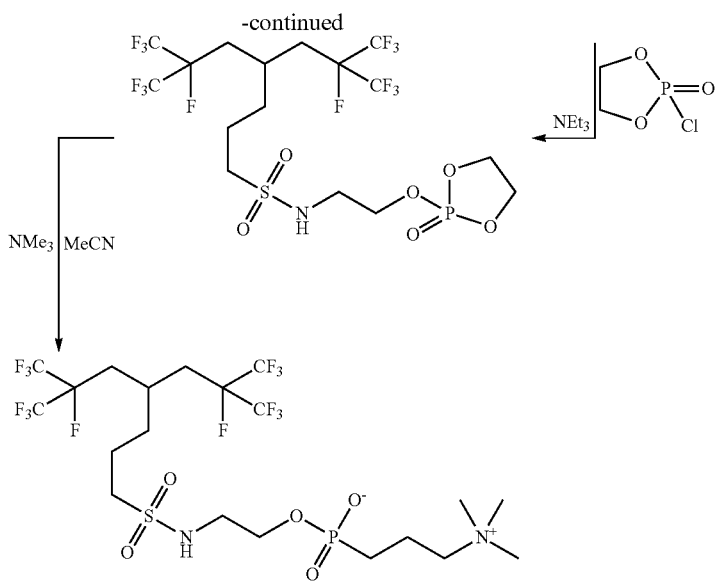

Referring to scheme (42) above, a solution of the 6,7,7,7-tetrafluoro-4-(2,3,3,3-tetrafluoro-2-trifluoromethyl-propyl)-6-trifluoromethyl heptane-1-sulfonyl chloride (25 grams), described above, in 125 mL dichloromethane can be added to a cooled solution (0° C.-5° C.) of ethanolamine (17.6 grams) in dichloromethane (125 mL) drop-wise to form a mixture. The mixture can be agitated, allowed to warm to room temperature, and diluted with dichloromethane (250 mL). The diluted mixture can be washed with deionized water (250 mL). 5% (wt/wt) HCl (250 mL), and saturated bicarbonate solution (250 mL). The organic layer can be separated, dried over sodium sulfate, filtered, and concentrated under vacuum to afford 6,7,7,7-tetrafluoro-4-(2,3,3,3-tetrafluoro-2-trifluoromethyl-propyl)-propyl)-6-trifluoromethyl-heptane-1-sulfonic acid (2-hydroxy-ethyl)-amide (5.0 grams) with residual dichloromethane and ethanolamine by NMR analysis.

A solution of the 6,7,7,7-tetrafluoro-4-(2,3,3,3-tetrafluoro-2-trifluoromethyl-propyl)-6-trifluoromethyl-heptane-1-sulfonic acid (2-hydroxy-ethyl)-amide (5.0 grams) and 2-chloro-[1,3,2]dioxaphospholane-2-oxide (0.87 mL) can be dissolved in anhydrous ether (30 mL) and cooled to 0° C. using an ice/water bath. Triethylamine (0.55 mL) can be added drop-wise to the solution to form a white precipitate. The solution can be allowed to warm to room temperature, filtered, and concentrated under vacuum. The reaction can appear to be decomposing after 6 hours. The bulk solution can be filtered and concentrated under vacuum to a yellow oil (3.3 grams) that can be identified as

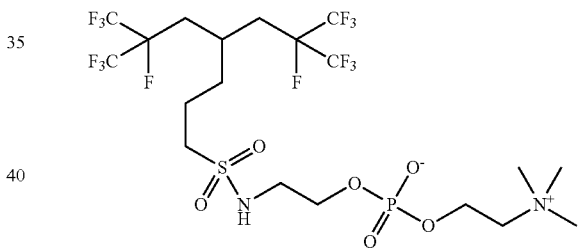

by NMR and/or LC/MS analysis.

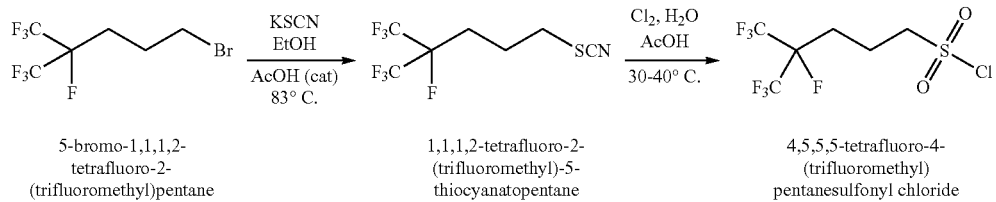

| 5-bromo-1,1,1,2-tetrafluoro-2-(trifluoromethyl)pentane | 1,1,1,2-tetrafluoro-2-(trifluoromethyl)-5-thiocyanatopentane | 4,5,5,5-tetrafluoro-4-(trifluoromethyl)pentanesulfonyl chloride |

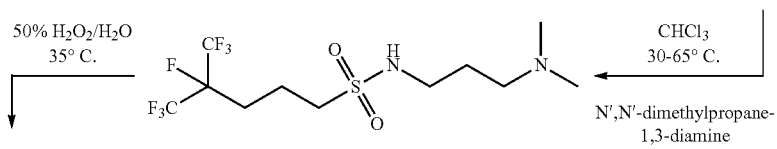

N',N'-dimethylpropane-1,3-diamine

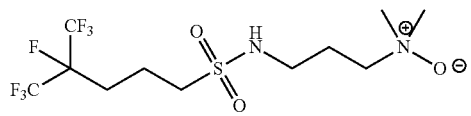

-continued

In accordance with scheme (43) above, 5-bromo-1,1,1,2-tetrafluoro-2-trifluoromethyl-pentane (25 grams) can be dissolved in 25 mL of ethanol and 0.2 mL of acetic acid, and 10.9 grams of potassium thiocyanate can be added to form a mixture. The mixture can be heated to reflux and cooled to room temperature after about 1 to 2.5 hours, and concentrated under vacuum. The concentrate can be partitioned between methylene chloride (100 mL) and water (50 mL). The aqueous phase can be extracted with methylene chloride (50 mL), the organic layers combined, dried over magnesium sulfate, filtered, and concentrated under vacuum to afford a yellow oil that can be identified as 1,1,1,2-tetrafluoro-5-thiocyanato-2-trifluoromethyl-pentane (21.7 grains, 93.9%) by NMR analysis.

The 1,1,1,2-tetrafluoro-5-thiocyanato-2-trifluoromethyl-pentane can be dissolved in 10 mL of acetic acid and 0.4 mL of water, heated to 40° C. and sparged with chlorine. Three additional water (0.4 mL) treatments can be added every 2 hours with a slight temperature exotherm noted after each addition. The mixture can be sparged and additional water treatments added for a couple of days to result in a heterogenous mixture. The heterogeneous mixture can be partitioned between methylene chloride (100 mL) and water (25 mL), the organic layer dried over magnesium sulfate, filtered, and concentrated under vacuum. NMR analysis can indicate 7.1 grams (74.1%) of 4,5,5,5-tetrafluoro-4-trifluoromethyl-pentanesulfonyl chloride.

The 4,5,5,5-tetrafluoro-4-trifluoromethyl-pentanesulfonyl chloride (7.1 grams) can be dissolved in 40 mL of chloroform and added to a solution of 8.6 mL 3-dimethylaminopropylamine in 40 mL of chloroform at 0° C.-5° C. drop-wise over 45 minutes ($T_{max}$=5° C.) to form a mixture. The mixture can be washed successively with saturated bicarbonate solution (80 mL), water (80 mL), and brine (80 mL). The organic layer can be separated, dried over magnesium sulfate, filtered, and concentrated under vacuum to afford
8 grams (93%) of 4,5,5,5-tetrafluoro-4-trifluoromethyl-pentane-1-sulfonic acid (3-dimethylamino-propyl)-amide by NMR and LC/MS analysis.

The 4,5,5,5-tetrafluoro-4-trifluoromethyl-pentane-1-sulfonic acid (3-dimethylamino-propyl)-amide (8 grams) can be dissolved in 25 mL of ethanol containing 3 mL of water and 5.1 mL of 50% (wt/wt) hydrogen peroxide and the resulting solution heated at 35° C. for 30 minutes. The reaction can then be allowed to cool to room temperature overnight. Norit, a decolorizing carbon (10 grams) and ethanol (20 mL) can be added and the mixture heated to 50° C. for 3 hours. The mixture can be filtered through celite, the filter cake washed with 90% (wt/wt) ethanol/10% (wt/wt) water (60 mL), and the filtrate concentrated under vacuum, distilled with methanol, and Kugelrohr to afford 7.1 grams (89.9%) of

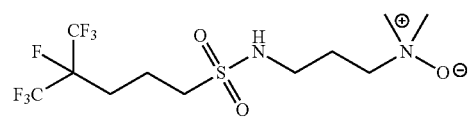

by NMR and LCMS analysis.

(44)

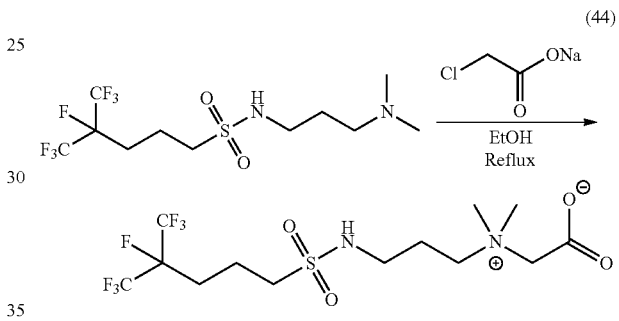

In accordance with scheme (44) above, 4,5,5,5-Tetrafluoro-4-trifluoromethyl-pentane-1-sulfonic acid (3-dimethylamino-propyl)-amide (6.0 grams) can be dissolved in 25 mL of ethanol containing 1.9 grams of sodium chloroacetate. The resulting solution can be heated to reflux and allowed to reflux for two consecutive nights. After refluxing for approximately 45 hours, the reaction can be stopped, filtered, the salts rinsed and discarded and the filtrate stripped of solvent and identified as

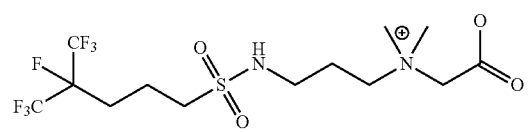

(3.6 grams) by NMR.

(45)

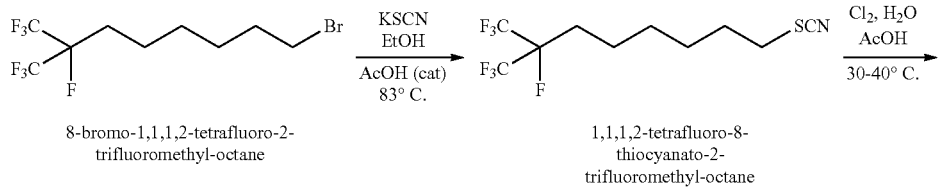

8-bromo-1,1,1,2-tetrafluoro-2-trifluoromethyl-octane 1,1,1,2-tetrafluoro-8-thiocyanato-2-trifluoromethyl-octane

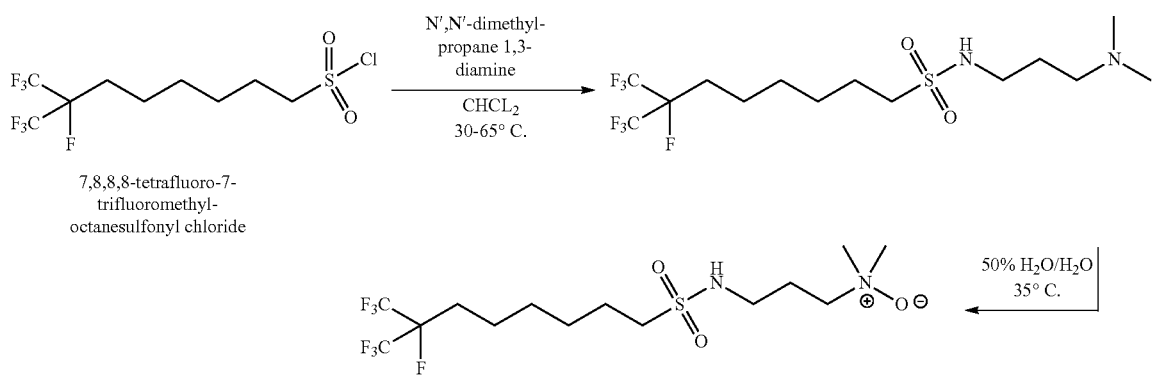

7,8,8,8-tetrafluoro-7-trifluoromethyl-octanesulfonyl chloride

In accordance with scheme (45) above, 8-Bromo-1,1,1,2-tetrafluoro-2-trifluoromethyl-octane (20 grams) can be dissolved in 30 mL of ethanol containing 7.6 grams of potassium thiocyanate. Acetic acid (0.2 mL) can be added to form a mixture and the mixture heated to reflux for 4 hours. The mixture can be allowed to cool to room temperature overnight, concentrated under vacuum, and partitioned between methylene chloride (200 mL) and water (100 mL). The organic layer can be dried over magnesium sulfate, filtered, and concentrated under vacuum to afford 18.2 grams (97%) 1,1,1,2-tetrafluoro-8-thiocyanato-2-trifluoromethyl-octane by NMR analysis.

The 1,1,1,2-tetrafluoro-8-thiocyanato-2-trifluoromethyl-octane (18.2 grams) can be dissolved in 25 mL of acetic acid to form a mixture and the mixture heated to 40° C. with chlorine sparging. Initially, 0.8 mL of water can be added to the mixture. Three additional water treatments (0.8 mL/each) can be added to the mixture every 2 hours and heated with the chlorine sparge continued overnight and an additional 0.8 mL of water added, the mixture can be cooled and partitioned between methylene chloride (200 mL) and water (100 mL). The aqueous layer can be extracted with methylene chloride (100 mL). The organic layers can be combined, washed three times with water (100 mL/each), dried over magnesium sulfate, filtered, and concentrated to yield 19.5 grams (94.5%) of 7,8,8,8-tetrafluoro-7-trifluoromethyl-octanesulfonyl chloride by NMR analysis.

The 7,8,8,8-tetrafluoro-7-trifluoromethyl-octanesulfonyl chloride (19.5 grams) can be dissolved in 100 mL of chloroform and added to 20.9 mL of dimethylaminopropylamine in 100 mL of chloroform at 0° C.-5° C. over 1 hour to form a mixture. When the addition is complete, the mixture can be allowed to warm to room temperature and can be stirred at ambient for one hour. The mixture can be washed twice with saturated bicarbonate solution (100 mL/each), deionized water (200 mL), and brine (200 mL). The organic layer can be dried over magnesium sulfate, filtered, and concentrated under vacuum to afford a yellow oil that can be identified as 7,8,8,8-tetrafluoro-7-trifluoromethyl-octane-1-sulfonic acid (3-dimethylamino-propyl)-amide (24.09 grams, 95.97%) by NMR.

The 7,8,8,8-tetrafluoro-7-trifluoromethyl-octane-1-sulfonic acid (3-dimethylamino-propyl)-amide (7 grams) can be dissolved in 25 mL of ethanol containing 2.3 mL of water and 4.0 mL of 50% (wt/wt) hydrogen peroxide and the resulting solution can be heated at 35° C. overnight. Decolorizing carbon (8 grams) and ethanol (15 mL) can be added to the solution and the solution heated to 50° C. for three hours. The solution can then be cooled to room temperature, filtered through celite, the filter cake washed with 90% (wt/wt) ethanol/deionized water (50 mL), and the filtrate concentrated under vacuum to a wax like solid. The solid can be distilled twice with ethanol to afford a yellow oil that can be placed on a Kugelrohr for two hours at 40° C. and 0.1 Torr to afford a white solid (5.9 grams, 79.9%) of

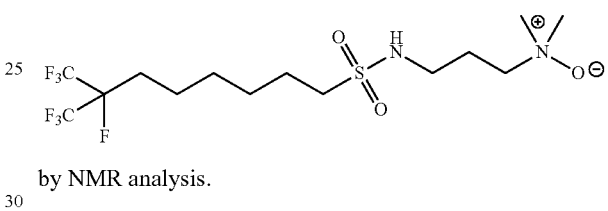

by NMR analysis.

(46)

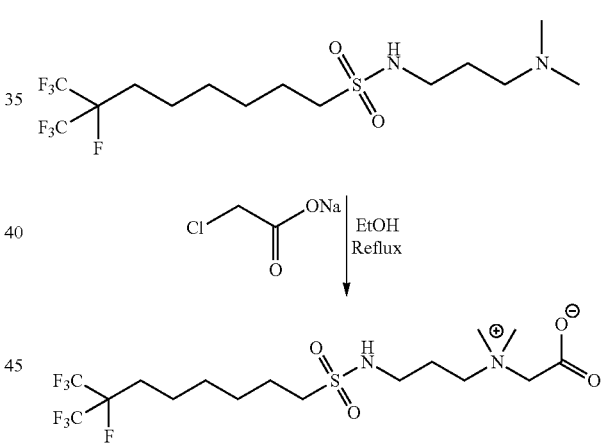

In accordance with scheme (46) above, 7,8,8,8-tetrafluoro-7-trifluoromethyl-octane-1-sulfonic acid (3-dimethylaminopropyl)-amide (6.0 grams) can be dissolved in 25 mL of ethanol containing 1.6 grams of sodium chloroacetate. The resulting solution can be heated to reflux and allowed to reflux and stir over for 40 hours. The solution can be quenched, filtered, the solvent stripped, and the resulting solid placed in a drying oven (50° C., 1 Torr) overnight. The remaining solids can be identified as

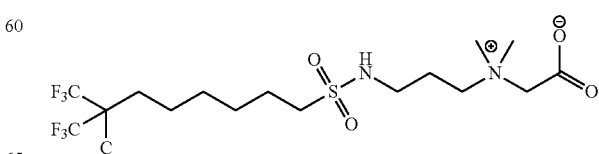

by NMR.

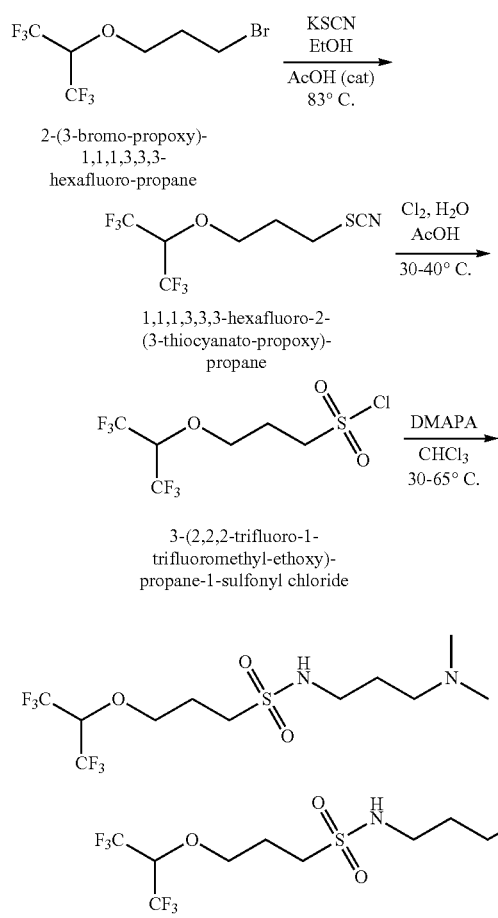

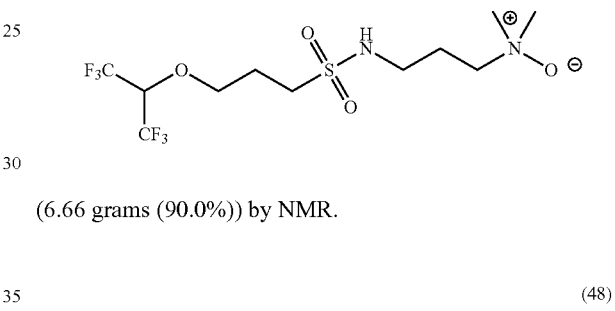

In accordance with scheme (47) above, 2-(3-Bromo-propoxy)-1,1,1,3,3 hexafluoro-propane (19 grams) and potassium thiocyanate (8.3 grams) can be dissolved in 30 mL of ethanol containing 0.2 mL of acetic acid and heated to reflux. After 2.5 hours at reflux, the reaction mixture can be cooled to room temperature and concentrated under vacuum to a semi solid. The semi solid can be partitioned between ether (100 mL) and deionized water (100 mL). The organic layer can be dried over sodium sulfate, filtered, and concentrated under vacuum to afford a yellow oil (16.88 grams, 90.3%). The yellow oil can be identified as 1,1,1,3,3,3-hexafluoro-2-(3-thiocyanato-propoxy)-propane by NMR.

The 1,1,1,3,3,3-hexafluoro-2-(3-thiocyanato-propoxy)-propane (16.9 grams) can be dissolved in 30 mL of acetic acid and 0.8 mL of water to form a mixture. The mixture can be heated to 40° C. and sparged with chlorine. The mixture can then be treated three times with deionized water (0.8 mL) every two hours, and the mixture heated to 40° C. under a chlorine sparge for about 48 hours. The mixture can be allowed to cool to room temperature, partitioned between methylene chloride (100 mL) and deionized water (100 mL), the organic layer separated and washed three times with deionized water (100 mL/each), dried over magnesium sulfate, filtered, and concentrated under vacuum to a colorless oil 3-(2,2,2-trifluoro-1-trifluoromethyl-ethoxy)-propane-1-sulfonyl chloride (18.4 grams, 99.3%) by NMR.

The 3-(2,2,2-trifluoro-1-trifluoromethyl-ethoxy)-propane-1-sulfonyl chloride (18.4 grams) can be dissolved in 100 nit of chloroform and added to 22.5 mL of dimethylaminopropylamine in 100 mL of chloroform at 0° C.-5° C. over 1 hour to form a mixture. When the addition is complete the mixture can be allowed to warm to room temperature and stir at ambient for 1 hour. The mixture can be washed with saturated bicarbonate solution (200 mL), deionzied water (200 mL), and brine (200 mL). The organic layer can be dried over magnesium sulfate, filtered, and concentrated under vacuum to afford a yellow oil that can be placed on the Kugelrohr for 15 minutes at ambient temperature and 0.1 Torr to afford 3-(2,2,2-trifluoro-1-trifluoromethyl-ethoxy)-propane-1-sulfonic acid (3-dimethylamino-propyl)-amide (20.88 g (92.8%)) by NMR.

The 3-(2,2,2-trifluoro-1-trifluoromethyl-ethoxy)-propane-1-sulfonic acid (3-dimethylamino-propyl)-amide (7 grams) can be dissolved in 25 mL of ethanol containing 2.6 mL of water and 4.4 mL of 50% (wt/wt) hydrogen peroxide to form a mixture and the mixture heated at 35° C. overnight. Decolorizing carbon (8 grams) and ethanol (15 mL) can be added to the mixture, the mixture heated to 50° C. for 3 hours, filtered through celite, the filter cake washed with 90% (wt/wt) ethanol/water (50 mL) and the filtrate can be concentrated under vacuum to afford a white semi-solid. The solid can be refluxed twice in ethanol prior to being placed on the Kugelrohr for 1 hour at 40° C. and 0.1 Torr to afford

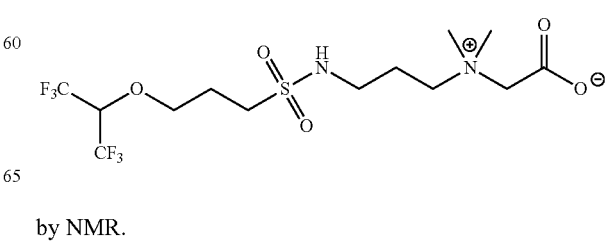

(6.66 grams (90.0%)) by NMR.

In accordance with scheme (48) above, 3-(2,2,2-trifluoro-1-trifluoromethyl-ethoxy)-propane-1-sulfonic acid (3-dimethylamino-propyl)-amide (6.0 grams) can be dissolved in 25 mL of ethanol containing 1.9 grams of sodium chloroacetate. The resulting solution can be refluxed and stirred for 40 hours, the reaction quenched, and filtered. The solvent can be stripped and the resulting solid placed in a drying oven (50° C., 1 Torr) overnight to yield by NMR.

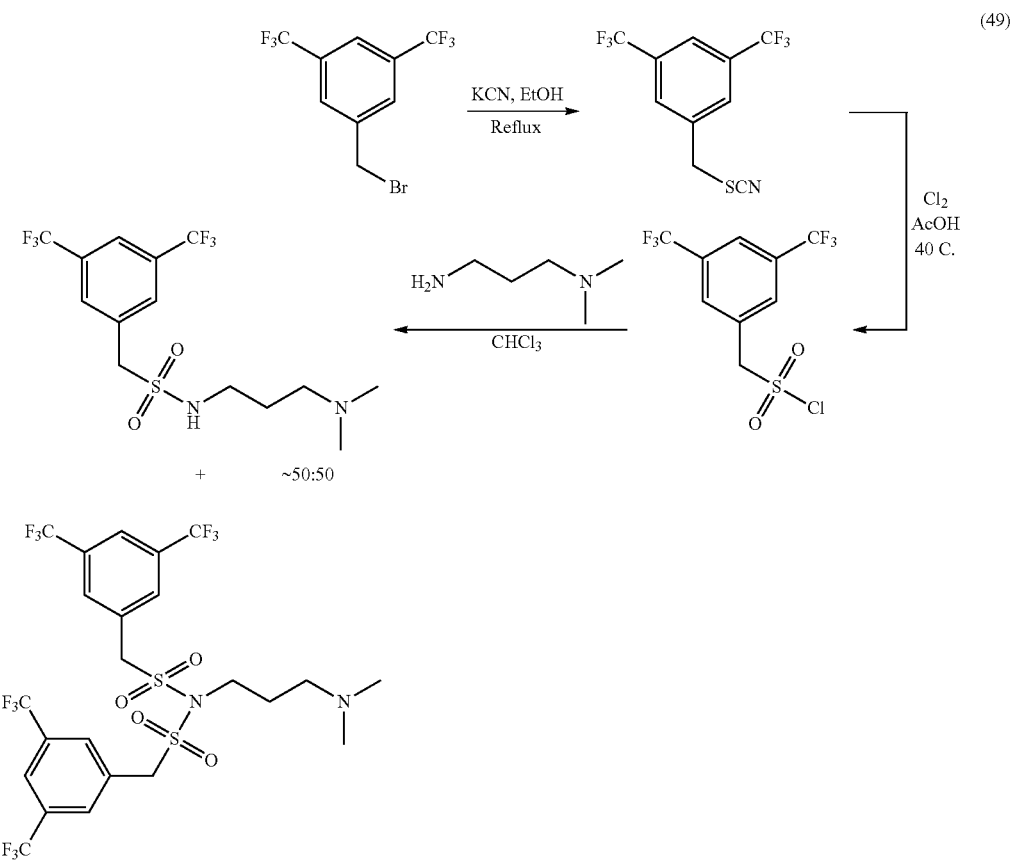

(49)

In accordance with scheme (49) above, a solution of 3,5-bis(trifluoromethyl)benzyl bromide (25 g) and 11.9 grains of potassium thiocyanate can be dissolved in 40 mL ethanol and 0.2 mL of acetic acid and heated to reflux, allowed to reflux for 3 hours, cooled to room temperature, and concentrated under vacuum to yield a white solid. The solid can be partitioned between ether (150 mL) and deionized water (150 mL). The organic layer can be dried over sodium sulfate, filtered, and concentrated under vacuum to afford 1,1,1,2-tetrafluoro-5-thiocyanato-2-trifluoromethyl-pentane (23.1 grains, 98.8%) NMR analysis.

The 1,1,1,2-tetrafluoro-5-thiocyanato-2-trifluoromethyl-pentane (23.1 grams) can be dissolved in 33 mL acetic and heated to 40° C. with chlorine sparging overnight to yield a white precipitate. The heterogeneous mixture can be allowed to cool to room temperature, partitioned between deionized water (150 mL) and methylene chloride (150 mL). The organic layer can be washed three times with deionized water (100 mL), dried over magnesium sulfate, filtered, and concentrated under vacuum to afford a white solid that can be placed on the Kugelrohr at 0.1 Torr and 40° C. for 30 minutes. NMR analysis can indicate 3,5-bis-trifluoromethyl phenyl)-methanesulfonyl chloride (18.52 grams, 70.1%).

The 3,5-bis-trifluoromethylphenyl)-methanesulfonyl chloride (18.5 grams) can be dissolved in 100 mL of chloroform and cooled to 0° C.-5° C., then 20 mL of 3-dimethylaminopropylamine can be added in 100 mL of chloroform drop-wise over. 1 hour. The mixture can be allowed to warm to room temperature and stir at ambient temperature for 3 hours. The reaction can then be washed with saturated bicarbonate solution (200 mL), deionized water (200 mL), and brine (200 mL). The organic layer can be separated, dried over magnesium sulfate and concentrated under vacuum to a yellow solid (20.0 grams). NMR analysis can indicate the yellow oil is 1:1 mono and bis sulfonyl amine products.

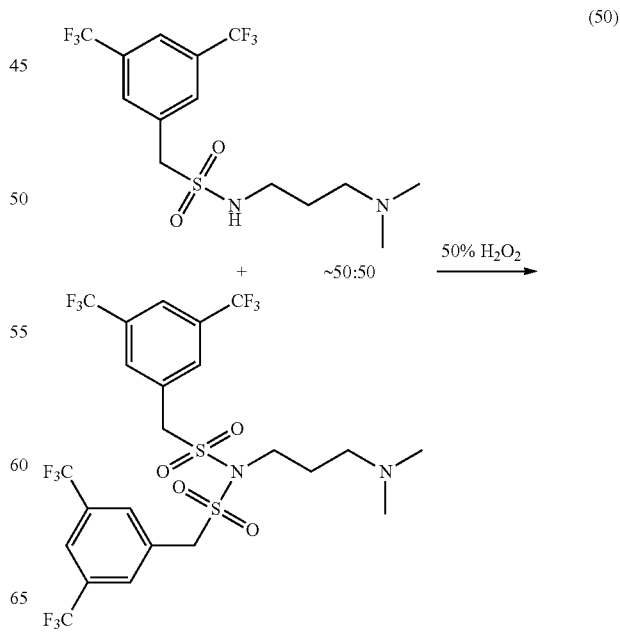

(50)

-continued

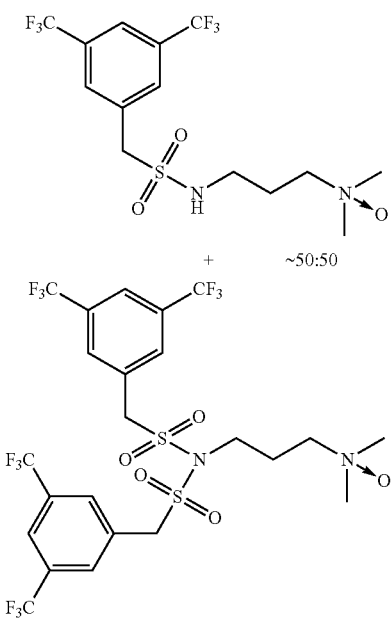

~50:50

Referring to scheme (50) above, the mono and bis sulfonyl amine starting material (10 grams) can be dissolved in 30 mL ethanol, deionized water (3.7 mL) and 50% (wt/wt) hydrogen peroxide (4.7 mL). The heterogeneous mixture can be allowed to stir at ambient temperature over 2 days and decolorizing carbon (7 grams) and ethanol (15 mL) added to the mixture. The mixture can be stirred over 2 days at room temperature, monitored for peroxide, the bulk reaction filtered through celite, the filter cake washed with 90% (wt/wt) ethanol, water (50 mL), and the filtrate concentrated under vacuum to afford a yellow solid (7.07 grams). The yellow solid can be identified as 1:1 mono/bis product by NMR and/or LC/MS analysis.

Referring to scheme (51) above, a solution of 3,5-bis(trifluoromethyl)benzyl bromide (25 grams) and 11.9 grams of potassium thiocyanate can be suspended in 40 mL of ethanol and 0.2 mL of acetic acid and heated to reflux, refluxed for 3 hours, allowed to cool to room temperature, and then concentrated under vacuum to afford a white solid. The white solid can be partitioned between ether (100 mL) and deionized water (100 mL). The organic layer can be separated, dried over sodium sulfate, filtered, and concentrated under vacuum to afford 1,1,1,2-tetrafluoro-5-thiocyanato-2-trifluoromethyl-pentane (22.58 grams, 96.6%), that can be identified by NMR.

The 1,1,1,2-tetrafluoro-5-thiocyanato-2-trifluoromethyl-pentane (22.5 grams) can be dissolved in 32 mL acetic acid and heated to 50° C. with chlorine sparging overnight. The reaction mixture can be allowed to cool to room temperature, partitioned between methylene chloride (100 mL) and deionized water (100 mL), the organic layer washed thrice with deionized water (100 mL/each), dried over magnesium sulfate, filtered, and concentrated under vacuum to yield a white solid of 3,5-bis-trifluoromethyl phenyl-methanesulfonyl chloride (22.94 grams, 89.1%) that can be determined by NMR.

The 3,5-bis-trifluoromethyl phenyl)-methanesulfonyl chloride (5 grams) can be dissolved in 25 mL of chloroform and added to a cooled (0° C.-5° C.) solution of 4.4 mL of 3-dimethylaminopropylamine in 25 mL of chloroform dropwise over 1 hour, then allowed to warm to room temperature after the addition is complete. The homogeneous solution can be washed with saturated bicarbonate solution (50 mL), deionized water (50 mL), and brine (50 mL). The organic layer can be separated, dried over magnesium sulfate, filtered, and concentrated under vacuum to afford a yellow solid (5.26 grams, 87.7%), that can be determined by NMR analysis to be 90% C-(3,5-bis-trifluoromethyl-phenyl)-N-(3-dimethylamino-propyl)-methanesulfonamide with the impurity being the bis addition compound.

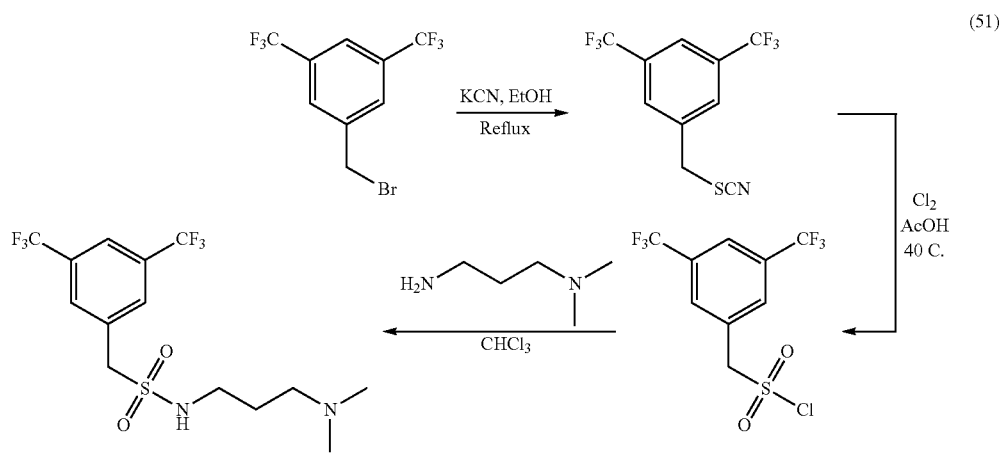

(51)

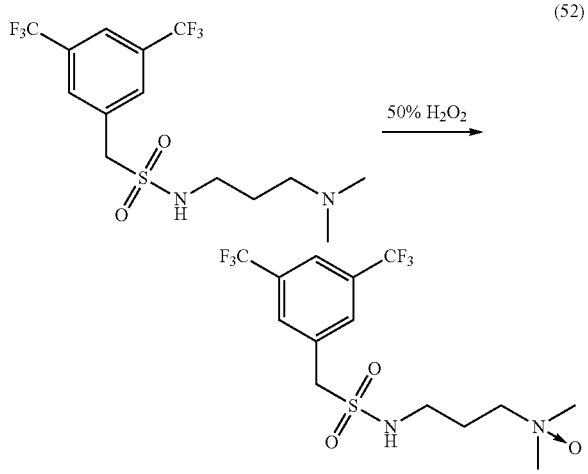

Referring to scheme (52) above, the C-(3,5-Bis-trifluoromethyl-phenyl)-N-(3-dimethylamino-propyl)-methanesulfonamide (6 grams) can be dissolved in 20 mL ethanol, deionized water (2.2 mL) and 50% (wt/wt) hydrogen peroxide (3.6 mL), and the heterogeneous mixture allowed to stir at ambient temperature overnight. The mixture can then be cooled, decolorizing carbon (5 grams) and ethanol (15 mL) added, heated to 50° C. for 2 hours, monitored for peroxide, cooled to room temperature, and filtered through celite. The filter cake can be washed with 90% (wt/wt) ethanol, 10% (wt/wt) water (50 mL), and the filtrate concentrated under vacuum to afford C-(3,5-bis-trifluoromethyl-phenyl)-N-(3-dimethylamino-propyl)-methanesulfonamide by NMR analysis.

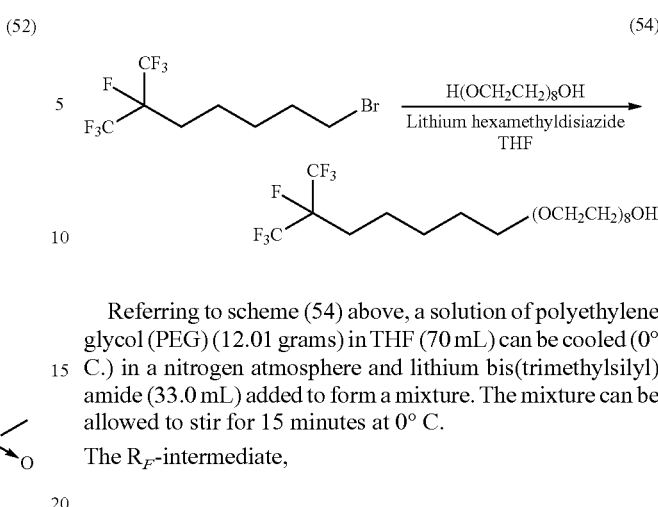

Referring to scheme (54) above, a solution of polyethylene glycol (PEG) (12.01 grams) in THF (70 mL) can be cooled (0° C.) in a nitrogen atmosphere and lithium bis(trimethylsilyl) amide (33.0 mL) added to form a mixture. The mixture can be allowed to stir for 15 minutes at 0° C.

The $R_F$-intermediate,

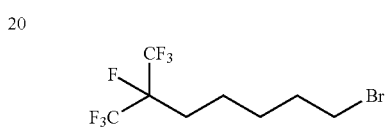

can be then placed in THF (70 mL) and added drop-wise to the mixture. The mixture can be allowed to stir at 0° C. for 30 minutes, then allowed to warm to room temperature and stir for an hour. The mixture can then be heated to 40° C. and allowed to stir overnight to form a clear light tan solution, which can have a small amount of suspended solid matter, that can be acidified with HCl (5% (wt/wt), 135 mL) until pH=3. The solids can be dissolved into solution at pH=9 and the mixture turned a clear yellow. The biphasic solution can be

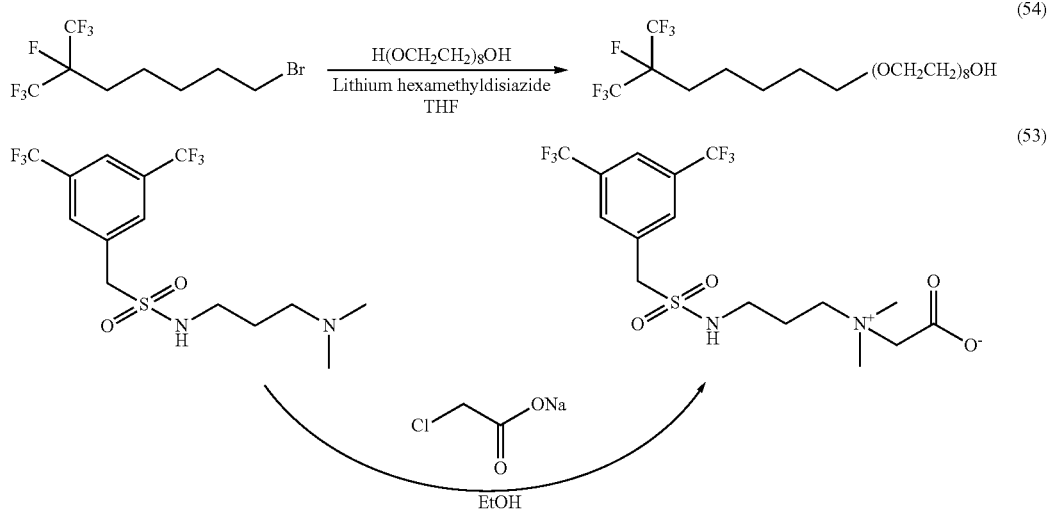

Referring to scheme (53) above, the C-(3,5-bis-trifluoromethyl-phenyl)-N-(3-dimethylamino-propyl)-methanesulfonamide (2 grains) can be dissolved in ethanol (20 mL), and sodium chloroacetate (0.59 grams) and refluxed overnight, the reaction allowed to cool to room temperature, filtered, and the filtrate concentrated under vacuum to a white solid. The white solid can be placed on the Kugelrohr at 0.1 Torr and 50° C. for 1 hour to afford 2.1 grams (91.3%) by NMR analysis.

separated, the aqueous layer set aside, the organic layer dried over $Na_2SO_4$, filtered, and stripped of solvent. The resulting yellow oil can be placed on the Kugelrohr (40° C., 0.1 Torr. 15 minutes) to remove residual solvent. $^1$HNMR analysis of the heterogeneous yellow oil (8.1 grams) can be identified as a mixture of starting material and PEG, not desired product, as the LC/MS can suggest. The yellow oil can be distilled on the Kugelrohr and the remains determined to be desired product (1.8 grams) by NMR and/or LC/MS.

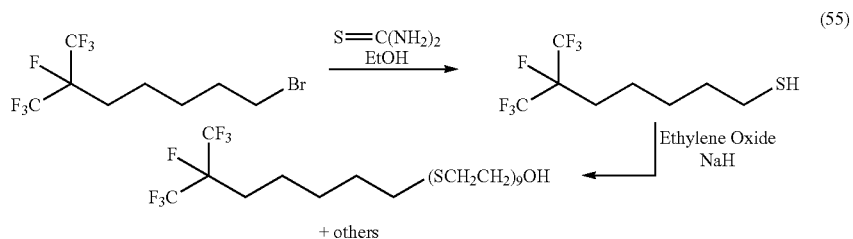

(55)

Referring to scheme (55) above, the $R_F$-intermediate

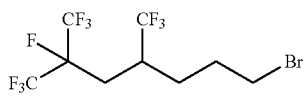

can be combined with thiourea (0.68 grams) in ethanol (25 mL) and heated to reflux overnight. After 22 hours of refluxing, the reaction system can be dismantled, the ethanol stripped, and the remaining oil placed on the Kugelrohr (0.01 mmHg, 20 min, 60° C.) which can yield 7,8,8,8-tetrafluoro-7-trifluoromethyl-octane-1-thiol (3.4 grams) that can be determined by NMR and/or LC/MS analysis.

The 7,8,8,8-tetrafluoro-7-trifluoromethyl-octane-1-thiol can be placed in a flask and cooled to 0° C. and NaH (0.08 grams) added to form a mixture. The mixture can be cooled to −78° C., flushed with nitrogen, condensed in ethylene oxide (1.6 grams), and allowed to warm to room temperature, then placed in a 65° C. oil bath overnight. Ethyl acetate (20 mL) and HCl (1N, 10 mL) can be added to the mixture, the layers separated, the aqueous layer extracted with ethyl acetate (20 mL, 5 times). All organic layers can be combined, dried over $Na_2SO_4$, filtered, stripped of solvent and the resulting brown oil (2.2 grams) characterized LC/MS analysis.

potassium thiocyanate (8.7 grams), ethanol (40 mL), and acetic acid (0.2 mL) can be combined and brought to reflux, refluxed for 3 hours, and the heterogeneous mixture allowed to cool to room temperature and concentrated under vacuum to yield a white/yellow semi-solid. The semi-solid can be partitioned between ether (100 mL) and deionized water (100 mL). The organic layer can be separated, dried over sodium sulfate, filtered, and concentrated under vacuum to afford an orange oil (21.19 grams, 97.2%) that can be identified as 1,1,1,2-tetrafluoro-7-thiocyanato-2,4-bistrifluoromethyl-heptane (>95% pure) by NMR and gas chromatography analysis.

The 1,1,1,2-tetrafluoro-7-thiocyanato-2,4-bistrifluoromethyl-heptane can be dissolved in 30 mL acetic acid and heated to 40° C. with chlorine sparging overnight. The temperature of the mixture can be increased to 50° C. for 6 hours and allowed to cool to room temperature. The mixture can be partitioned between methylene chloride (100 mL) and deionized water (100 mL), the organic layer can be separated, washed thrice with deionized water (100 mL/each), dried over magnesium sulfite, filtered, and concentrated under vacuum to a colorless oil. The oil can be placed on the Kugelrohr at 0.1 Torr and 40° C. for 30 minutes to afford a yellow oil (13.4 grams, 57.3%) that can be identified by NMR and gas chromatography analysis to be indicated >94% 6,7,7,7-tetrafluoro-4,6-bis-trifluoromethyl-heptanesulfonyl chloride.

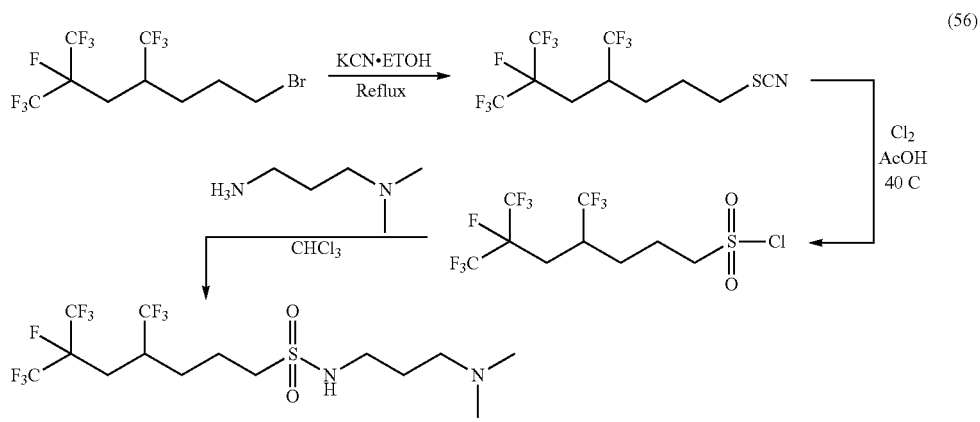

(56)

Referring to scheme (56) above, a solution of the $R_F$-intermediate

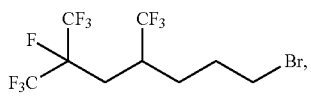

Dimethylaminopropyl amine (11.6 mL) can be dissolved in chloroform (75 mL) and cooled to 0° C. The 6,7,7,7-tetrafluoro-4,6-bis-trifluoromethyl-heptanesulfonyl chloride (13.4 grams) can be dissolved in chloroform (75 mL) and added drop-wise to the cooled solution to form a mixture. Once the addition is complete, the mixture can be allowed to warm to room temperature, and can be washed with saturated bicarbonate solution (150 mL), deionized water (150 mL), and brine (150 mL). The organic layer can be separated, dried over magnesium sulfate, filtered, and concentrated under vacuum to afford an orange oil (14.94 grams, 96.0%). The orange oil can be found to be 6,7,7,7-tetrafluoro-4,6-bis-trifluoromethyl-heptane-1-sulfonic acid (3-dimethylamino-propyl)-amide by NMR analysis.

(57)

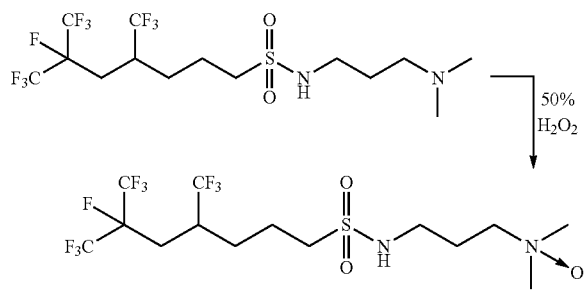

Referring to scheme (57) above, the 6,7,7,7-tetrafluoro-4,6-bis-trifluoromethyl-heptane-1-sulfonic acid (3-dimethylamino-propyl)-amide (7.5 grams) can be dissolved in 25 mL ethanol, deionized water (30 mL) and 50% (wt/wt) hydrogen peroxide (3.7 mL). The homogeneous mixture can be allowed to stir at ambient temperature overnight. Decolorizing carbon (5 g) and ethanol (15 mL) can be added to the mixture and the mixture heated to 50° C. for 2.5 hrs while monitoring for peroxide. The reaction mixture can then be cooled to room temperature and filtered through celite. The filter cake can be washed with 90% (wt/wt) ethanol, 10% (wt/wt) water (50 mL), the filtrate concentrated under vacuum and the resulting oil identified as

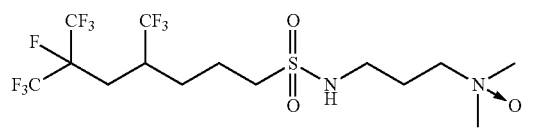

by NMR.

(58)

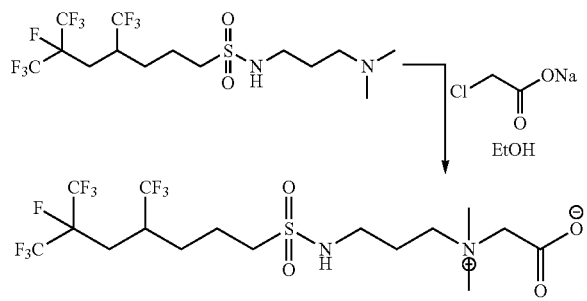

Referring to scheme (58) above, the 6,7,7,7-tetrafluoro-4,6-bis-trifluoromethyl-heptane-1-sulfonic acid (3-dimethylamino-propyl)-amide (7.5 grams) can be dissolved in ethanol (40 mL), and sodium chloroacetate (1.85 grams) to form a mixture. The mixture can be refluxed overnight. The heterogeneous mixture can be cooled to room temperature and filtered, the filtrate concentrated under vacuum to afford an orange oil. The orange oil can be dried on the Kugelrohr at 0.1 Torr and 50° C. for one hour to afford an amber solid (7.85 grams, 93.1%). The amber solid can identified as

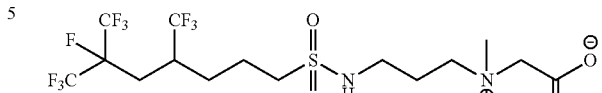

by NMR analysis.

According to another embodiment, a mercaptan $R_F$-intermediate may also be produced by reacting a iodine $R_F$-intermediate with thiourea to make the isothiuronium salt and treating the isothiuronium salt with sodium hydroxide to give the mercaptan $R_F$-intermediate plus sodium iodide, as described in U.S. Pat. No. 3,544,663 herein incorporated by reference.

In an exemplary aspect of the disclosure, the mercaptan $R_F$-intermediate may be attached to a $Q_s$ portion such as group 2-acrylamido-2-methyl-1 propane sulfonic acid available from Lubrizol as AMPS 2403, as generally described in U.S. Pat. No. 4,000,188 herein incorporated by reference.

Aminoxides of the $R_F$-surfactants can be produced according to processes that include those generally described in U.S. Pat. No. 4,983,769, herein incorporated by reference. Accordingly, sulfoamidoamines can be combined with ethanol and water and 70% (wt/wt) hydrogen peroxide and heated to at least 35° C. for 24 hours. Activated carbon can then be added and the mixture and refluxed for about 2 hours. The reaction mixture can be filtered and the filtrate evaporated to dryness to provide the aminoxide of the $R_F$-surfactant.

In accordance with another embodiment of the disclosure, processes are provided that can be used to alter the surface tension of a part of a system having at least two parts. The system can include liquid/solid systems, liquid/gas systems, gas/solid systems, and/or liquid/liquid systems. In an exemplary embodiment, the liquid/liquid systems can have one part that includes water and another part that includes a liquid that is relatively hydrophobic when compared to water. According to another example, the liquid/liquid system can contain one part that is relatively hydrophobic when compared to water and/or relatively hydrophobic when compared to another part of the system. $R_F$-surfactants can be used to alter the surface tension of a part of the system, for example, by adding the $R_F$-surfactant to the system.

$R_F$-surfactants may be used as relatively pure solutions or as mixtures with other components. For example, and by way of example only, the $R_F$-surfactants can be added to a system and the surface tension of the system determined by the Wilhelmy plate method and/or using the Kruss Tensiometer method.

The surface tensions of solutions of

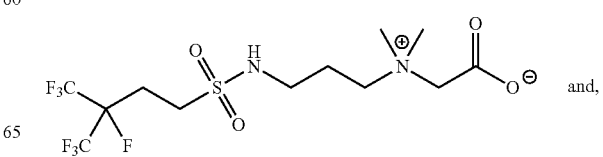

and,

-continued

Figure 9:
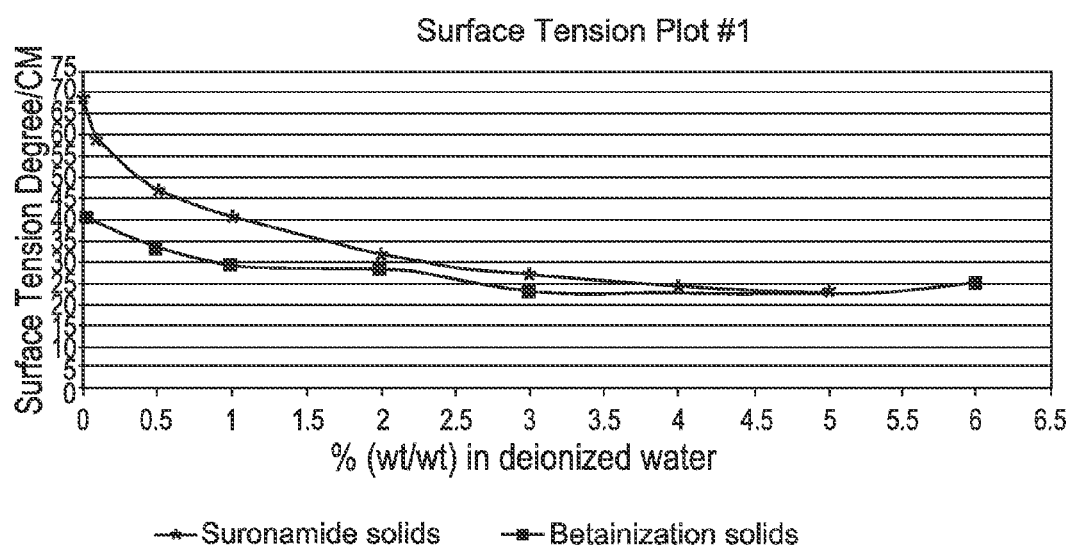
FIG. 9 illustrates Surface Tension Plot No. 1.

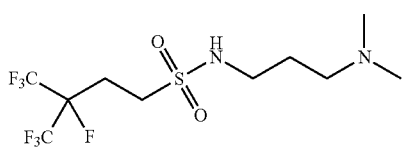

can be determined, according to the concentrations in Plot #1 as shown in FIG. 9

As another example, the surface tensions of

Figure 10:
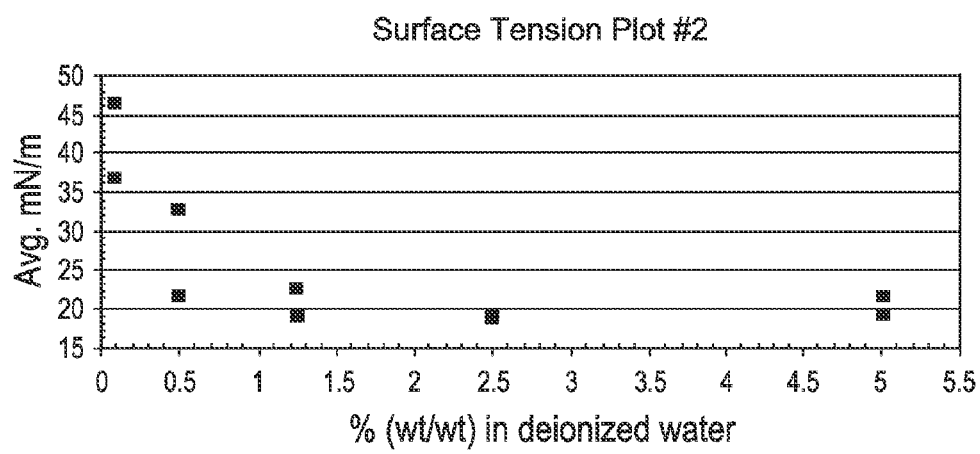
FIG. 10 illustrates Surface Tension Plot No. 2.

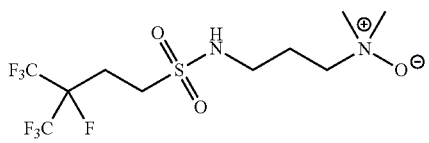

at pH 7 and pH 5 various concentrations can be determined and the data as indicated in Plot #2 as shown in FIG. 10.

As another example, the surface tensions of

Figure 11:
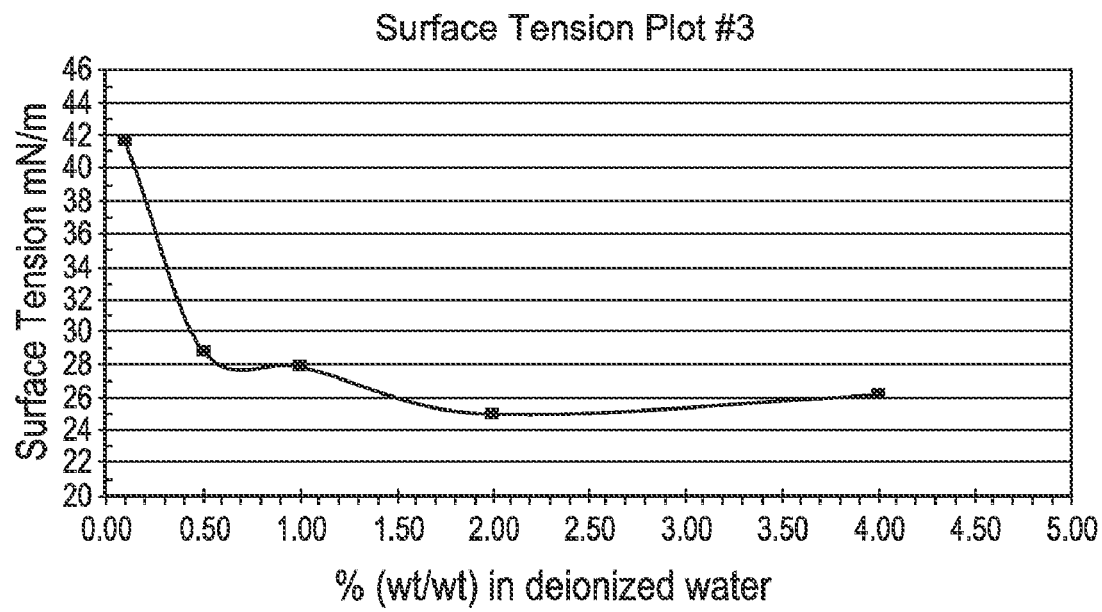
FIG. 11 illustrates Surface Tension Plot No. 3.

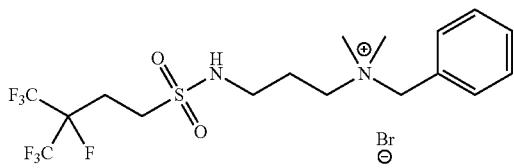

at various concentrations can be determined and the data as indicated in the Plot #3 as shown in FIG. 11.

As another example, the surface tensions of

Figure 12:
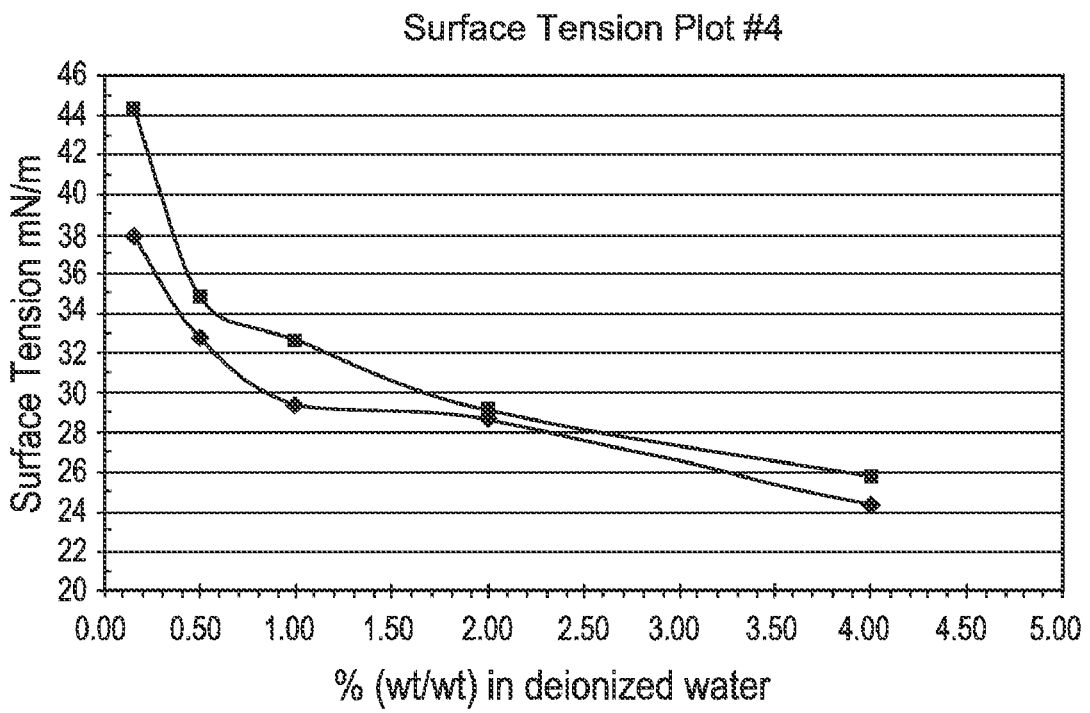
FIG. 12 illustrates Surface Tension Plot No. 4.

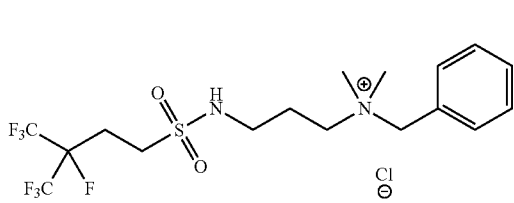

at pH 6.8 and pH 4.0 can be determined and the data as indicated in Plot #4 as shown in FIG. 12.

As another example, the surface tensions of

Figure 13:
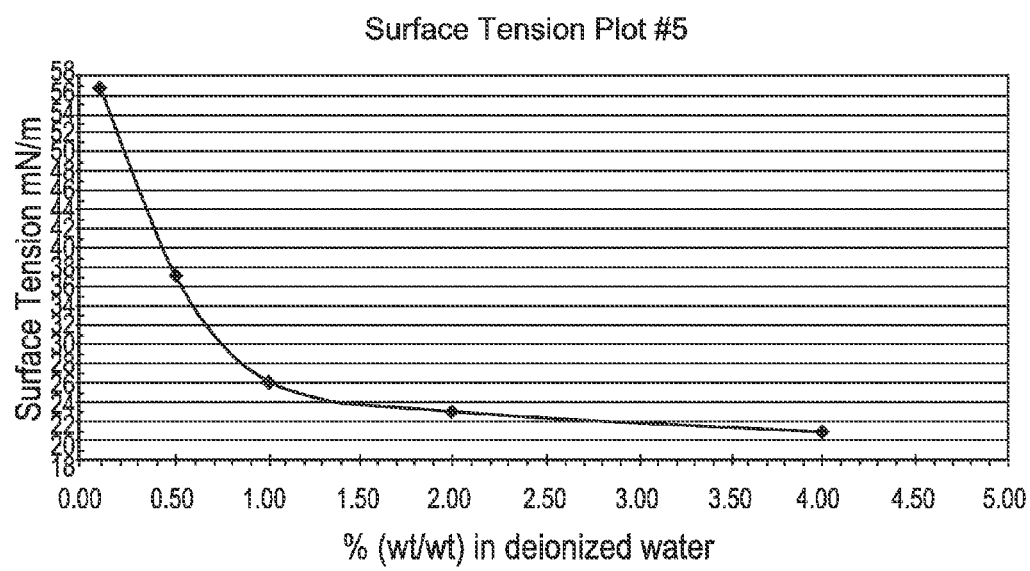
FIG. 13 illustrates Surface Tension Plot No. 5.

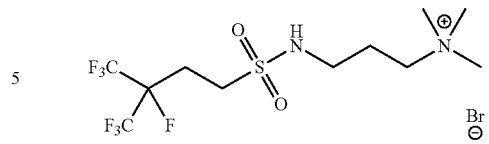

at various concentrations can be determined and the data as indicated in Plot #5 as shown in FIG. 13.

As another example, the surface tensions of

Figure 14:
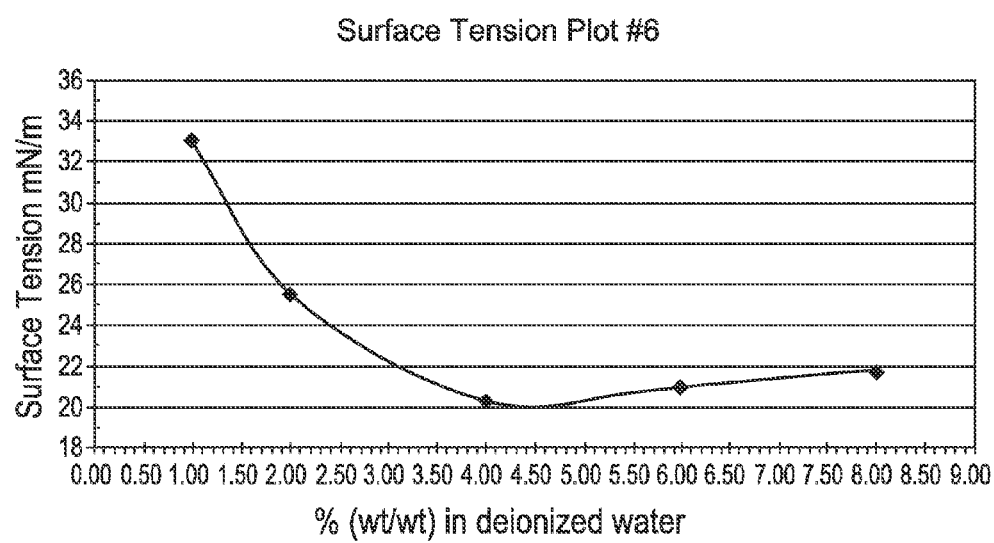
FIG. 14 illustrates Surface Tension Plot No. 6.

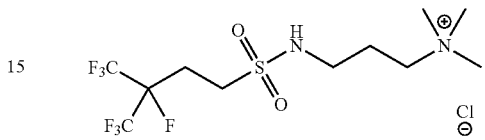

at various concentrations can be determined and the data as indicated in Plot #6 as shown in FIG. 14.

As another example, the surface tensions of

Figure 15:
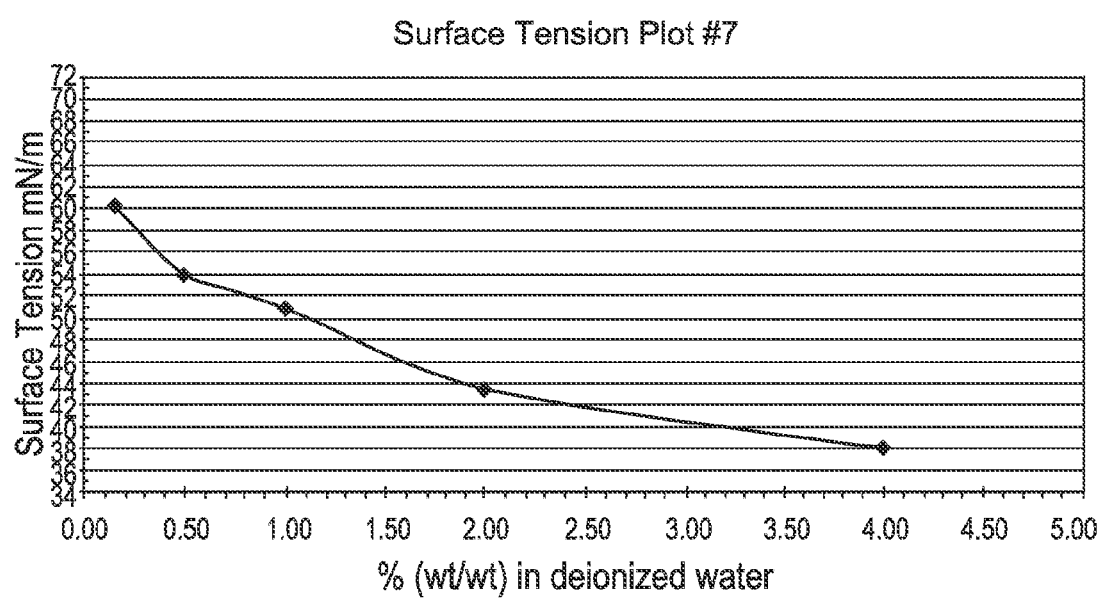
FIG. 15 illustrates Surface Tension Plot No. 7.

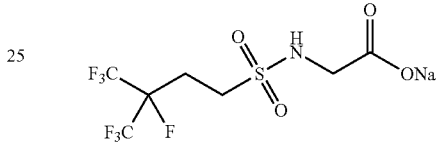

at various concentrations can be determined and the data as indicated in Plot #7 as shown in FIG. 15.

As another example, the surface tensions of

Figure 16:
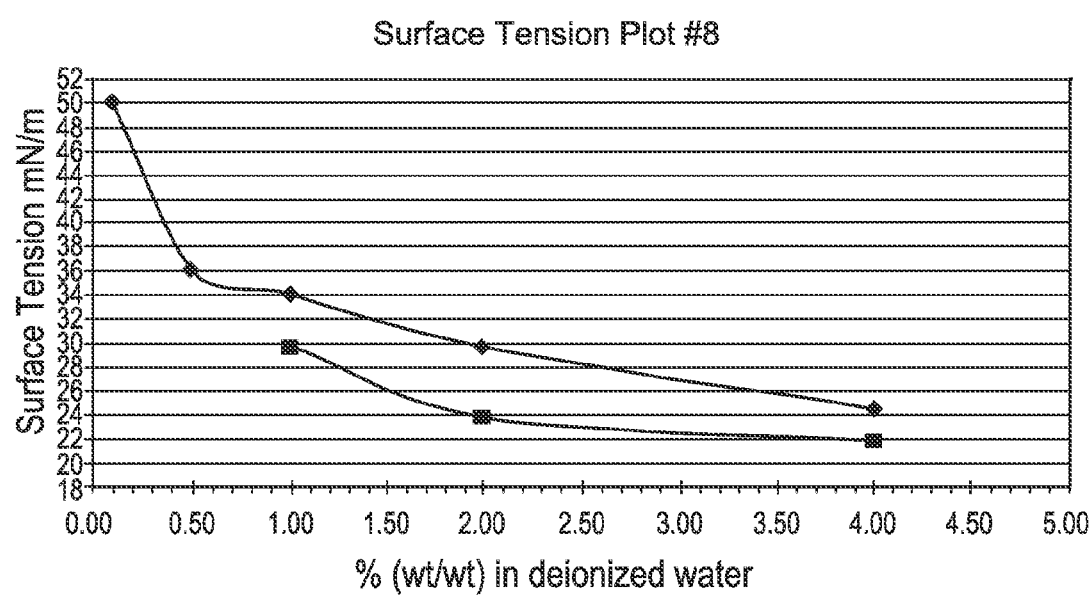
FIG. 16 illustrates Surface Tension Plot No. 8.

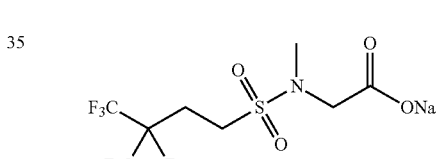

at pH 6.2-6.8 and pH 5.0 can be determined and the data as indicated in Plot #8 as shown in FIG. 16.

Surface tensions and corresponding concentrations of $R_F$-surfactants are denoted in Table 6 below.

TABLE 6

$R_F$-Surfactant Surface Tensions

| $R_F$-surfactant | Surface Tension (mN/m) | Concentration % (wt/wt) |
|---|---|---|
| (structure) | 20.9 | 2.5 |
| (structure) | 18.7 | 2.5 |

TABLE 6-continued

R$_F$-Surfactant Surface Tensions

| R$_F$-surfactant | Surface Tension (mN/m) | Concentration % (wt/wt) |
|---|---|---|
| [structure: (CF$_3$)$_2$CF-CH$_2$CH$_2$-SO$_2$-NH-(CH$_2$)$_3$-N$^+$(CH$_3$)$_2$-CH$_2$-C$_6$H$_5$ Br$^-$] | 25 | 2 |
| [structure: (CF$_3$)$_2$CF-CH$_2$CH$_2$-SO$_2$-NH-(CH$_2$)$_3$-N$^+$(CH$_3$)$_2$-CH$_2$-C$_6$H$_5$ Cl$^-$] | 24.3 | 4 |
| [structure: (CF$_3$)$_2$CF-CH$_2$CH$_2$-SO$_2$-NH-(CH$_2$)$_3$-N$^+$(CH$_3$)$_3$ Br$^-$] | 20.9 | 4 |
| [structure: (CF$_3$)$_2$CF-CH$_2$CH$_2$-SO$_2$-NH-CH$_2$-C(O)-ONa] | 37.8 | 4 |
| [structure: (CF$_3$)$_2$CF-CH$_2$CH$_2$-SO$_2$-N(CH$_3$)-(CH$_2$)$_3$-N$^+$(CH$_3$)$_3$ Cl$^-$] | 20.2 | 4 |
| [structure: (CF$_3$)$_2$CF-CH$_2$CH$_2$-SO$_2$-N(CH$_3$)-CH$_2$-C(O)-ONa] | 21.7 | 4 |
| [branched bis-(CF$_3$)$_2$CF-CH$_2$CH$_2$- group-CH$_2$CH$_2$-SO$_2$-NH-(CH$_2$)$_3$-N(CH$_3$)$_2$→O] | 19.8 | 0.05 |
| [structure: (CF$_3$)$_2$CF-CH$_2$CH$_2$-SO$_2$-NH-(CH$_2$)$_3$-N(CH$_3$)$_2$→O] | 21.3 | 2 |
| [structure: (CF$_3$)$_2$CF-(CH$_2$)$_5$-SO$_2$-NH-(CH$_2$)$_3$-N(CH$_3$)$_2$→O] | 21.8 | 0.25 |
| [structure: (CF$_3$)$_2$CF-O-(CH$_2$)$_3$-SO$_2$-NH-(CH$_2$)$_3$-N(CH$_3$)$_2$→O] | 31.7 | 2 |

TABLE 6-continued
R_F-Surfactant Surface Tensions
| R_F-surfactant | Surface Tension (mN/m) | Concentration % (wt/wt) |
|---|---|---|
| 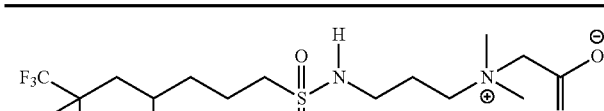 | 20.4 | 0.13 |
| 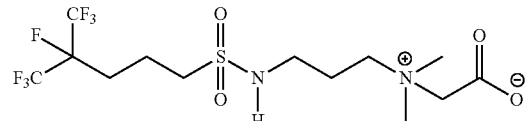 | 21.5 | 2 |
| 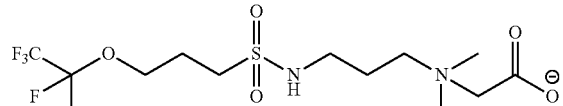 | 34.4 | 1 |
| 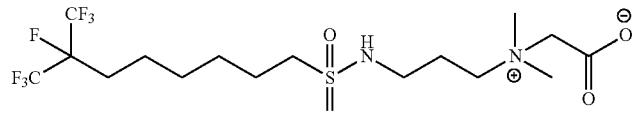 | 21.6 | 0.25 |
| 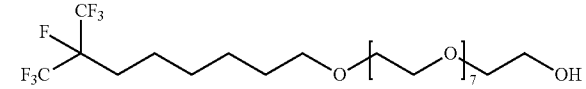 | 25.7 | 1 |
| 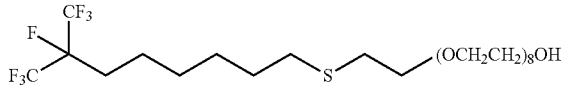 | 23.8 | 1 |
| 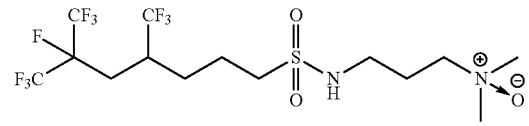 | 19.7<br>20.3 | 0.5<br>0.25 |
| 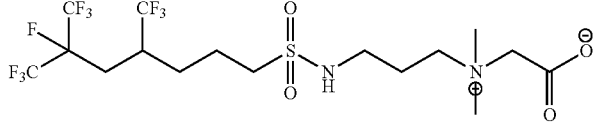 | 20.2<br>20.6 | 0.5<br>0.25 |
| 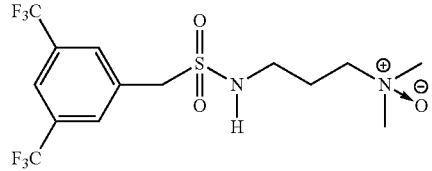 | 34.4 | 0.25 |

TABLE 6-continued $R_F$-Surfactant Surface Tensions

| $R_F$-surfactant | Surface Tension (mN/m) | Concentration % (wt/wt) |
|---|---|---|
| [structure: bis-CF3-benzyl sulfonamide propyl dimethylamine N-oxide] + [structure: bis(bis-CF3-benzylsulfonyl) imide propyl dimethylamine N-oxide] | 25.9 −50.50 | 2 |

$R_F$-surfactants described above may be incorporated into detergents, emulsifiers, paints, adhesives, inks, wetting agents, foamers, and/or defoamers, for example.

$R_F$-surfactants can be incorporated into AFFF formulations and these formulations can be used as fire-fighting foams, to prevent, and/or extinguish combustion. An exemplary use of AFFFs that include an $R_F$-surfactant includes the addition of the AFFF to high pressure misting systems, the misting systems being used to prevent and/or extinguish combustion. AFFF formulations can be provided to a substrate, for example. The substrate can include liquid and/or solid compositions. The AFFF formulations can also be dispersed into an atmosphere including gaseous atmospheres, such air to prevent and/or extinguish combustion.

The formulations can include other components such as water soluble solvents. These solvents may facilitate the solubilization of the $R_F$-surfactants and other surfactants. These solvents can also act as foam stabilizers and/or freeze protection agents. Exemplary solvents include ethylene glycol, diethylene glycol, glycerol, ethyl Cellusolve®, butyl Carbitol®, Dowanol DPM®, Dowanol TPM®, Dowanol PTB®, propylene glycol, and/or hexylene glycol. Additional components to the formulation, such as polymeric stabilizers and thickeners, can be incorporated into the formulation to enhance the foam stability property of a foam produced from aeration of the aqueous solution of the formulation. Exemplary polymeric stabilizers and thickeners include partially hydrolyzed protein, starches, polyvinyl resins such as polyvinyl alcohol, polyacrylamides, carboxyvinyl polymers, and/or poly(oxyethylene)glycol. Polysaccharide resins, such as xanthan gum, can be included in the formulation as a foam stabilizer in formulations for use in preventing or extinguishing polar solvent combustion, such as alcohol, ketone, and/or ether combustion, for example. The formulation can also include a buffer to regulate the pH of the formulation, for example, tris(2-hydroxyethyl)amine or sodium acetate, and a corrosion inhibitor such as toluoltriazole or sodium nitrite may be included. Water soluble electrolytes such as magnesium sulphate may be included and can improve film-spreading characteristics of the formulation.

For example and by way of example only, the following formulations can be prepared using $R_F$-surfactants. Formulations recited in the following tables can be prepared and applied to the indicated substrates.

TABLE 7

Exemplary AFFF formulation #1

| Material | Concentration % (wt/wt) |
|---|---|
| [structure of fluorinated sulfonamide propyl dimethylamine N-oxide] | 2.5 |
| Alpha Foamer (ROSO$_2$O(C$_2$H$_4$O)$_n$Na; R = C$_8$C$_{10}$ mixture n = 1.5 (51% active); Stepan Co. 22 W. Frontage Road Northfield, Illinois.) | 1.5 |
| SDS (ROSO$_2$ONa R = C$_{10}$ (40% Active); Colonial Chemical Co. E. Pittsburg, TN) | 2.8 |
| APG 325N (RO)glucose)n R= C$_9$, n = 1.5 (50% active); Cognis North America 5051 Estecreek Drive Cincinnati, OH) | 4.0 |
| Hexylene Glycol | 9.0 |

TABLE 7-continued

Exemplary AFFF formulation #1

| Material | Concentration % (wt/wt) |
|---|---|
| $MgSO_4$ | 2.0 |
| Water | 78.20 |

A 3% (wt/wt) premixed solution of formulation #1 in water from Table 7 above can be used to film on the substrate heptane.

TABLE 8

Exemplary AFFF formulation #2

| Material | Concentration % (wt/wt) |
|---|---|
| 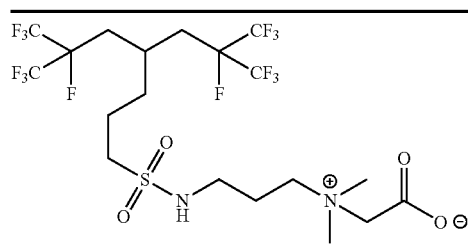 | 4 |
| Colateric CA-40® (Colonial Chemical Co. E. Pittsburg TN) | 13 |
| SDS ($ROSO_2ONa$ R = $C_{10}$ (40% Active); Colonial Chemical Co. E. Pittsburg, TN) | 10.5 |
| Propylene Glycol | 12 |
| Diethylene glycol monobutylether | 14 |
| $MgSO_4$ | 2 |
| Water | Remainder |

A 3% (wt/wt) premixed solution of formulation #2 in water from Table 8 above can be used to film on the substrate heptane.

TABLE 9

Exemplary AFFF Mix Formulation

| Material | Concentration % (wt/wt) |
|---|---|
| Alpha Foamer ($ROSO_2O(C_2H_4O)_nNa$; R = $C_8C_{10}$ mixture n = 1.5 (51% active); Stepan Co. 22 W. Frontage Road Northfield, Illinois.) | 8.32 |

TABLE 9-continued

Exemplary AFFF Mix Formulation

| Material | Concentration % (wt/wt) |
|---|---|
| APG325N ((RO)glucose)n R = $C_9$, n = 1.5 (50% active); Cognis North America 5051 Estecreek Drive Cincinnati, Oil)) | 1.47 |
| $MgSO_4$ | 1.05 |
| Propylene Glycol | 5.97 |
| Hexylene Glycol | 8.42 |
| Water | 74.7 |

A third formulation including 3% (wt/wt) of the mix formulation of Table 9 above and 0.15% (wt/wt) of

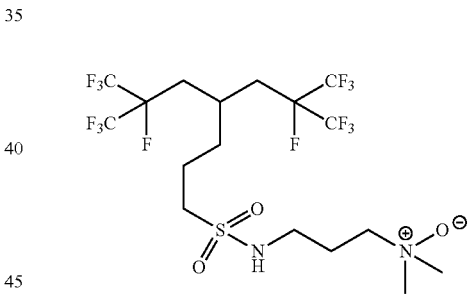

can form film on the substrates heptane and cyclohexane.

A fourth formulation including 3% (wt/wt) of the mix formulation of Table 9 above and 0.15% (wt/wt) of

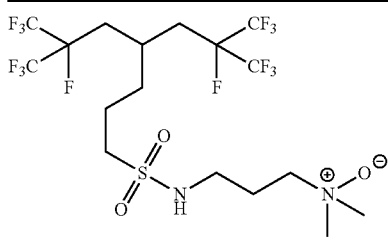

can form film on the substrates heptane and cyclohexane.

TABLE 10

Exempary AFFF formulations 5 and 6

| Material | Formulation 5 Concentration % (wt/wt) | Formulation 6 Concentration % (wt/wt) |
|---|---|---|
| (structure shown) | 2.5 | 0.0 |

TABLE 10-continued

Exempary AFFF formulations 5 and 6

| Material | Formulation 5 Concentration % (wt/wt) | Formulation 6 Concentration % (wt/wt) |
|---|---|---|
| 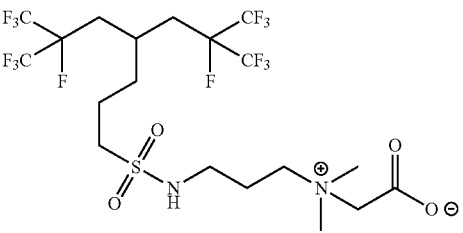 | 0.0 | 6.5 |
| Ethanol | 3.8 | 7.9 |
| Colalux LO (RN(CH$_3$)$_2$(O) (30% active); Colonial Chemical Co, E. Pittsburg, TN | 4.2 | 6.6 |
| Colalux CA-40® (Colonial Chemical Co. E, Pittsburg TN) | 4.0 | 0.0 |
| APG 325N ((RO)glucose)n R = C$_9$, n = 1.5 (50% active); Cognis North America 5051 Estecreek Drive Cincinnati, OH) | 0.0 | 2.0 |
| Hexylene Glycol | 9.0 | 9.0 |
| MgSO$_4$ | 2.0 | 2.0 |
| Water | Remainder | Remainder |

Formulations 5 and 6 of Table 10 above can be used at 3% (wt/wt) concentrations to generate foam and film over the substrate heptane. The $R_F$-surfactants can also be useful in formulations that include other surfactants such as alkyl sulfate, alkylethersulfates, alphaolefinsulfonates, alkyl sulfobetaines, alkyl polyglycerides, alkylamidopropylbetaines, alkylimidazotinedicarboxylates, 2-alkylthiopropionamido-2 methyl-propanesulfonoic acid sodium salt, alkyliminodipropinates, alkylsulfonates, ethoxylated alkylphenols, dialkylsulfosuccinates, and/or alkyltrimethyl ammonium chloride.

A variation of AFFF, ARAFFF, an acronym for Alcohol Resistant Aqueous Film Forming Foam(s), can be used to extinguish hydrocarbon fires in much the same manner that AFFF foams are used and may also be used to extinguish fires involving water soluble solvents such as acetone and isopropanol which conventional AFFF foams will not extinguish.

ARAFFF formulations can contain the same ingredients as conventional AFFF formulations plus a polysaccharide such as xanthan gum and, in some formulations, a polymeric foam stabilizer. Polymeric foam stabilizers are offered by DuPont® and Dynax®, Inc. An exemplary DuPont product, Forafac® 1268, is a water soluble acrylic polymer. An exemplary Dynax product, DX5011®, is an ethyleneimine polymer. Xanthan gum is offered by several suppliers, including Kelco CP (Kelzan) and Rhodia North America (Rhodopol).

Polysaccharide alone can be sufficient to make ARAFFF formulations alcohol resistant, but the amount required produces a foam concentrate that can be quite viscous. The use of a polymeric foam stabilizer can permit a reduction in the amount of polysaccharide required to give useful alcohol resistance.

Because of the possibility of microbial attack on polysaccharide solutions, ARAFFF concentrates can contain an effective amount of a biocide such as Kathon CG ICP, manufactured by Rohm & Haas. Many other biocides such as Acticide, Nipacide and Dowicil can also be effective.

Some ARAFFF formulations can be designed to be pro-portioned at different percentages depending on whether the substrate to be extinguished is a hydrocarbon or an alcohol type substrate, for example. Alcohol type can include any fuel having a hydroxyl group.

Exemplary ARAFFF formulations (3% (wt/wt)×3% (wt/wt)) utilizing the $R_F$ surfactants are described in Tables 11-14 as follows. In all eases described in Tables 11-14, water is balance of formulation,

TABLE 11

Exemplary ARAFFF

| Raw Material | Kg/kg |
|---|---|
| 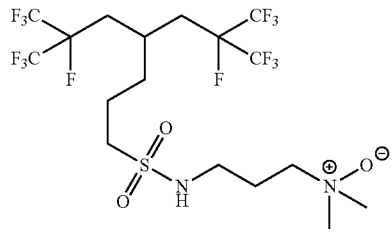 | 0.025 |
| Dynax 5011® | 0.025 |
| Sodium Decyl Sulfate 40% Active | 0.061 |
| APG 325N 50% Active | 0.035 |
| Coco Sulfobetaine 30% Active | 0.010 |
| Butyl Diglycol | 0.060 |
| Propylene Glycot | 0.030 |
| Xanthan Gum | 0.012 |
| Kathon CG/ICP)® | 0.002 |

TABLE 12

Exemplary ARAFFF

| Raw Material | Kg/kg |
|---|---|
| 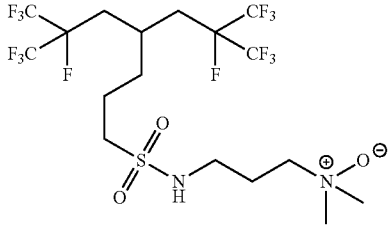 | 0.065 |
| Dynax 5011 | 0.025 |
| Sodium Decyl Sulfate 40% Active | 0.061 |
| APO 325N 50% Active | 0.035 |
| Coco Sulfobetaine 30% Active | 0.010 |
| Butyl Diglycol | 0.060 |
| Propylene Glycol | 0.030 |
| Xanthan Gum | 0.012 |
| Katlion CG/ICP | 0.002 |

TABLE 13

Exemplary ARAFFF

| Raw Material | Kg/kg |
|---|---|
| 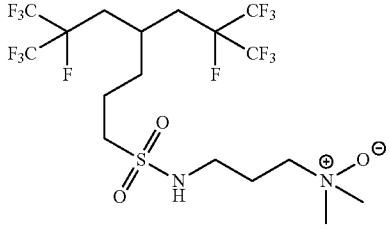 | 0.025 |
| Dynax 5011 | 0.000 |
| Sodium Decyl Sulfate 40% Active | 0.061 |
| APG 325N 50% Active | 0.035 |
| Coco Sulfobetaine 30% Active | 0.010 |
| Butyl Diglycol | 0.060 |
| Propylene Glycoi | 0.030 |
| Xanthan Gum | 0.014 |
| Kathon CG/ICP | 0.002 |

TABLE 14

Exemplary ARAFFF

| Raw Material | Kg/kg |
|---|---|
| 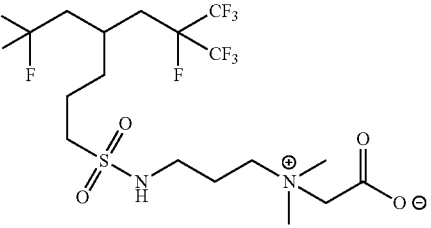 | 0.065 |
| Dynax 5011 | 0.000 |
| Sodium Decd Sulfate 40% Active | 0.061 |
| APG 325N 50% Active | 0.035 |
| Coco Sulfobetaine 30% Active | 0.010 |
| Butyl Diglycol | 0.060 |

TABLE 14-continued

Exemplary ARAFFF

| Raw Material | Kg/kg |
|---|---|
| Propylene Glycol | 0.030 |
| Xanthan Gum | 0.014 |
| Katlion CG/ICP | 0.002 |

Foam stabilizers, such as $R_F$-stabilizers that include $R_F$ groups described above, for example, can be prepared, $R_F$-stabilizers can include $R_F$-$Q_{FS}$ compositions. $Q_{FS}$ can include portions that have a greater hydrophilic character than $R_F$.

Exemplary $R_F$-Foam Stabilizers include, but are not limited to those in Table 15 below.

TABLE 15

Exemplary $R_F$-Foam Stabilizers

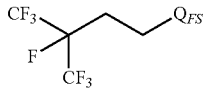
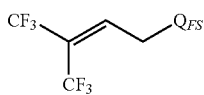
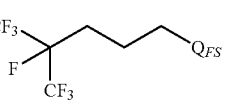
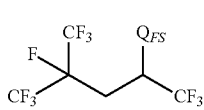
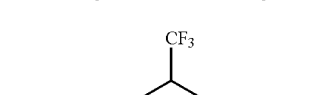
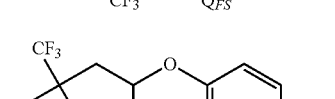
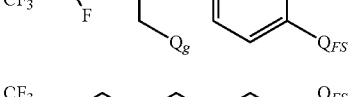
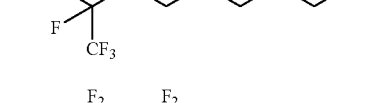
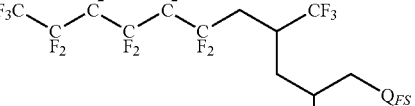
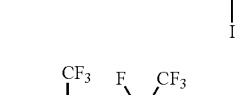

TABLE 15-continued
Exemplary $R_F$-Foam Stabilizers
For example and by way of example only,
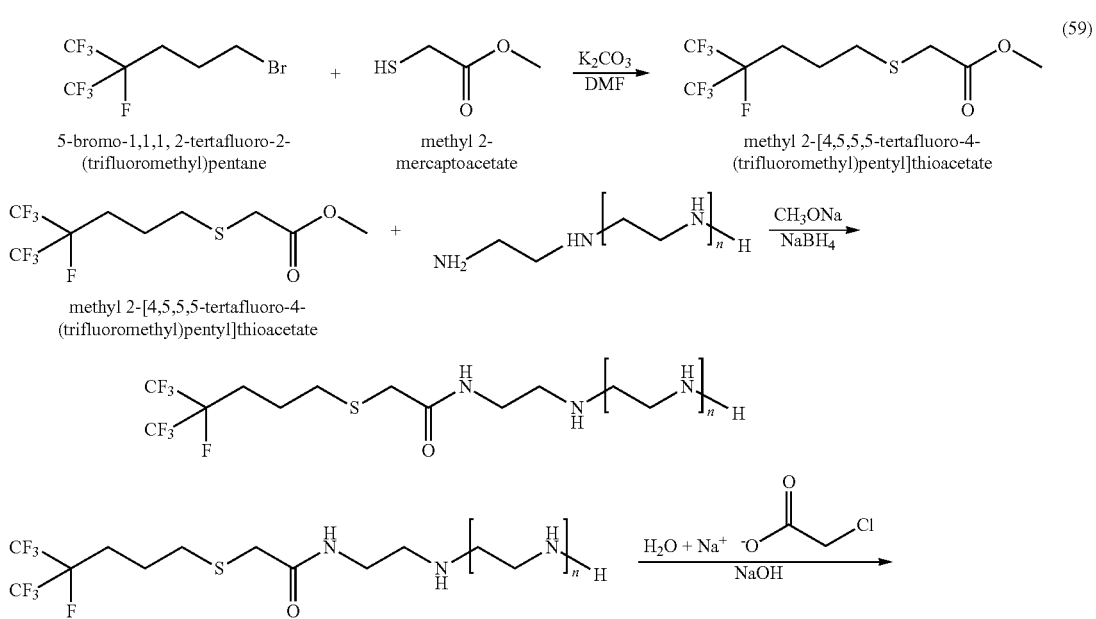
can be a $Q_{FS}$ portion. $R_F$-stabilizers can be prepared according to scheme (59) below.

-continued

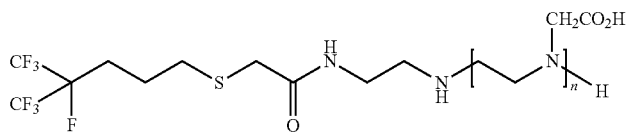

Referring to scheme (59) above, potassium carbonate (2.37 grams), methioglycolate (1.82 grams) and dimethylformamide (DMF) (20 mL) can be added and the mixture heated to 50° C. for 3 hours. The mixture can be allowed to stir overnight at room temperature to form a yellow slurry which can be added to water (50 mL) and ethyl acetate (50 mL), the organic layers combined, dried over $Na_2SO_4$, filtered, and stripped of solvent.

In a nitrogen atmosphere, thioester (4.0 grams) and polyethylenimine (PEI, mw=1200) (5.3 grams) can be placed in isopropanol (5 mL) and stirred until dissolved to form a mixture. Sodium methoxide (0.15 grams) and sodium borohydride (0.04 grams) can be added to the mixture and the mixture heated to 115° C. for 15 hours, then stirred at room temperature for 2 days. Removal of remaining isopropanal can be difficult. A solution of sodium chloroacetate (10.52 grams) in water (25 mL) can be added drop-wise to the mixture and the temperature kept below 55° C. and the mixture then heated to 70° C. for two hours. NaOH (1.23 grams of a 50% (wt/wt) solution of NaOH and water) can be added to raise the pH of the mixture to at least 7.5 from the starting pH of approximately 6. The mixture can then be allowed to continue stirring at 70° C. for 2 additional hours, the heat then removed, and the resulting

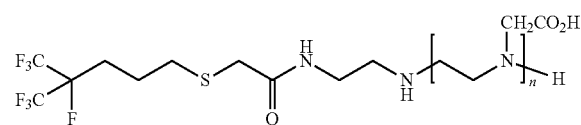

(44 grams, 82% yield.) characterized ($^1$HNMR analysis). The

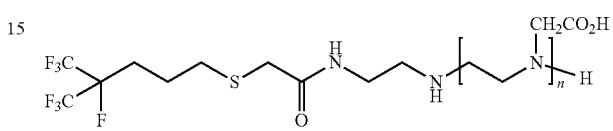

produced can be compared with other foam stabilizers in accordance with Tables 16-19 below.

TABLE 16

Foam Stabilizer test on warm acetone (52° C.-53° C.) 150 mm dish - 100 grams of blended foam solution

| ARAFFF | 6% (wt/wt) Conc. |
| --- | --- |
| 1.4% (wt/wt) Xanthan Gum Solution | 35.70 |
| F 1157N | 1.50 |
| Dynax 5011 | 1.25 |
| ALPHA FOAMER | 0.75 |
| SDS | 1.40 |
| APG 325N | 2.00 |
| HG | 1.50 |
| MgSO$_4$ | 1.00 |
| WATER | 54.90 |

First hole in film 11 min. 08 sec. after formation and 50% collapse of foam 11 min. 35 sec. after formation.

TABLE 17

Foam Stabilizer test on warm acetone (52°-53° C.) 150 mm dish-100 grams of blended foam solution

| ARAFFF | 6% (wt/wt) Conc. |
| --- | --- |
| 1.4%(wt/wt) Xanthan Gum Solution | 35.70 |
| F 1157N | 1.50 |
| 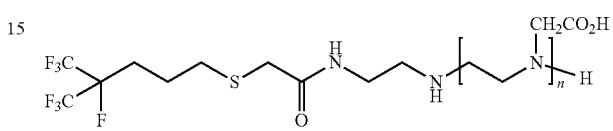 | 1.50 |
| ALPHA FOAMER | 0.75 |
| SDS | 1.40 |
| APG 325N | 2.00 |
| HG | 1.50 |
| MgSO$_4$ | 1.00 |
| WATER | 54.65 |

First hole 8 min. 4 sec. after formation and 50% collapse 10 min. 30 sec. after formation.

TABLE 18

Foam Stabilizer test on warm acetone (52° C.-53° C.)
150 mm dish-100 grams of blended foam solution

| ARAFFF | 6% (wt/wt) Conc. |
|---|---|
| 1.4% (wt/wt) Xanthan Gum Solution | 35.70 |
| F 1157N | 1.50 |
| 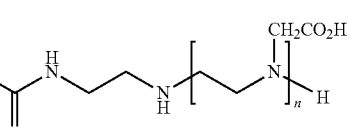 | 3.00 |
| ALPHA FOAMER | 0.75 |
| SDS | 1.40 |
| APG 325N | 2.00 |
| HG | 1.50 |
| MgSO$_4$ | 1.00 |
| WATER | 53.15 |

First hole 12 min. 20 sec. after formation and 50% collapse 12 min. 45 sec. after formation.

TABLE 19

Foam Stabilizer test on warm acetone (52° C.-53° C.) 150 mm - 100 grams of blended foam solution

| ARAFFF | 6% (wt/wt) Conc. |
|---|---|
| 1.4% (wt/wt) Xanthan Gum Solution | 35.70 |
| F 1157N | 1.50 |
| No stabilizer | 0.00 |
| ALPHA FOAMER | 0.75 |
| SDS | 1.40 |
| APG 325N | 2.00 |
| HG | 1.50 |
| MgSO$_4$ | 1.00 |
| WATER | 56.15 |

First hole 7 min. 40 sec. after formation.

$R_F$-metal complexes such as $R_F$-$Q_{MC}$ incorporating the $R_F$ portions are also provided. The $R_F$ portions can be incorporated as acid halides or carboxylic acids, for example, with the acid halide including, but not limited to, acid fluorides, for example. $R_F$-metal complexes can include $R_F$-intermediates and, as such, $Q_g$ can be interchangeable with $Q_{MC}$. $Q_{MC}$ can include the portion of a ligand of a metal complex that is coordinated with the complexed metal, for example. Exemplary $R_F$-metal complexes include, but are not limited to, those in Table 20 below.

TABLE 20

$R_F$-Metal Complexes

TABLE 20-continued $R_F$-Metal Complexes

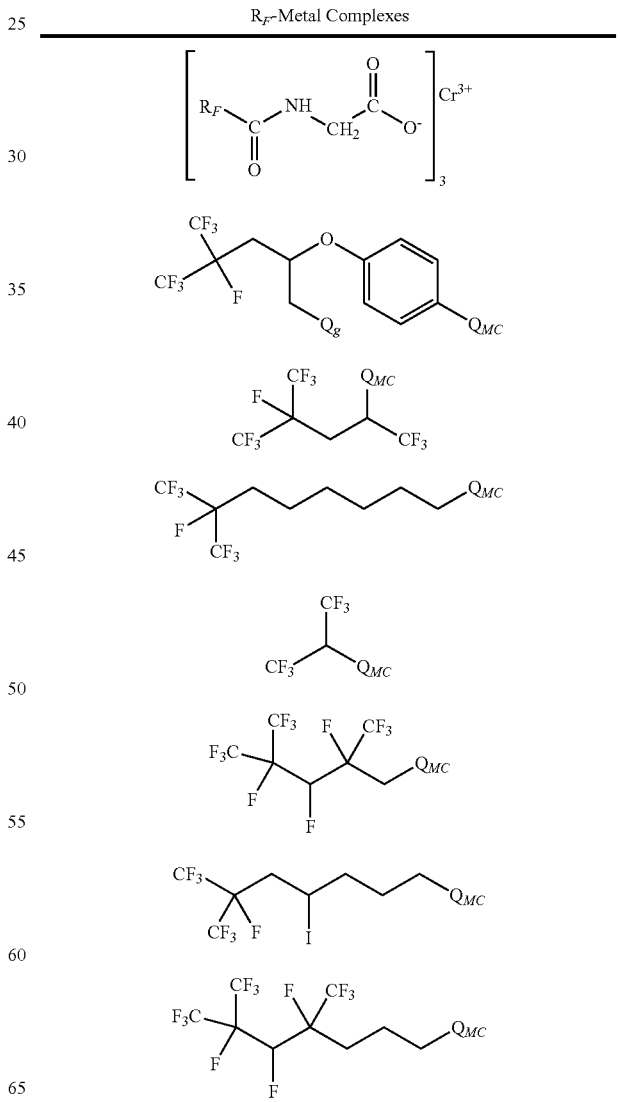

TABLE 20-continued

R_F-Metal Complexes

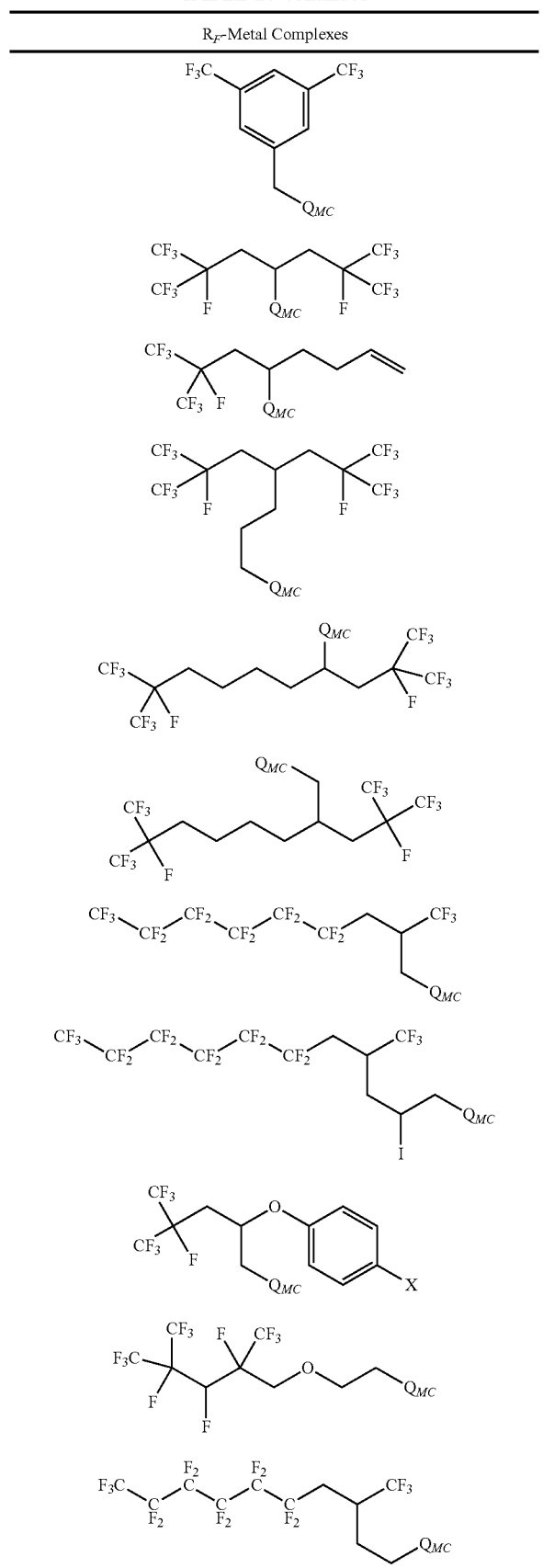
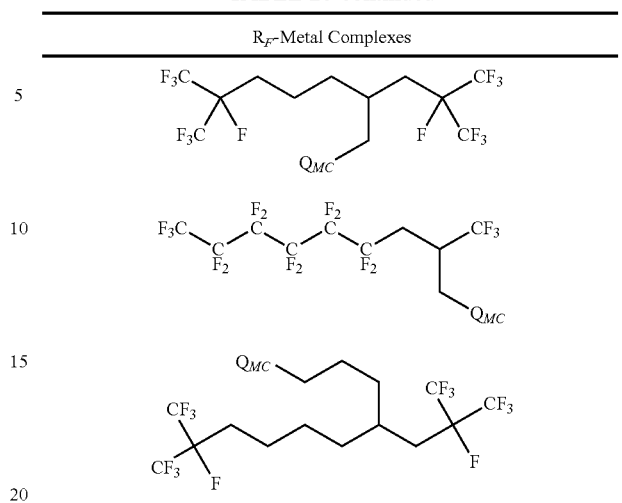

An exemplary method for preparing the $R_F$-metal complexes includes reacting the $R_F$-intermediate having halogen functionality, such as $Q_g$ is 1, disclosed above, with fuming sulfuric acid to produce an $R_F$-intermediate having acid fluoride functionality, for example. $R_F$-metal complexes can be prepared with reference to scheme (60) below.

(60)

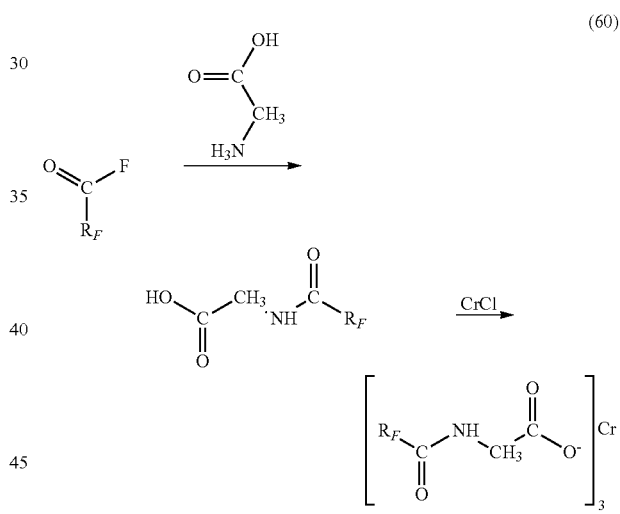

An acid fluoride $R_F$-intermediate can be reacted with an amino acid such as glycine to produce an amine ester. The amine ester may then be reacted with chromic chloride in an alcohol such as methanol or isopropanol to produce an exemplary $R_F$-metal complex such as a $R_F$ chrome complex. Exemplary acid $R_F$-intermediates for use in preparation of $R_F$-metal complexes can include ethylene carboxylic acid $R_F$-intermediates and/or mixtures of ethylene carboxylic acid $R_F$-intermediates and carboxylic acid $R_F$-intermediates. Exemplary preparations can be performed in accordance with U.S. Pat. Nos. 3,351,643, 3,574,518, 3,907,576, 6,525,127, and 6,294,107, herein incorporated by reference. $R_F$-metal complexes can include a ligand having a $R_F$ portion and a $Q_{MC}$ portion associated with the metal of the complex. In exemplary embodiments the $Q_{MC}$ portion can have a greater affinity for the metal of the complex than the $R_F$ portion. $R_F$-metal complexes can be used to treat substrates such as paper, leather, textiles, yarns, fabrics, glass, ceramic products, and/or metals. In some cases treating substrates with the complexes render the substrates less permeable to water and/or oil.

An embodiment of the present invention also provides for incorporation of the $R_F$ portions into phosphate esters which, in exemplary embodiments, can be used to treat substrates and/or be used as dispersing agents during the preparation of polymers. Exemplary $R_F$-phosphate esters include $R_F$-$Q_{PE}$, with the $Q_{PE}$ portion being the phosphate portion of the $R_F$-composition. $R_F$-phosphate esters, include, but are not limited to, those in Table 21 below.

TABLE 21

$R_F$-Phosphate Esters

[chemical structures]

TABLE 21-continued $R_F$-Phosphate Esters

[chemical structures]

Exemplary $R_F$-phosphate esters can be prepared with reference to schemes (61) and (62) below.

(61)

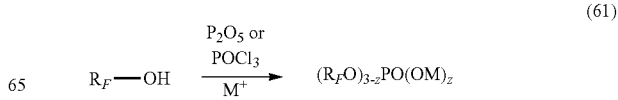

Referring to scheme (61) above, a $R_F$-intermediate having hydroxyl functionality ($Q_g$=OH) can be obtained by reacting iodine $R_F$-intermediates ($Q_g$=I) with a strong base such as KOH. The iodine $R_F$-intermediate can be reacted with $P_2O_5$ or $POCl_3$ in the presence of a metal (M) to yield an exemplary $R_F$-phosphate ester or $R_F$-pyrophosphate in accordance with U.S. Pat. Nos. 2,559,749 and 2,597,702, herein incorporated by reference, which generally describe the conversion of hydroxyl compounds to phosphate esters using $P_2O_5$ or $POCl_3$ to give partial esters. These reactions can also be carried out in the presence of pyridine as an HCl acceptor. Monoalkyl phosphates can also be prepared by treating phosphorus pentoxide $P_2O_5$ with excess moles of hydroxyl $R_F$-intermediate followed by hydrolysis of the resulting $R_F$-pyrophosphate. The product can then be isolated or precipitated as the ammonium salt by the addition of ammonia to the reaction mixture. Alternatively, a solution of salts of the mixed mono- and di-esters can be prepared by neutralizing a mixture of the acids with aqueous ammonia and amine or alkaline metal hydroxide.

$R_F$-dialkyl phosphates can also be prepared as well by a reaction of excess moles of $R_F$-intermediate with phosphorus pentoxide (not shown). Instead of hydrolysis, however the $R_F$-pyrophosphate intermediate can be heated at low pressure. Alternatively, $R_F$-phosphate esters can be prepared and separated by treating hydroxyl $R_F$-intermediate with phosphorus pentoxide, neutralizing the resulting mixed acid phosphate with aqueous ammonia, and amine such as tetraalkyl ammonium base or alkali metal hydroxide to give a solution that can include amine or metal salts of the esters (not shown). Salts of esters can be dissolved in toluene and purged with ammonia to precipitate a mixture of the salts of the corresponding esters. The toluene and unreacted hydroxyl $R_F$-intermediate and by-products, such as the corresponding $R_F$-trialkyl phosphate, can be removed by filtration producing compositions having the general formula $R_F$AOPORp, as described in U.S. Pat. No. 4,145,382, herein incorporated by reference. As used in this general formula, the $R_F$ is the $R_F$ portion, A is a methylene group or other similar spacer group from the phosphate ester and can be present in amounts as high as 3 and as little as none, and Rp is a corresponding salt to the phosphate including hydrogen alkali metal ammonium or substituted ammonium such as ethanol amine.

$R_F$-phosphates can be used as dispersing agents in the preparation of polymers or they can be diluted and used to treat substrate materials in aqueous bathes, for example, by ordinary means such as padding, dipping, impregnating, spraying, etc. These compositions can be incorporated into or used to treat such materials as textile fabric, textile yarns, leather, paper, plastic, sheeting, wood, ceramic clays, as well as, manufactured articles prepared therefrom such as articles of apparel, wallpaper, paper bags, cardboard boxes, porous earthenware, etc. U.S. Pat. No. 3,112,241 describes methods for treating materials using phosphate esters and is herein incorporated by reference.

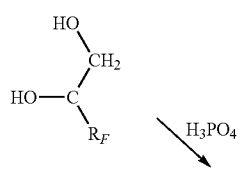

(62)

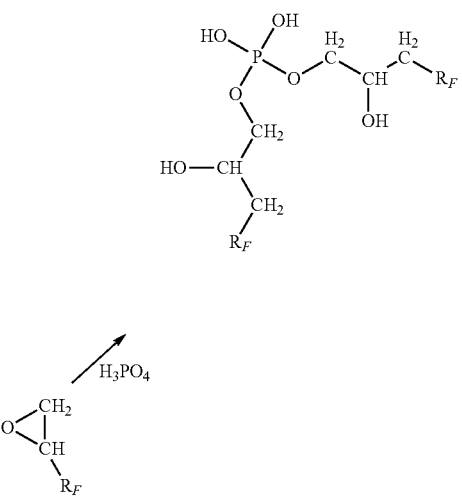

Referring again to scheme (62) above, $R_F$-epoxide intermediate and/or $R_F$-diol intermediate can be prepared as generally described in U.S. Pat. No. 3,919,361 which is herein incorporated by reference. $R_F$-epoxide and diol intermediates can be reacted with phosphoric acid to obtain an $R_F$-phosphoric acid ester. $R_F$-phosphoric acid ester can be dissolved in a solution and applied to a substrate such as paper to increase resistance to environmental materials such as oil and water. $R_F$-phosphoric acid ester can also exist as a salt such as alkyl amines including ethanol amines as described in U.S. Pat. No. 4,145,382, herein incorporated by reference. $R_F$-phosphoric acid ester can be used to treat substrates such as wood pulp products, including paper products such as packaging products including food packaging products.

An embodiment includes the $R_F$ portions incorporated into glycols, such as $R_F$-glycols, including $R_F$-$Q_h$, with $Q_h$ representing the ether portion of the glycol after conjugation or, as hydroxyl functionality before conjugation as the ether. Exemplary $R_F$-glycols include, but are not limited to, those in Table 22 below.

TABLE 22

Exemplary $R_F$-Glycols

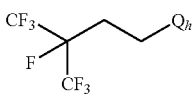

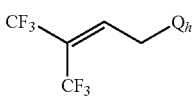

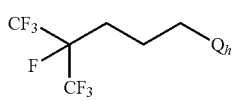

TABLE 22-continued
Exemplary R$_F$-Glycols
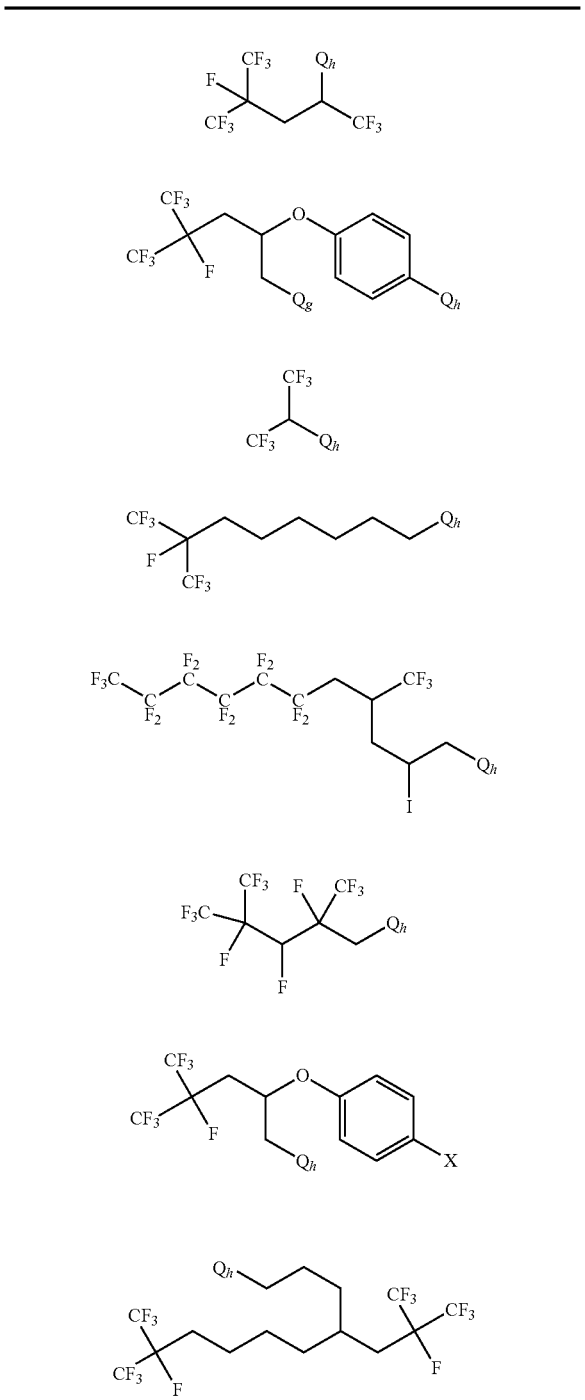
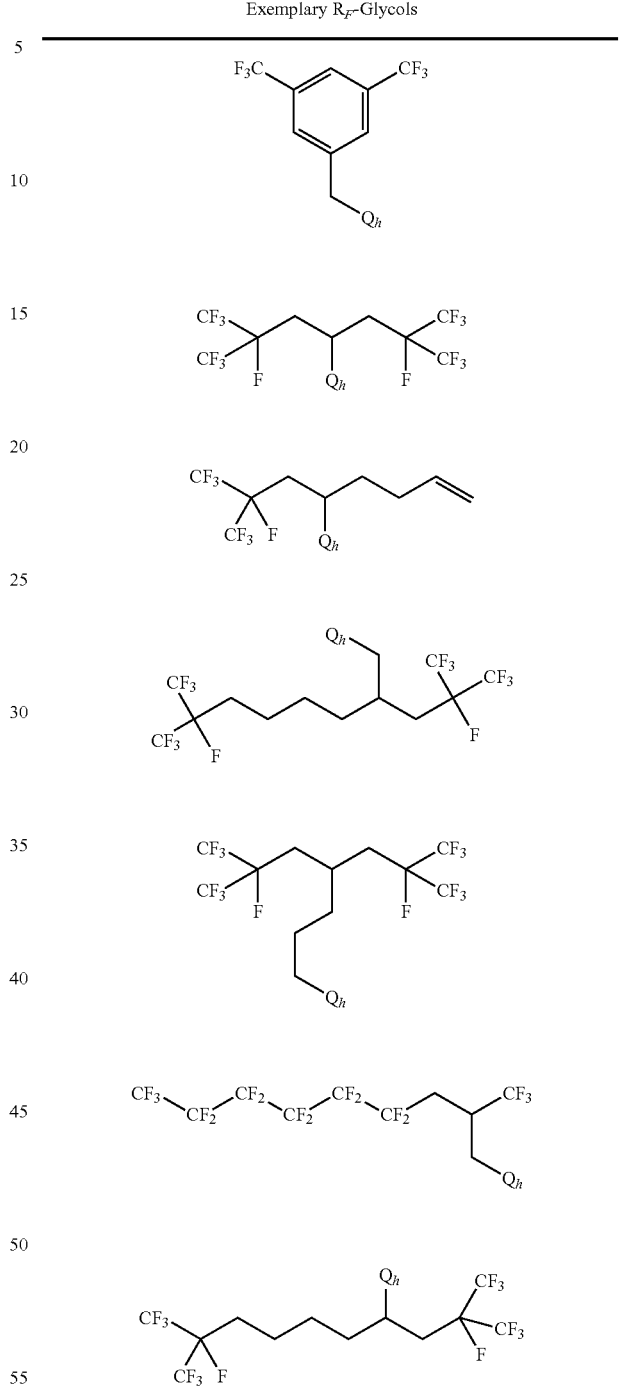
R$_F$-glycols can be incorporated into polymers such as urethanes including polyurethane elastomers, films and coatings, for example. R$_F$-glycols can also be converted to phosphoric acids or phosphate esters of those glycols as well. Referring to scheme (63) below, R$_F$ portions can be incorporated into glycols.

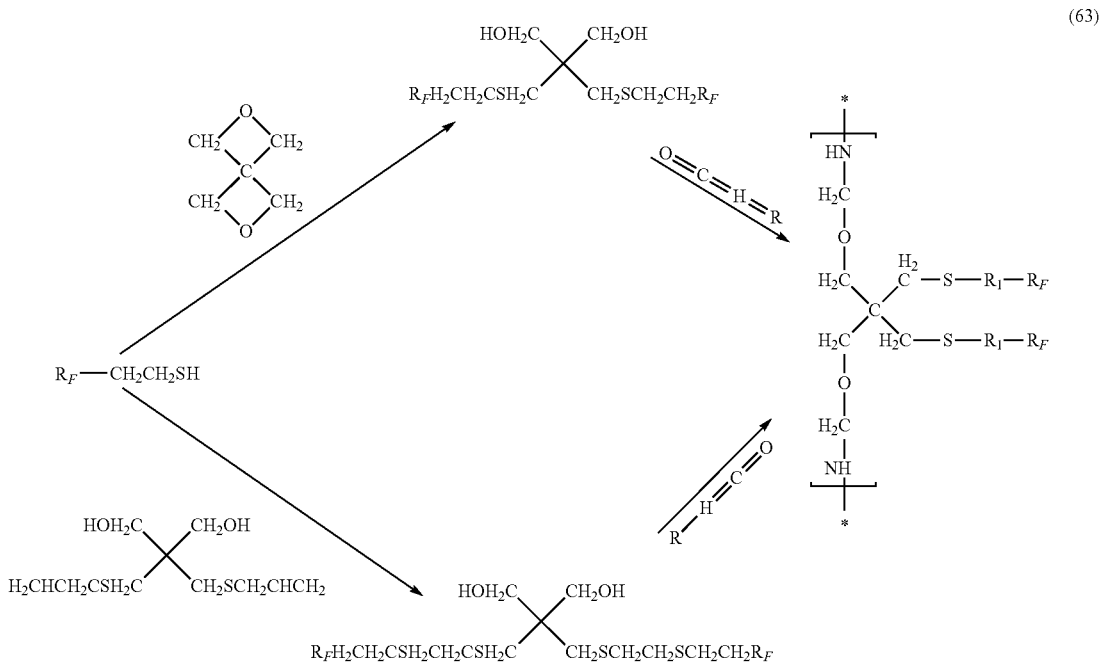

(63)

Methods for preparing glycols are described in U.S. Pat. No. 4,898,981, U.S. Pat. No. 4,491,261, U.S. Pat. No. 5,091,550, and U.S. Pat. No. 5,132,445, all of which are herein incorporated by reference. For example, and by way of example only, a $R_F$-intermediate ($Q_g$=SH) can be reacted with a sulfide diol or 2,6 diox-aspiro(3,3) heptane to produce exemplary $R_F$-glycols (Qh=H$_2$CH$_2$CSH$_2$CH$_2$ ... ). The $R_F$-glycol can then be used directly or indirectly to prepare a $R_F$ condensation product such as polyesters, polyureas, polycarbonates, and polyurethanes. This glycol functionality can also be incorporated into block polymers using $R_F$-glycols. U.S. Pat. No. 5,491,261 discloses several other glycols that can benefit from the $R_F$ portion of the present invention and is herein incorporated by reference.

$R_F$-glycols may also be converted to phosphoric acid functionality or phosphate esters (not shown). U.S. Pat. Nos. 5,091,550, 5,132,445, 4,898,981, and 5,491,261 all disclose methods of preparing dials and converting diols to phosphate esters and are herein incorporated by reference. In an exemplary implementation, the diols can be converted to phosphoric acid or phosphate esters by reacting the diols in the presence of phosphoric acid. These compositions can be incorporated into compounds which can act as oil and grease proofing for paper, as well as, soil release agents for textile fibers.

According to another embodiment of the present invention oligomers, polymers, copolymers, acrylics, and/or resins, for example, can be prepared that include an $R_F$-monomer unit, such as $R_F$-$Q_{MU}$. The monomer unit portion, $Q_{MU}$, can be a single unit within a complex of units and the monomer unit need not repeat within the complex. In an exemplary embodiment, the monomer unit can be a single unit within the complex or it may be one of many identical units linked together, such as a homopolymer, for example. The complex can also include block polymers and/or polyurethane resins. The $R_F$ of the unit can include a pendant group of the monomer unit. The monomer unit may be associated with a complex, perhaps even bonded to the complex, for example, and $Q_{MU}$ can include the portion of the monomer unit that is associated with the complex. The complex may be coated onto a substrate or it may be chemically bonded to the substrate. For example, a preparation of $R_F$-intermediates can be provided to the substrate and groups such as hydroxyl groups common to substrates like cotton, may provide sites that allow the $R_F$-intermediate to chemically bond to the substrate when forming part of, or being associated with a complex. In an exemplary embodiment, $Q_{MU}$ can represent the acrylate functionality of an acrylic and $R_F$ can be a pendant group from the acrylics chain and/or backbone. Exemplary RF-monomer units include but are not limited to those in Table 23 below.

TABLE 23

Exemplary $R_F$-Monomer Units

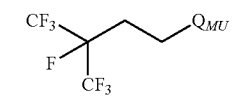

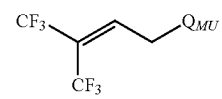

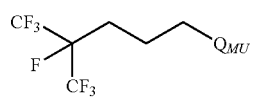

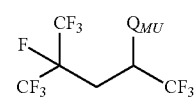

TABLE 23-continued

Exemplary $R_F$-Monomer Units

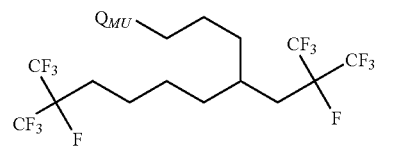
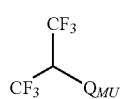
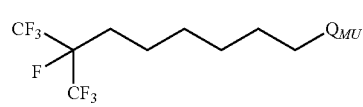
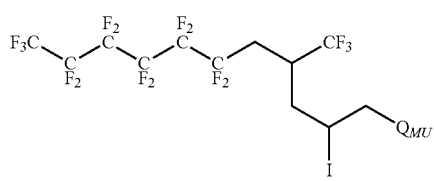
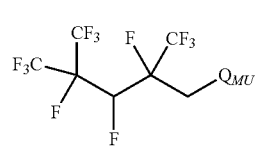
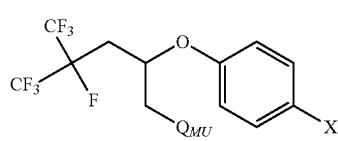
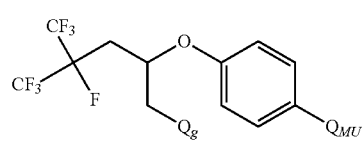
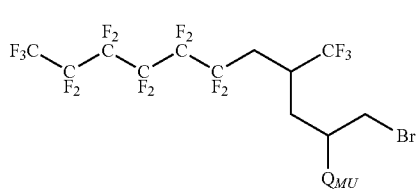
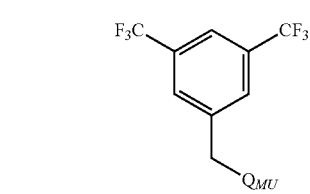

TABLE 23-continued

Exemplary $R_F$-Monomer Units

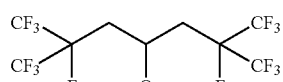
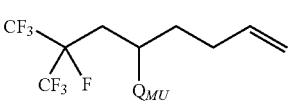
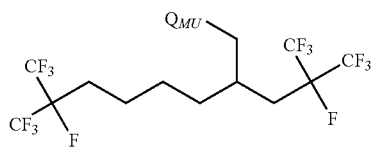
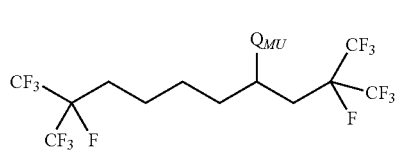
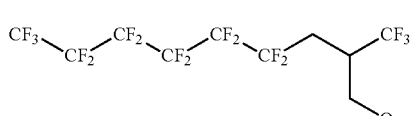
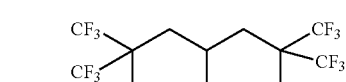
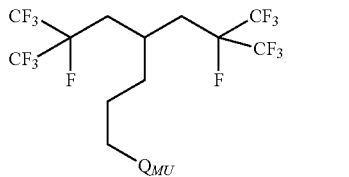
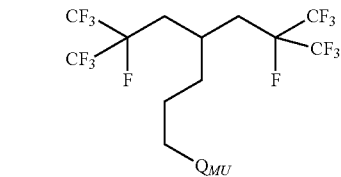

In exemplary embodiments oligomers containing a $R_F$-monomer unit can be prepared from $R_F$-monomers. $R_F$-monomers can include $R_F$-intermediates above, but may contain functionality that allows for their conjugation with another monomer, but not necessarily the same $R_F$-monomer. Exemplary $R_F$-monomers include, but are not limited to those in Table 24 below.

TABLE 24

Exemplary $R_F$-Monomers

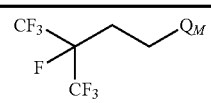
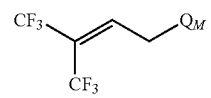
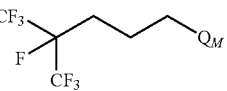

TABLE 24-continued
Exemplary $R_F$-Monomers
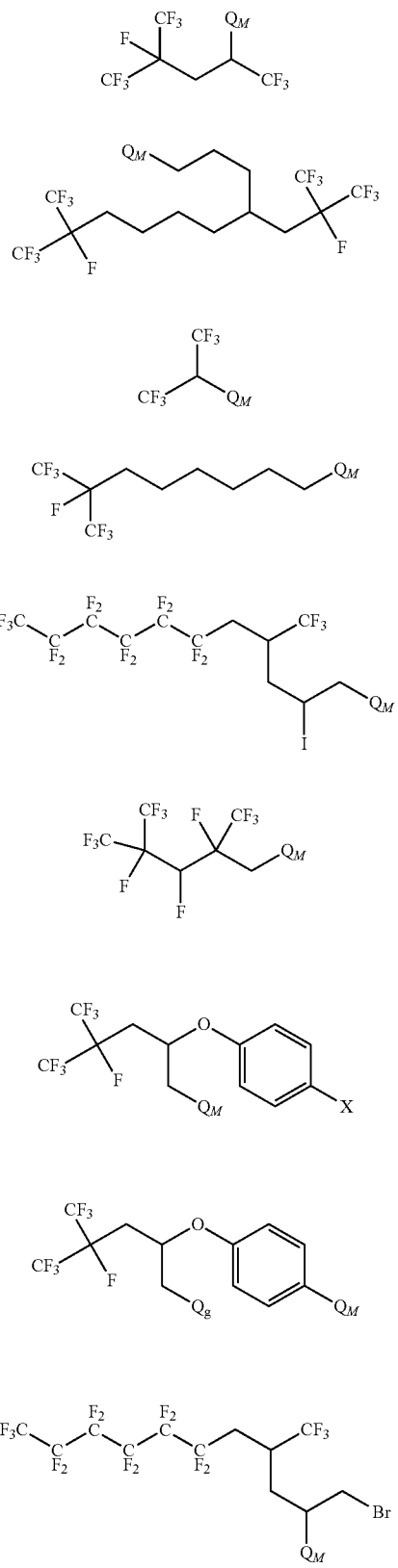
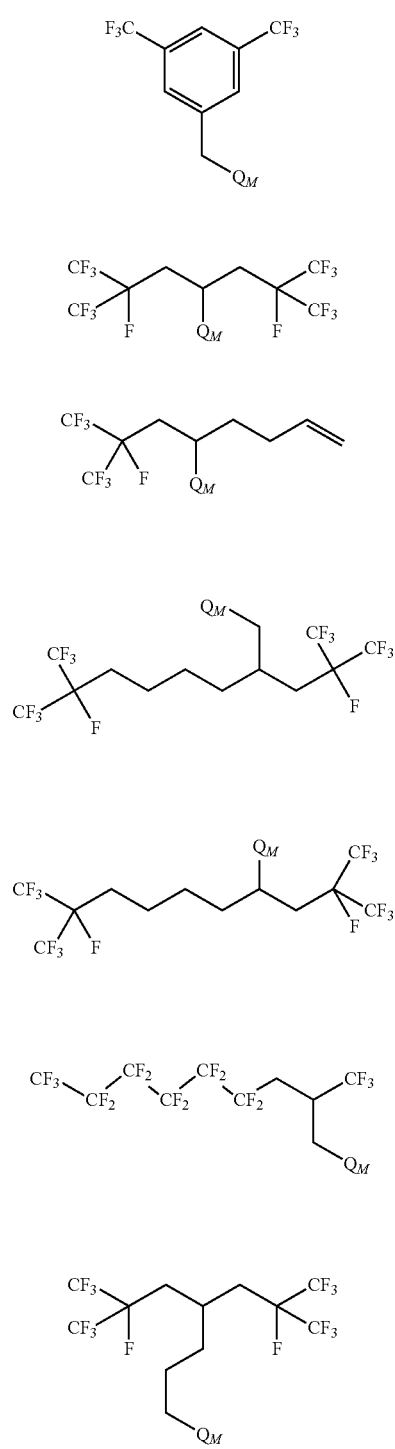
Referring to scheme (64) below, multiple reactions sequences are shown for the preparation of $R_F$-monomers having the $R_F$ group.

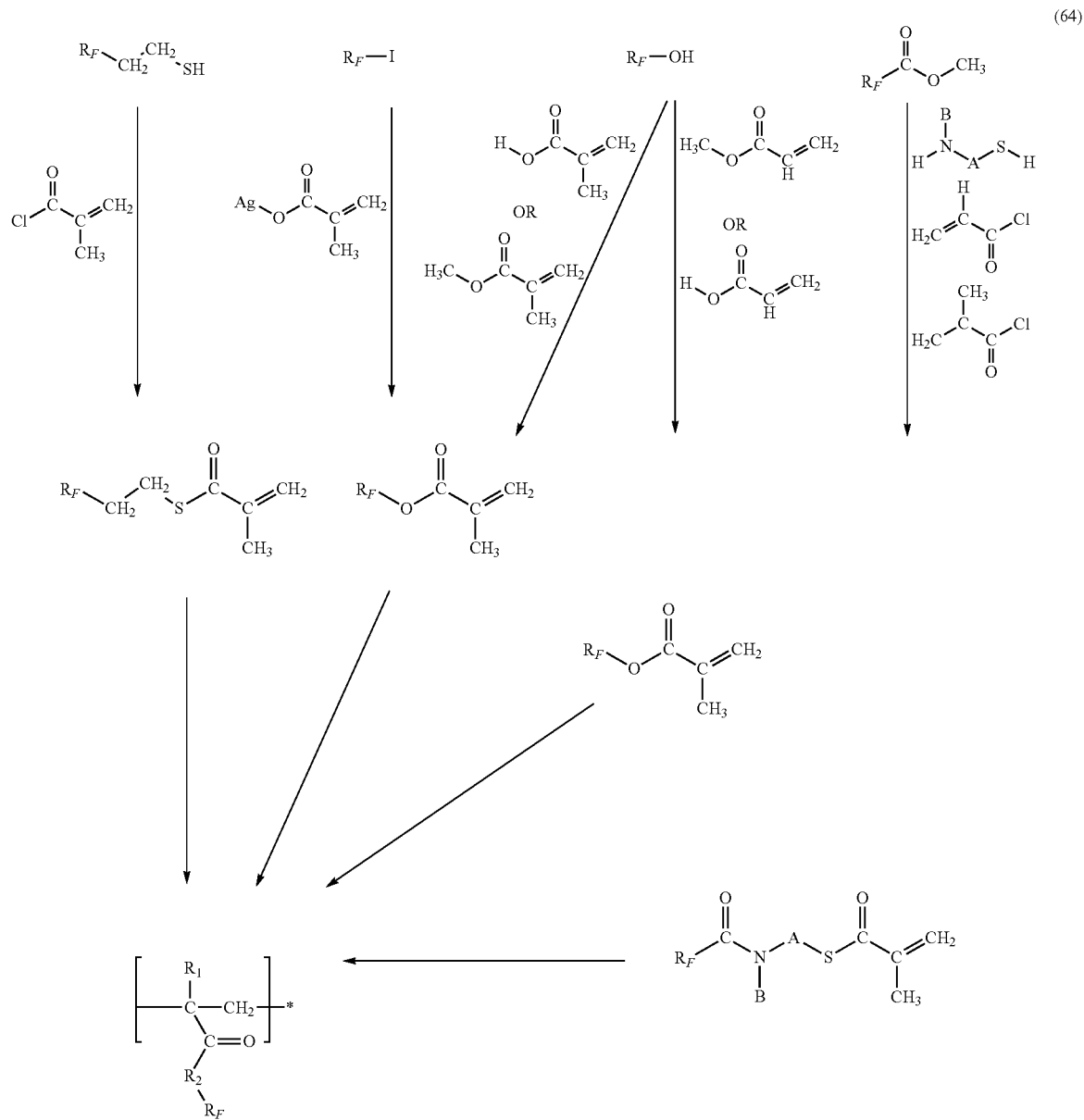

(64)

U.S. Pat. Nos. 3,491,169, 3,282,905, 3,497,575, 3,544,663, 6,566,470, 4,147,851, 4,366,299 and 5,439,998 all relate to the use and preparation of acrylic emulsion polymers that can benefit from the $R_F$ groups and, are herein incorporated by reference. Thiol $R_F$-intermediates, iodine $R_F$-intermediates, hydroxyl $R_F$-intermediates, and/or acetate $R_F$-intermediates can be converted to $R_F$-monomers according to scheme (63) above, and these $R_F$-monomers can be used to prepare a composition containing an $R_F$-monomer unit.

For example, and by way of example only, the $R_F$ portion can be incorporated into a $R_F$-monomer as described in U.S. Pat. No. 6,566,470 represented as $R_F$—W—X—C(=O)—C($R_1$)=$CH_2$, with the $R_F$ portion as described above. W can be an alkylene with 1 to 15 carbons, hydroxyalkylene with 3 to 15 carbons, —($C_nH_{2n}$)($OC_mH_{2m}$)$_q$—, —$SO_2NR_2$—($C_nH_{2n}$)—, or —$CONR_2$—($C_nH_{2n}$)—, with n is 1 to 12, m is 2 to 4, q is 1 to 10, and $R_1$ is an alkyl group with 1 to 4 carbon atoms, for example, X can be O, S and/or N($R_2$), where $R_2$ is as $R_1$.

For example, the $R_F$-monomer 4,5,5,5-tetrafluoro-4-(trifluormethyl)pentyl acrylate can be prepared from the $R_F$-intermediate 4,5,5,5-tetrafluoro-4-(trifluoromethyl)pent-1-ene in two steps shown below as reaction schemes (65) and (66) respectively.

(65)

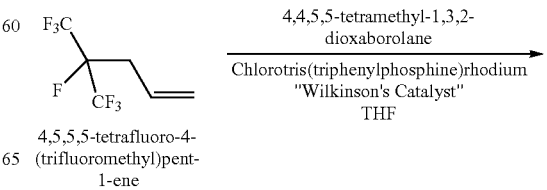

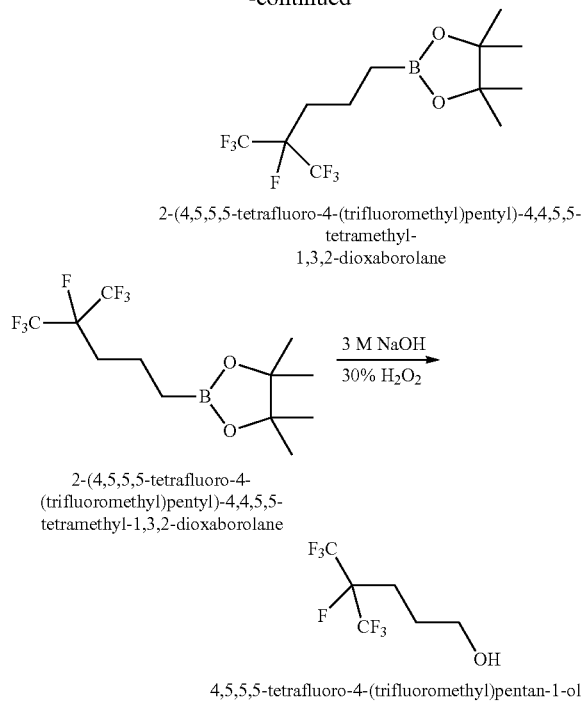

2-(4,5,5,5-tetrafluoro-4-(trifluoromethyl)pentyl)-4,4,5,5-tetramethyl-1,3,2-dioxaborolane 2-(4,5,5,5-tetrafluoro-4-(trifluoromethyl)pentyl)-4,4,5,5-tetramethyl-1,3,2-dioxaborolane 4,5,5,5-tetrafluoro-4-(trifluoromethyl)pentan-1-ol Referring to scheme (65) above, a 1M solution of 4,4,5,5-tetramethyl-1,3,2-dioxaborolane in tetrahydrofuran (66.1 grams, 0.075 moles), chlorotris(triphenylphosphine)rhodium (0.37 grams), and tetrahydrofuran (158.8 grams) can be placed in a 500 mL three-neck round bottom flask to form a mixture. 4,5,5,5-tetrafluoro-4-(trifluoromethyl)pent-1-ene (18.243, 0.087 moles) can be added to the mixture at room temperature over a 15 minute period, allowed to mix for 72 hours, and monitored by gas chromatography until which time the 4,5,5,5-tetrafluoro-4-(trifluoromethyl)pent-1-ene is substantially consumed (See Table 25 below for monitoring of reaction).

TABLE 25

| Formation of Borate Ester Reaction Monitoring by Gas Chromatography; All Samples Analyzed on DB WAX Column. | | | |
|---|---|---|---|
| Sample Number | 3.07 minute Area % | 9.3 minute Area % | 16.8 minute Area % |
| 1 | 57 | 29 | 14 |
| 2 | 22 | 11 | 66 |
| 3 | 0 | 5.4 | 94.5 |

Note:
3.07 minute peak = 4,5,5,5-tetrafluoro-4-(trifluoromethyl)pent-1-ene, 9.3 minute peak = 4,4,5,5-tetramethyl-1,3,2-dioxaborolane, 16.8 minute peak = 2-(4,5,5,5-tetrafluoro-4-(trifluoromethyl)pentyl)-4,4,5,5-tetramehtyl-1,3,2-dioxaborolan A 3M aqueous solution of sodium hydroxide (7.8 grams) can be added to the mixture via an addition funnel over a 15 minute period after which the mixture can be chilled to 0° C. using an ice bath. Hydrogen peroxide (23.6 grams, 35% (wt/wt) aqueous solution) can be added drop-wise over a 15 minute period to the mixture and then the mixture can be washed in H$_2$O (three times). The organic layer can be removed and transferred into a 100 mL three-neck round bottom flask and distilled, to produce an 85% area percent pure (by gas chromatography 4,5,5,5-Tetrafluoro-4-(trifluoromethyl)pentan-1-ol.

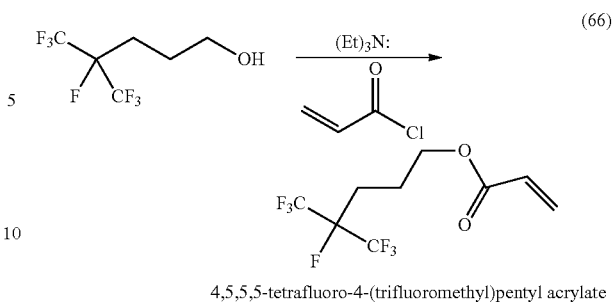

4,5,5,5-tetrafluoro-4-(trifluoromethyl)pentyl acrylate

The 4,5,5,5-Tetrafluoro-4-(trifluoromethyl)pentan-1-ol (2.59 grams, 0.011 moles) and triethylamine (1.3 grams, 0.013 moles) can be added to a 15 mL three-neck RBF to form a mixture. The mixture can be chilled to 0° C. using an ice water bath and acryloyl chloride (1.38 grams, 0.015 moles) can be added to the mixture drop-wise using an addition funnel to the RBF over a 15 minute period. After a 1 hour hold period, 10 mL H$_2$O can be added and two phases can be observed. Water can be decanted off the mixture, the organic phase dried over MgSO$_4$, and analyzed by gas chromatography/mass spectrometry to confirm a new peak having a mass of 283.

An exemplary $R_F$-$Q_M$ such as

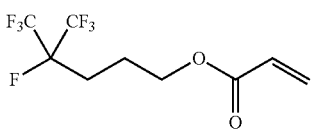

can be provided in solution and conjugated and/or

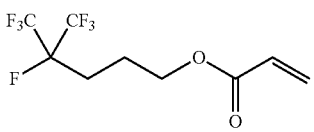

polymerized with another
or another compound to form a complex, such as an oligomer, that can include

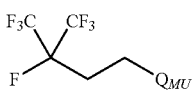

with $Q_{MU}$ representing a remainder of the complex. For example and by way of example only, solutions of $R_F$-monomers can be provided to a substrate and allowed to complex, for example, via evaporating the solvent of the solution to form a complex that includes a $R_F$-monomer unit. Providing these solutions to a substrate such as glass, nylon, and/or cotton and allowing the $R_F$-monomer to become part of a complex, such as coating the substrate.

The surface energy of the complex can be determined using the standard Fowkes method using diiodomethane and water as probe liquids, and the Zisman method of surface energy analysis using octane, decane, tetradecane, and hexadecane as probe liquids. Contact angle of drops of Zisman probe liquids, as well as, the Fowkes probes can be determined, using a Kruss prop Shape Analysis System. Surface energy data of complexes that include $R_F$-$Q_P$ monomer units are recited in the following Tables 26-35.

TABLE 26

Surface Energy Properties of Complexes Applied to Nylon Fabric

| Monomer | Zisman Surface Energy (mJ/m²) | Fowkes Surface Energy (mJ/m²) | Polar Component (mJ/m²) | Dispersive Component (mJ/m²) | Surface Polarity (%) |
|---|---|---|---|---|---|
| 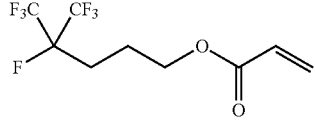 monomer (23700 Mol. wt. as 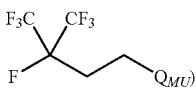) | 19.57 | 19.91 | 0.71 | 19.20 | 3.56 |
| 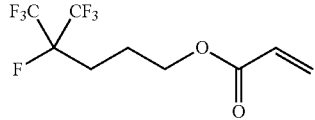 monomer (69200 Mol. wt. as 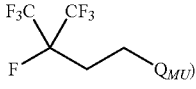) | 19.77 | 20.04 | 0.75 | 19.29 | 3.72 |
| 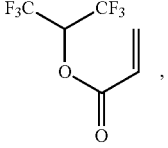 monomer (11700 Mol. wt as complex) | 20.28 | 20.72 | 1.05 | 19.66 | 5.09 |
| 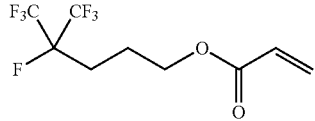 monomer (13875 Mol. wt. as 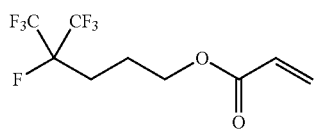) | 20.75 | 21.28 | 1.27 | 20.01 | 5.96 |
| 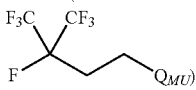 monomer (28500 Mol. wt. as 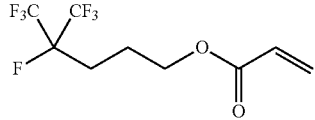) | 20.81 | 21.94 | 1.82 | 20.12 | 8.28 |

TABLE 27

Surface Energy Properties of Complexes Applied to Cleaned Glass

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|
| [F$_3$C-C(CF$_3$)(F)-CH$_2$CH$_2$CH$_2$-O-C(=O)-CH=CH$_2$], monomer (23700 Mol. wt. as [F$_3$C-C(CF$_3$)(F)-CH$_2$CH$_2$CH$_2$-Q$_{MU}$]) | 20.07 | 20.33 | 0.85 | 19.48 | 4.16 |
| [F$_3$C-C(CF$_3$)(F)-CH$_2$CH$_2$CH$_2$-O-C(=O)-CH=CH$_2$], monomer (69200 Mol. wt. as [F$_3$C-C(CF$_3$)(F)-CH$_2$CH$_2$CH$_2$-Q$_{MU}$]) | 20.29 | 20.70 | 0.87 | 19.82 | 4.22 |
| [F$_3$C-CH(CF$_3$)-O-C(=O)-CH=CH$_2$], monomer (11700 Mol. wt as complex) | 20.85 | 21.25 | 1.17 | 20.08 | 5.49 |
| [F$_3$C-C(CF$_3$)(F)-CH$_2$CH$_2$CH$_2$-O-C(=O)-CH=CH$_2$], monomer (13875 Mol. wt. as [F$_3$C-C(CF$_3$)(F)-CH$_2$CH$_2$CH$_2$-Q$_{MU}$]) | 21.22 | 21.78 | 1.39 | 20.39 | 6.38 |
| [F$_3$C-C(CF$_3$)(F)-CH$_2$CH$_2$CH$_2$-O-C(=O)-CH=CH$_2$], monomer (28500 Mol. wt. as [F$_3$C-C(CF$_3$)(F)-CH$_2$CH$_2$CH$_2$-Q$_{MU}$]) | 21.28 | 22.24 | 2.13 | 20.11 | 9.56 |

TABLE 28

Surface Energy Properties of Complexes impregnated into Cleaned Glass

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|
| $F_3C$—$CF_3$, $F$, —O—C(=O)—CH=CH$_2$ from 70% (wt/wt) monomer/30% (wt/wt) laurel methacrylate solution | 20.63 | 20.68 | 1.11 | 19.57 | 5.37 |
| $F_3C$—CH—$CF_3$, O—C(=O)—CH=CH$_2$ from 70% (wt/wt) monomer/30% (wt/wt) methyl methacrylate solution | 20.84 | 20.97 | 1.25 | 19.72 | 5.96 |
| $F_3C$—CH—$CF_3$, O—C(=O)—CH=CH$_2$ from 70% (wt/wt) monomer/30% (wt/wt) lauryl methacrylate solution | 21.02 | 21.08 | 1.33 | 19.75 | 6.32 |
| $F_3C$—$CF_3$, $F$, —O—C(=O)—CH=CH$_2$ from 30% (wt/wt) monomer/70% (wt/wt) lauryl methacrylate solution | 21.30 | 21.37 | 1.45 | 19.92 | 6.8 |
| $F_3C$—CH—$CF_3$, O—C(=O)—CH=CH$_2$ from 30% (wt/wt) monomer/70% (wt/wt) lauryl methacrylate solution | 21.66 | 22.06 | 1.73 | 20.33 | 7.82 |

TABLE 29

Surface Energy Properties of Complexes on Nylon Fabric

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|
| $F_3C$—$CF_3$, $F$, —O—C(=O)—CH=CH$_2$ from 70% (wt/wt) monomer/30% (wt/wt) laurel methacrylate solution | 20.06 | 20.16 | 0.83 | 19.33 | 4.11 |

TABLE 29-continued

Surface Energy Properties of Complexes on Nylon Fabric

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|
| 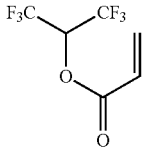 from 70% (wt/wt) monomer/30% (wt/wt) methyl methacrylate solution | 20.37 | 20.43 | 0.95 | 19.48 | 4.67 |
| 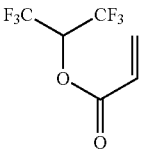 from 70% (wt/wt) monomer/30% (wt/wt) lauryl methacrylate solution | 20.47 | 20.59 | 1.04 | 19.56 | 5.03 |
| 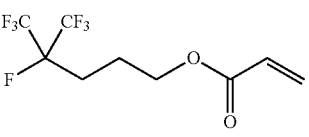 from 30% (wt/wt) monomer/70% (wt/wt) lauryl methacrylate solution | 20.69 | 20.88 | 1.19 | 19.68 | 5.70 |
| 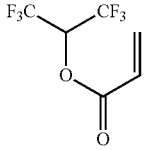 from 30% (wt/wt) monomer/70% (wt/wt) lauryl methacrylate solution | 21.34 | 21.61 | 1.62 | 20.00 | 7.48 |

TABLE 30

Surface Energy Properties of Complexes on Cotton Fabric

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (% (wt/wt)) |
|---|---|---|---|---|---|
|  from 98% (wt/wt) monomer/2% (wt/wt) 2-hydroxyethyl acrylate solution | 20.10 | 20.11 | 0.77 | 19.34 | 3.82 |

TABLE 30-continued

Surface Energy Properties of Complexes on Cotton Fabric

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (% (wt/wt)) |
|---|---|---|---|---|---|
| 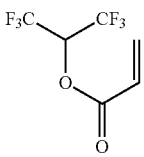 from 98% (wt/wt) monomer/2% (wt/wt) 2-hydroxyethyl acrylate solution | 20.30 | 20.32 | 0.90 | 19.42 | 4.45 |

TABLE 31

Surface Energy Properties of Complexes on Cotton Fabric
(an 87.5% (wt/wt), 6.5% (wt/wt) 1,2,3,4-butanetetracarboxylic acid, and 6.0% (wt/wt) sodium hypophosphite mixture can be prepared, applied to cotton and baked for 2 minutes at 180° C.)

| Monomer | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|
| 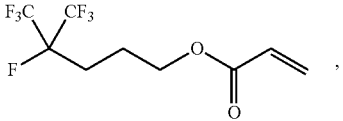 from 28% (wt/wt) monomer/70% (wt/wt) lauryl methacrylate/2% (wt/wt) HEA solution | 21.30 | 21.38 | 1.63 | 19.75 | 7.61 |
| 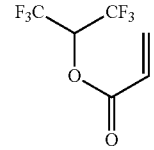 28% (wt/wt) monomer/70% (wt/wt) lauryl methacrylate/2% (wt/wt) HEA solution | 21.46 | 21.58 | 1.72 | 19.86 | 7.99 |

TABLE 32

Surface Energy Properties of Complexes on Nylon

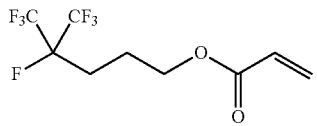

| Monomer % (wt/wt) | Lauryl Methacrylate % (wt/wt) | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|---|
| 25 | 75 | 21.24 | 21.35 | 1.60 | 19.75 | 7.51 |
| 20 | 80 | 21.34 | 21.49 | 1.69 | 19.80 | 7.85 |
| 15 | 85 | 21.56 | 21.74 | 1.77 | 19.69 | 8.16 |
| 10 | 90 | 21.95 | 22.10 | 1.93 | 20.18 | 8.71 |
| 5 | 95 | 22.90 | 23.01 | 2.35 | 20.67 | 10.21 |
| 4 | 96 | 23.20 | 23.37 | 2.54 | 20.83 | 10.87 |
| 3 | 97 | 23.53 | 23.67 | 2.68 | 20.99 | 11.31 |
| 2 | 98 | 23.87 | 24.01 | 2.85 | 21.26 | 11.86 |
| 1 | 99 | 24.29 | 24.45 | 3.08 | 21.38 | 12.58 |

TABLE 33

Surface Energy Properties of Complexes on Nylon

Monomer: F$_3$C-CH(CF$_3$)-O-C(=O)-CH=CH$_2$ (hexafluoroisopropyl acrylate)

| % (wt/wt) | Lauryl Methacrylate % (wt/wt) | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|---|
| 25 | 75 | 21.41 | 21.58 | 1.72 | 19.86 | 7.99 |
| 20 | 80 | 21.70 | 21.85 | 1.84 | 20.02 | 8.40 |
| 15 | 85 | 22.01 | 22.16 | 1.98 | 20.18 | 8.92 |
| 10 | 90 | 22.58 | 22.72 | 2.22 | 20.50 | 9.77 |
| 5 | 95 | 23.42 | 23.57 | 2.63 | 20.94 | 11.16 |
| 4 | 96 | 23.64 | 23.80 | 2.75 | 21.05 | 11.57 |
| 3 | 97 | 23.90 | 24.04 | 2.88 | 21.16 | 11.98 |
| 2 | 98 | 24.23 | 24.38 | 3.06 | 21.32 | 12.54 |
| 1 | 99 | 24.62 | 24.76 | 3.28 | 21.49 | 13.23 |

TABLE 34

Surface Energy Properties of Complexes on Glass

Monomer: F$_3$C-CH(CF$_3$)-O-C(=O)-CH=CH$_2$ (hexafluoroisopropyl acrylate)

| % (wt/wt) | Lauryl Methacrylate % (wt/wt) | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|---|
| 25 | 75 | 21.76 | 21.92 | 1.85 | 20.07 | 8.45 |
| 20 | 80 | 21.89 | 22.06 | 1.91 | 20.15 | 8.67 |
| 15 | 85 | 22.12 | 22.26 | 2.02 | 20.24 | 9.07 |
| 10 | 90 | 22.50 | 22.66 | 2.19 | 20.47 | 9.64 |
| 5 | 95 | 23.39 | 23.55 | 2.63 | 20.93 | 11.15 |
| 4 | 96 | 23.79 | 23.88 | 2.80 | 21.08 | 11.73 |
| 3 | 97 | 24.03 | 24.21 | 2.93 | 21.29 | 12.08 |
| 2 | 98 | 24.40 | 24.56 | 3.13 | 21.43 | 12.73 |
| 1 | 99 | 24.92 | 25.03 | 3.37 | 21.66 | 13.45 |

TABLE 35

Surface Energy Properties of Complexes on Glass

Monomer: F$_3$C-C(CF$_3$)(F)-CH$_2$-CH$_2$-CH$_2$-O-C(=O)-CH=CH$_2$

| % (wt/wt) | Lauryl Methacrylate % (wt/wt) | Zisman Surface Energy (mJ/m$^2$) | Fowkes Surface Energy (mJ/m$^2$) | Polar Component (mJ/m$^2$) | Dispersive Component (mJ/m$^2$) | Surface Polarity (%) |
|---|---|---|---|---|---|---|
| 25 | 75 | 21.99 | 22.11 | 1.94 | 20.18 | 8.75 |
| 20 | 80 | 22.26 | 22.37 | 2.10 | 20.28 | 9.37 |
| 15 | 85 | 22.56 | 22.67 | 2.23 | 20.44 | 9.84 |
| 10 | 90 | 23.07 | 23.26 | 2.49 | 20.77 | 10.70 |
| 5 | 95 | 24.01 | 24.17 | 2.89 | 21.28 | 11.96 |
| 4 | 96 | 24.19 | 24.30 | 3.04 | 21.26 | 12.53 |
| 3 | 97 | 24.42 | 24.56 | 3.15 | 21.41 | 12.83 |
| 2 | 98 | 24.72 | 24.91 | 3.30 | 21.61 | 13.25 |
| 1 | 99 | 25.21 | 25.37 | 3.55 | 21.02 | 13.99 |

$R_F$-monomers can be incorporated with other monomers and then incorporated into the construction of paper materials or used to treat paper materials. $R_F$-monomers can also be used to prepare polymer solutions. Polymeric solutions can be diluted to a percentage aqueous or non-aqueous solution and then applied to substrates to be treated, such as paper plates.

$R_F$-monomers can also be incorporated into copolymers with comonomers such as the dialkyl amino alkyl acrylate or methacrylate or acrylamide or methacrylamide monomer and its amine salt quaternary ammonium or amine oxide form, as described in U.S. Pat. No. 4,147,851, herein incorporated by reference. The general formula for $R_F$-monomers can be $R_F q O_2 CC(R)\!=\!CH_2$, with R being H or $CH_3$, q being an alkylene of 1 to 15 carbon atoms, hydroxyalkylene of 3 to 15 carbon atoms, or $C_n H_{2n}(OC_q H_{2q})_m\!-\!$, $-SO_2 NR_1(C_n H_{2n})\!-\!$, or $-CONR_1(C_n H_{2n})\!-\!$, n is 1 to 15, q is 2 to 4, and m is 1 to 15. Monomers used to form copolymers with acrylates and the $R_F$-monomers include those having amine functionality. These copolymers can be diluted in a solution and applied or incorporated directly into or on substrates to be treated, such as paper.

$R_F$-monomers can also be used to form acrylate polymers or other acrylate monomers consistent with those described in U.S. Pat. No. 4,366,299, herein incorporated by reference. As described, $R_F$-monomers can be incorporated into paper products or applied thereon.

$R_F$-monomers, acrylates and/or acrylics, for example, can be applied to finished carpet or incorporated into the finished carpet fiber before it is woven into carpet. $R_F$-monomers can be applied to carpet by a normal textile finishing process known as padding, in which the carpet is passed through a bath containing the $R_F$-monomer and, for example, latex, water, and/or other additives such as non-rewetting surfaces. The carpet can then be passed through nip rollers to control the rate of the add-on before being dried in a tenter frame. $R_F$-monomers may also be incorporated into the fiber by reacting the fiber with $R_F$-intermediates having isocyanate functionality, $R_F$-isocyanate, for example.

$R_F$ portions can also be incorporated into materials used to treat calcitic and/or siliceous particulate materials. For example, $R_F$-monomers can be incorporated into a copolymer where the copolymer can either be part of a formulation to treat these materials or used by itself to treat these materials as described in U.S. Pat. No. 6,383,569, herein incorporated by reference. The $R_F$-monomer can have the general formula $R_F\text{-Q-A-C(O)}\!-\!C(R)\!=\!CH_2$ wherein $R_F$ is described above, R is H or $CH_3$, A is O, S, or $N(R_1)$, wherein $R_1$ is H or an alkyl of from 1 to 4 carbon atoms, Q is alkylene of 1 to about 15 carbon atoms, hydroxyalkylene of 3 to about 15 carbon atoms, $-(C_n H_{2n})(OC_q H_{2q})_m\!-\!$, $-SO_2\!-\!NR_1(C_n H_{2n})\!-\!$, or $-CONR_1(C_n H_{2n})\!-\!$, wherein $R_1$ is H or an alkyl of 1 to 4 carbon atoms, n is 1 to 15, q is 2 to 4, and m is 1 to 15.

$R_F$-compositions and mixtures containing the $R_F$ portion can be used to treat substrates including hard surfaces like construction materials such as brick, stone, wood, concrete, ceramics, tile, glass, stucco, gypsum, drywall, particle board, and chipboard. These compositions and mixtures can be used alone or in combination with penetration assistance such as non-ionic surfactants. These compositions can be applied to the surface of calcitic and/or siliceous architectural construction material by known methods, for example, by soaking, impregnation, emersion, brushing, rolling, or spraying. The compositions can be applied to the surface to be protected by spraying. Suitable spraying equipment is commercially available. Spraying with a compressed air sprayer is an exemplary method of application to the particular substrate. U.S. Pat. Nos. 6,197,382 and 5,674,961 also describe methods for applying and using polymer solutions and are herein incorporated by reference.

In an exemplary process of producing solutions having components with $R_F$, an $R_F$-intermediate having a methylepoxide functionality may be condensed with a monocarboxylic alkenoic acid to prepare an unsaturated $R_F$-ester (not shown). Exemplary methods for producing these kinds of unsaturated esters are described in U.S. Pat. No. 5,798,415, herein incorporated by reference. Additional esters nay be prepared according to U.S. Pat. No. 4,478,975, herein incorporated by reference. Components of these solutions can also include dimethyl amino ethyl methacrylate, and these components can be applied in organic and inorganic solvents, as described in U.S. Pat. No. 6,120,892 herein incorporated by reference. $R_F$-monomers can also be combined with other monomers to produce copolymers or in solutions with amido and sulfur monomers as described by U.S. Pat. No. 5,629,372 herein incorporated by reference.

$R_F$-intermediates having amine functionality can also be reacted with tetrachlorophthalic anhydride using U.S. Pat. No. 4,043,923 as an exemplary reaction scheme (not shown). U.S. Pat. No. 4,043,923 is herein incorporated by reference. The reaction product can be mixed with a carpet cleaning solution to provide soil repellency.

Referring to scheme (67) below, urethanes, including $R_F$ portions can be prepared from $R_F$-intermediates.

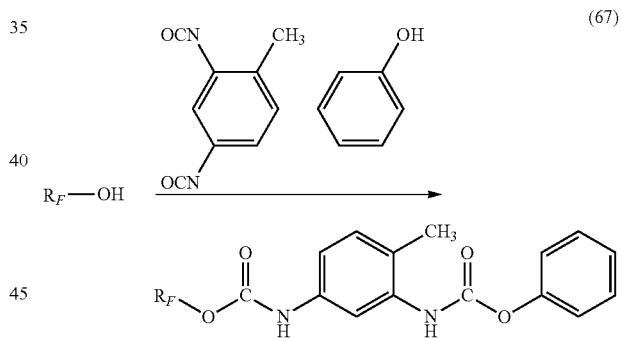

An $R_F$-intermediate ($R_F$—OH) can be combined with hexamethylene diisocyanate polymers (DESMODUR N-100) following the general reaction sequence described in U.S. Pat. No. 5,827,919, herein incorporated by reference, to produce a urethane. Another method for preparing urethanes includes reacting a $R_F$-intermediate ($R_F$—SCN) with epichlorohydrin to produce a "twin tailed" $R_F$-intermediate which can be reacted with diisocyanate and/or a urethane prepolymer as described in U.S. Pat. No. 4,113,748, herein incorporated by reference (not shown). Urethanes having the $R_F$ group can then be incorporated as an additive to compositions such as latex paint. U.S. Pat. No. 5,827,919 describes methods for utilizing these urethanes and is herein incorporated by reference. $R_F$-urethanes and polyurethanes can be used to treat substrates such as carpet, drapery, upholstery, automotive, awning fabrics, and rainwear. Exemplary RF-urethanes, such as $R_F\text{-}Q_u$, can include, but are not limited to those listed in Table 36 below.

TABLE 36

Exemplary R$_F$-Urethanes

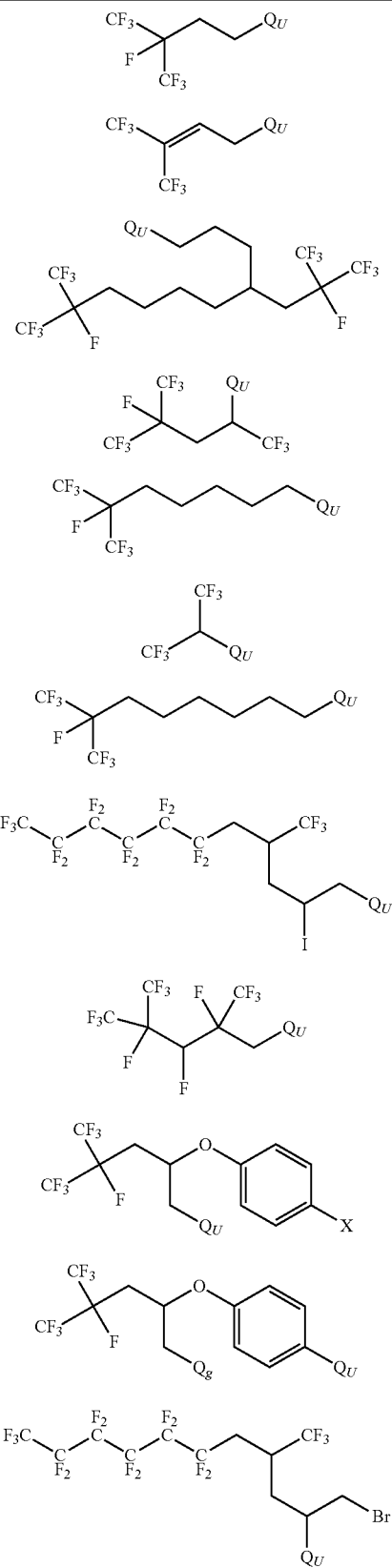

TABLE 36-continued

Exemplary R$_F$-Urethanes

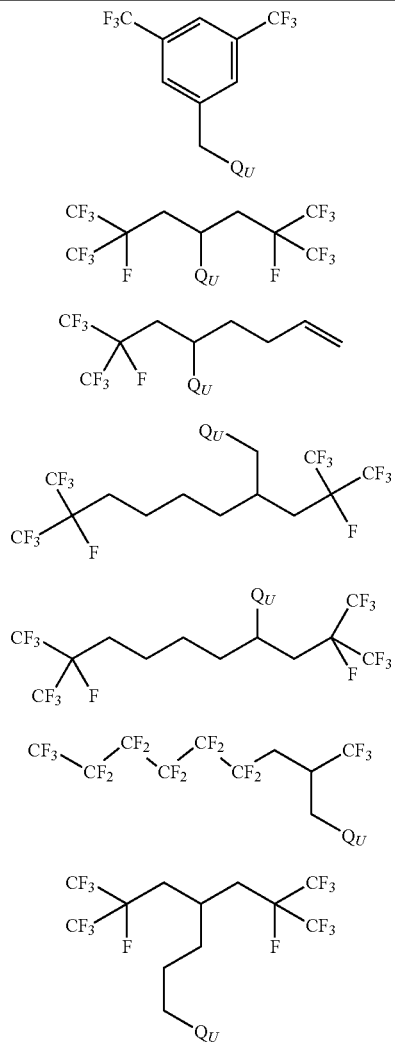

The R$_F$ portion can also be complexed as an acid with amine and quaternary ammonium polymers as described in U.S. Pat. No. 6,486,245, herein incorporated by reference (not shown).

The invention claimed is:

1. A surfactant composition comprising R$_F$-Q$_S$ wherein:
R$_F$ comprises at least two —CF$_3$ groups and—at least one —CH$_2$— group, and Q$_S$ is

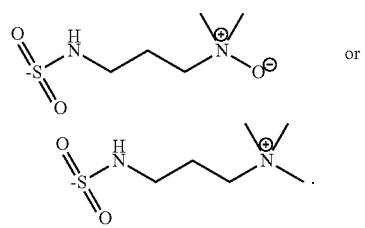

2. The surfactant composition of claim 1 wherein R$_F$ comprises at least one (CF$_3$)$_2$CF— group.

3. The surfactant composition of claim 1 wherein $R_F$ comprises at least four carbons and one of the four carbons comprises a —$CH_2$— group.
4. The surfactant composition of claim 1 wherein $R_F$-$Q_S$ is
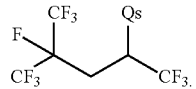
5. The surfactant composition of claim 1 wherein $R_F$-$Q_S$ is
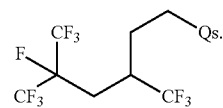
* * * * *